US010883147B2

(12) United States Patent
Wilson et al.

(10) Patent No.: US 10,883,147 B2
(45) Date of Patent: *Jan. 5, 2021

(54) **SERIAL QUANTITATIVE PCR ASSAY FOR DETECTION, SPECIES-DISCRIMINATION AND QUANTIFICATION OF *LEISHMANIA* SPP. IN HUMAN SAMPLES**

(71) Applicant: The United States of America as represented by the Department of Veterans Affairs, Washington, DC (US)

(72) Inventors: Mary E Wilson, Iowa City, IA (US); Jason Weirather, Iowa, IA (US); John E. Donelson, Iowa City, IA (US); Albert Schriefer, Bahia (BR); Edgar Carvalho, Salvador (BR); Selma M. B. Jeronimo, Rn (BR)

(73) Assignee: United States of America as represented by the Department of Veteran Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/275,117

(22) Filed: Sep. 23, 2016

(65) Prior Publication Data

US 2017/0260595 A1 Sep. 14, 2017

Related U.S. Application Data

(63) Continuation of application No. 13/659,746, filed on Oct. 24, 2012, now Pat. No. 9,551,040.

(60) Provisional application No. 61/628,144, filed on Oct. 24, 2011.

(51) Int. Cl.
*C12Q 1/6893* (2018.01)
*C12Q 1/6816* (2018.01)

(52) U.S. Cl.
CPC ........ *C12Q 1/6893* (2013.01); *C12Q 1/6816* (2013.01); *C12Q 2600/16* (2013.01); *Y02A 50/30* (2018.01)

(58) Field of Classification Search
CPC ... C12Q 1/6893; C12Q 2600/16; Y02A 50/30
See application file for complete search history.

(56) References Cited

PUBLICATIONS

Quispe-Tintaya et al. The Journal of Infectious Diseases. 2005. 192:685-692.—Exhibit 1.
Shulz et al. Journal of Clinical Microbiology.2003. 41 (4)1529-1535.—Exhibit 2.
Nasereddin et al. Journal of Clinical Microbiology. 2010. 48(6): 2240-2242—Exhibit 3.
Monbrison et al. Acta Tropica, 2007. 102:97-83—Exhibit 4.
Tupperwar et al. Diagnostic Microbiology and Infectious Disease. 2008. 61:23-30—Exhibit 5.
Talmi-Frank et al. PloS Neglected Tropical Diseases.2100. 4(1):e581—Exhibit 6.
Nicolas et al. Journal of Microbiological Methods. 2002. 51: 295-299—Exhibit 7.
EU370909.1(Mar. 4, 2009) www.ncbi.nlm.nih.gov/nuccore/169160018?sat=17&satkey=18113955—Exhibit 8.

(Continued)

*Primary Examiner* — Joseph G. Dauner
(74) *Attorney, Agent, or Firm* — Ballard Spahr LLP

(57) ABSTRACT

The invention provides a method for determining the presence, species, and/or quantity of *Leishmania* in a sample.

15 Claims, 9 Drawing Sheets

Specification includes a Sequence Listing.

(56) References Cited

PUBLICATIONS

Bretagne et al. Clinical and Diagnostic Laboratory Immunology. 2001. 8(4): 828-831.—Exhibit 9.
Rasmussen et al. BMC Bioinformatics. 2007. 8: 107—Exhibit 10.
GenBank FR799597.1 (Feb. 7, 2011). www.ncbi.nlm.nih.gov/nuccore/322497052?sat=15&satkey=2401445.—Exhibit 11.
Weirather. Journal of Clinical Microbiology, Nov. 2011, p. 3892-3904—Exhibit 12.
Nicolas. Journal of Clinical Microbiology, May 2002, p. 1666-1669—Exhibit 13.
McCoy. Molecular and Biochemical Parasitology 95 (1998) 251-265—Exhibit 14.
AF058760.1 (Jan. 18, 1999)—Exhibit 15.
Buck. Biotechniques.1999. 27(3): 528-536.—Exhibit 16; and.
Mauricio. Parasitology Today, vol. 16, No. 5, 2000—Exhibit 17.

Select primers for sensitive detection kDNA primer sets are the most sensitive means of detecting the parasite.

Examples:
kDNA1 can detect all species tested except *L. braziliensis*, which is detectable by *L. braziliensis* kDNA 3.

Re-evaluate for species identification

Results from the detection step may be sufficient for identifying the species through specific amplification or melt-curve analysis.

Examples:
Specific amplification of *L. braziliensis* by *L. braziliensis* kDNA 3.
Melt-curve analysis of kDNA 1 can distinguish between *L. major* and *L. tropica*.

Select additional primers for species identification as needed

Choose primer sets capable of discriminating between species, either by specific amplification or melt-curve analysis.

Examples:
*L. mexicana* minicircle 1 will specifically amplify *L. mexicana*
*L. amazonensis* kDNA 1 will amplify *L. amazonensis* but not members of the *L. donovani* complex.
MSP associated gene 1 melt-curve will distinguish between *L. donovani* and *L. infantum*

FIG. 2

SERIAL QUANTITATIVE PCR ASSAY FOR DETECTION, SPECIES-DISCRIMINATION AND QUANTIFICATION OF *LEISHMANIA* SPP. IN HUMAN SAMPLES

This patent application is a continuation application of U.S. Ser. No. 13/659,746, filed Oct. 24, 2012, which claims the benefit of the filing date of U.S. Ser. No. 61/628,144, filed Oct. 24, 2011, the contents of all of which are herein incorporated by reference in their entireties into the present patent application.

This invention was made with government support under VA Gulf War RFA awarded by Department of Veterans Affairs and Grant Nos. R01-AI48822, AI045540, R01 AI067874-01, R01 AI059451, R01 AI076233-01, P50 AI-30639 and P50 AI-074321 awarded by NIH/NIAID. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

The *Leishmania* spp. are kinetoplastid protozoa that are transmitted to humans and other mammalian hosts by, e.g., a sand fly vector. The spectrum of symptomatic human leishmaniasis is wide, and the most important factor determining the clinical outcome of infection seems to be the species of *Leishmania*. Nonetheless, there are variable clinical presentations of disease due to each species (10, 22, 30), and increasing reports document atypical presentations of leishmaniasis, sometimes but not always in the setting of the immunocompromised (16,53). Differentiation between the *Leishmania* species is an issue since there are overlapping and dynamic geographic regions of risk, and different susceptibilities to treatment (7,15). Thus, a method of diagnosis that is sensitive enough to detect low levels of the parasite in asymptomatic or early symptomatic infection, and can distinguish between the different *Leishmania* species, would be of tremendous utility in endemic and non-endemic regions (38).

Procedures for diagnosis of leishmaniasis are often invasive, and isolates are frequently difficult to grow in vitro. Tests to distinguish between the *Leishmania* species have traditionally involved separation of isoenzymes in culture-derived parasites, which takes several weeks (12). The *Leishmania* spp. have been detected in and isolated from blood cultures of subjects with all forms of leishmaniasis (20, 39, 40), and in the blood of asymptomatic individuals living in regions of risk (11, 25, 34, 39). The possibility that *Leishmania* may be present in the bloodstream more often than previously recognized led us to hypothesize that amplification-based methods to detect parasite DNA in blood or serum might be a feasible means of diagnosis.

Nucleic acid-based methods avoid the need for parasite cultivation, replacing this with either hybridization or amplification (24, 24, 35, 39, 67). The latter approaches provide the advantage of increased sensitivity. Amplification methods reported for the detection of individual *Leishmania* species include conventional PCR (4, 21, 63) or quantitative PCR methods, including reverse transcriptase quantitative polymerase chain reaction (RT-qPCR), DNA-based qPCR, quantitative nucleic acid sequence-based amplification (QT-NASBA) and in situ hybridization to quantify *Leishmania* spp. in blood or tissue samples (63).

Protozoa belonging to the order Kinetoplastida, including *Leishmania* spp. and *Trypanosoma* spp., are characterized by a prominent kinetoplast structure containing the mitochondrial DNA in the parasites' single mitochondrion. Whereas *Leishmania* spp. have 35-36 chromosomes in their nuclear genomes (52), the kinetoplast contains hundreds of DNA maxicircles encoding genes that are destined for RNA editing, and thousands of DNA minicircles, circular molecules with a conserved origin of replication encoding guide RNA sequences for RNA editing (13). Because of their abundance, specificity and repetitive nature, kinetoplast DNA (kDNA) sequences have frequently been targeted for nucleic acid based detection (33, 42, 43, 48, 49). A drawback of the use of kDNA for parasite quantification is the uncertainty of whether the kDNA copy number differs between *Leishmania* species, strains, and growth stages.

The goal of this study was to develop a serial nucleic acid amplification based method for diagnosis and speciation of *Leishmania* spp. parasites in human or animal-derived tissues. As such we developed a set of primers and probes for serial qPCR assays. The assays were sensitive enough to detect low levels of parasites, and to distinguish between *Leishmania* species in human specimens. Using non-species discriminating probes, we quantified the relative differences in kinetoplastid DNA (kDNA) copy numbers between parasite species, among isolates of the same species, and between stages of the same parasite strain. The serial qPCR assays has potential applications for diagnosis and species discrimination, as well as novel approaches to determining parasite load and following treatment response in infected humans.

The *Leishmania* species cause a variety of human disease syndromes. Methods for diagnosis and species differentiation are insensitive and many require invasive sampling. Although quantitative PCR (qPCR) methods are reported for *Leishmania* detection, no systematic method to quantify parasites and determine the species in clinical specimens is established.

We developed a serial qPCR strategy to identify and rapidly differentiate *Leishmania* species, and quantify parasites in clinical or environmental specimens. SYBR green qPCR may be employed, with corresponding Taqman assays for validation. Screening primers recognize kinetoplast minicircle DNA of all *Leishmania* species. Species identification employs further qPCR set(s) individualized for geographic regions, combining species discriminating probes with melt curve analysis. The assay was sufficient to detect, speculate and quantify *Leishmania* spp. in sera, cutaneous biopsies, or cultured isolates from subjects in Bangladesh or Brazil with different forms of leishmaniasis. The multicopy kDNA probes were the most sensitive and useful for quantification based on promastigote standard curves. To test their validity for quantification, kDNA copy numbers were compared between *Leishmania* species, isolates, and life stages using qPCR. Maxicircle and minicircle copy numbers differed up to 6 fold between *Leishmania* species, but differences were smaller between strains of the same species. Amastigote and promastigote *Leishmania* life stages retained similar numbers of kDNA maxi- or minicircles. Thus, serial qPCR is useful for *Leishmania* detection and speciation, and for absolute quantification when compared to a standard curve from the same *Leishmania* species.

SUMMARY OF THE INVENTION

The invention provides for methods for determining the presence, species, and/or quantity of a *Leishmania* in a sample comprising: (a) contacting the sample with a set of nucleic acid primer pairs with primer sequences common to all *Leishmania* species or to a subset of *Leishmania* species, so as to make *Leishmania*-primer pair complexes; (b) exposing the complexes to a thermo-stable polymerase to produce double-stranded DNAs containing the primer sequences; (c) determining the time or number of temperature cycles at which a threshold level of double-stranded DNA product and/or pyrophosphate product is reached being indicative of on-target specificity and/or quantity of *Leishmania* in the sample; and (d) determining the melting temperature of the double-stranded DNA product of (c), a characteristic melting temperature being indicative of particular *Leishmania* species so detected by the primer; thereby determining the presence, species, and/or quantity of *Leishmania* in the sample.

In another embodiment for determining the presence, species, and/or quantity of *Leishmania* in a sample, the method comprises contacting the sample with a set of nucleic acid primer pairs with primer sequences unique to a particular *Leishmania* species, so as to make *Leishmania*-primer pair complexes; exposing the complexes to a thermo-stable polymerase to produce double-stranded DNAs containing the primer sequences; determining the time or number of temperature cycles at which a threshold level of double-stranded DNA product and/or pyrophosphate product is reached which is indicative of on-target specificity and quantity of *Leishmania* in the sample; and identifying the particular *Leishmania* species by the unique primers used so as to thereby determine the presence, species, and quantity of *Leishmania* in the sample. In this embodiment, the step of characterizing the double-stranded DNA product by its melting temperature is not necessary for identifying the particular *Leishmania* species but may be performed as a control to assure on-target specificity of the reaction.

In another embodiment for determining the presence, species, and/or quantity of a *Leishmania* in a sample, the method comprises: (a) contacting the sample with a set of nucleic acid primer pairs with primer sequences unique to a particular *Leishmania* species, so as to make *Leishmania*-primer pair complexes; (b) exposing the complexes to a thermo-stable polymerase to produce double-stranded DNAs containing the primer sequences; (c) determining the time or number of temperature cycles at which a threshold level of double-stranded DNA product and/or pyrophosphate product is reached being indicative of on-target specificity and/or quantity of *Leishmania* in the sample; and (d) identifying the particular *Leishmania* species by the unique primers used; thereby determining the presence, species, and/or quantity of *Leishmania* in the sample, wherein quantity of *Leishmania* in the sample is determined by examining a single copy gene or a known copy gene number within a *Leishmania* species and comparing against a reference standard curve generated with different known amount of the particular *Leishmania* species.

In one embodiment for detecting the presence of *Leishmania*, the method comprises (a) contacting a sample with a nucleic acid primer having a complementary sequence so as to produce a complex; (b) contacting the sample with another nucleic acid primer having a different complementary sequence so as to produce a complex; (c) exposing the complexes to a thermo-stable polymerase so as to produce double stranded nucleic acid from the primers in (a) and (b); and (d) detecting the double stranded nucleic acid so produced, the presence of the double stranded nucleic acid being indicative of the presence of *Leishmania* in the sample, wherein the nucleic acid primers from step (a) and (b) are selected from the group consisting of GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); GGGTAGGGGCGTTCTGC (SEQ ID NO:1) and TACACCAACCCCCAGTTTGC (SEQ ID NO:2) (kDNA 1 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (*L. major* MSP associated gene 1 forward and reverse primers, respectively); GACGACGACGAGGAGGATGG (SEQ ID NO:61) and GCGACGGGTACAGGGAGTTG (SEQ ID NO:62) (*L. amazonensis* DNA polymerase forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); or a combination thereof. The rate of the production of multiple double-stranded DNAs containing the primer sequences may be monitored and/or the pyrophosphate product thereof may be monitored, either of which may be indicative of the amount or quantity of *Leishmania* present in the sample.

In another embodiment for determining the presence, quantity and/or species of *Leishmania* in a sample, the sample comprises: (a) contacting the sample with a set of nucleic acid primer pairs with primer sequences common to all *Leishmania* species or to a subset of *Leishmania* species, so as to make *Leishmania*-primer pair complexes; (b) contacting the sample with a set of nucleic acid probe or probes modified with a detectable marker and a quencher for the detectable marker and having a sequence complementary to a region bounded by each primer pair in (a); (c) exposing the complexes to a thermo-stable polymerase to produce multiple double-stranded DNAs containing the primer sequences; (d) detecting the presence and/or rate of release of the detectable marker from the modified nucleic acid in (b), which is indicative of quantity and/or particular *Leishmania* species; thereby determining the presence, quantity and/or species of *Leishmania* in the sample.

In another embodiment for determining the presence, quantity and/or species of *Leishmania* in a sample, the method comprises: (a) contacting the sample with a set of nucleic acid primer pairs with primer sequences unique to a particular *Leishmania* species, so as to make *Leishmania*-primer pair complexes; (b) contacting the sample with a set of nucleic acid probe or probes modified with a detectable marker and a quencher for the detectable marker and having a sequence complementary to a region bounded by each primer pair in (a); (c) exposing the complexes to a thermostable polymerase to produce multiple double-stranded DNAs containing the primer sequences; (d) detecting the presence and/or rate of release of the detectable marker from the modified nucleic acid in (b), which is indicative of quantity and/or presence of Leishmania in the sample; and (e) identifying the particular Leishmania species by the unique primers used; thereby determining the presence, quantity and/or species of Leishmania in the sample.

The invention also provides novel compositions as described herein.

BRIEF DESCRIPTION OF THE FIGURES

FIG. 2. Flow chart of the serial qPCR assay. The chart shows a minimal application of the serial diagnostic qPCR assay to determine presence and species of Leishmania in a sample. In step 1 (detection), an unknown DNA sample can be tested for the presence of Leishmania spp. DNA using SYBR primers. kDNA 1 amplifies most species. L. (V.) braziliensis Mini-circle 3 amplifies kDNA sequences within L. (V.) braziliensis, a primer set that would be included when testing samples from Latin America to provide the most sensitive detection across species. In step 2, a sample which has tested positive for the presence of parasite kDNA 1, but not L. braziliensis kDNA 3, can be classified according to its species. Melt curve analysis of kDNA1 amplicons can distinguish between several Old World species (L. (L.) tropica, L. (L.) major, L. (L.) infantum). Application of SYBR green melt curve analysis using MSP associated gene (MAG) 1 is capable of separating L. (L.) chagasi and L. (L.) infantum from L. (L.) donovani. The presence or absence of L. (L.) mexicana specific minicircle amplicons is sufficient to differentiate between L. (L.) mexicana and L. (L.) major. Distinguishing L. (L.) amazonensis from the members of the L. (L.) donovani complex requires an additional such as L. (L.) amazonensis kDNA 2 (not shown in flowchart). The inability of any primer pairs tested to distinguish between L. (L.) chagasi and L. (L.) infantum is consistent with the current belief that these species are virtually identical (44). Note: The primer sets listed are minimal sets. It is advisable to select additional primers based upon the expected Leishmania species in the geographic region.

DETAILED DESCRIPTION OF THE INVENTION

Compositions of the Invention

Figure 1:
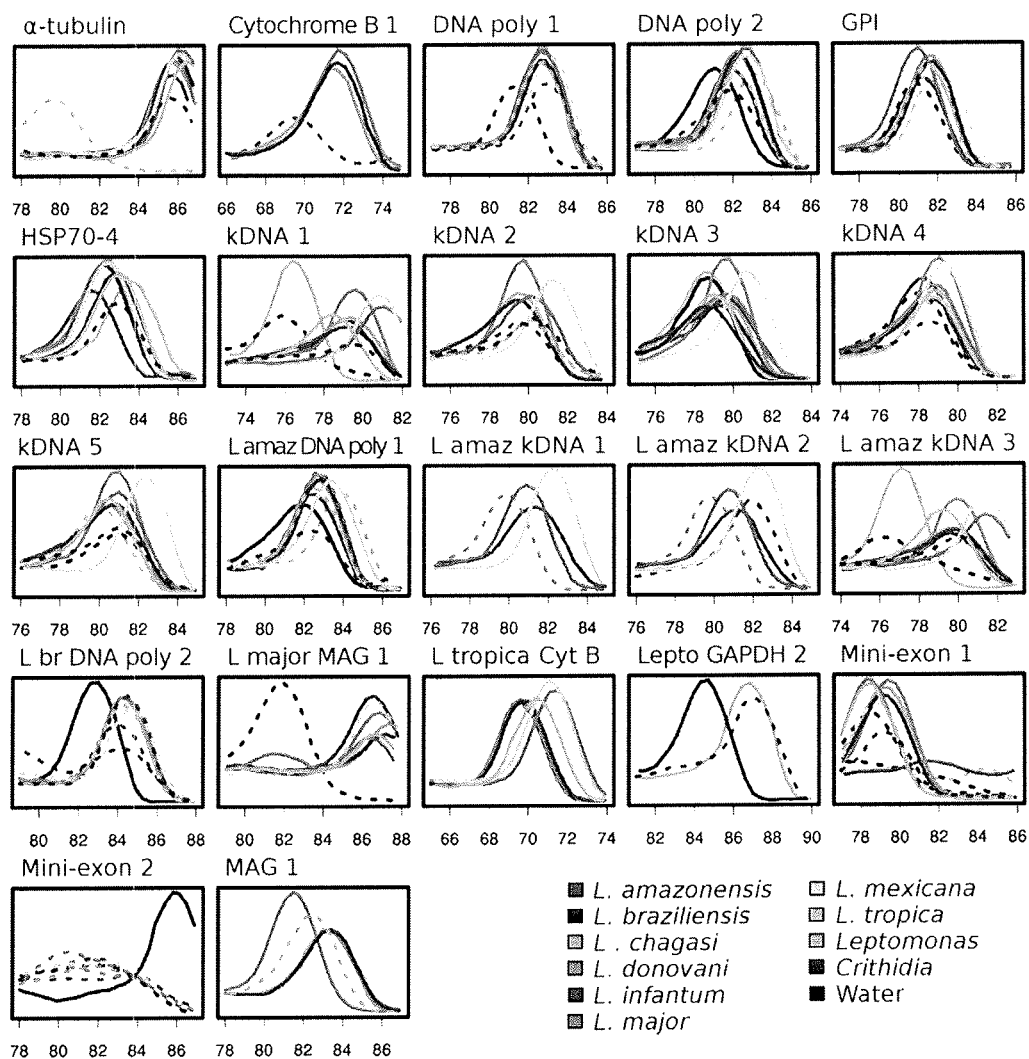
FIG. 1. Melt curves of selected qPCR assays useful for species discrimination. Rate of change in the intensity of the fluorescent qPCR signal is plotted across a 10 degree temperature range for each species with each primer set. Data are only shown for sets that amplified with a CT (cycle threshold) of less than 30, and showed peaks of melt curves greater than 1 degree apart between species. Peaks of curves indicate the melting temperature of the amplicon. Each melt curve is color-coded according to the parasite species it represents. Plots with a solid line indicate that the reaction amplified with a CT less than 25. Plots with a dotted line indicate the reaction amplified with a CT greater than or equal to 25 but less than 30.

The invention provides composition comprising novel nucleic acid sequences of the invention. Suitable examples of the nucleic acid sequence of the invention include but not limited to the following embodiments: (1) a nucleic acid sequence consisting of: GGGTAGGGGCGTTCTGC (SEQ ID NO:1) (kDNA 1 minicircle forward primer); (2) a nucleic acid sequence consisting of: TACACCAACCCCCAGTTTGC (SEQ ID NO:2) (kDNA 1 minicircle reverse primer); (3) a nucleic acid sequence consisting of: GGGTAGGGGCGTTCTGC (SEQ ID NO:3) (kDNA 3 minicircle forward primer); (4) a nucleic acid sequence consisting of: CCCGGCCTATTTTACACCAACC (SEQ ID NO:4) (kDNA 3 minicircle reverse primer); (5) a nucleic acid sequence consisting of: GGGTGCAGAAATCCCGTTCA (SEQ ID NO:5) (kDNA 4 minicircle forward primer); (6) a nucleic acid sequence consisting of: CCCGGCCCTATTTTACACCA (SEQ ID NO:6) (kDNA 4 minicircle reverse primer); (7) a nucleic acid sequence consisting of: AATGGGTGCAGAAATCCCGTTC (SEQ ID NO:7) (kDNA 7 minicircle forward primer); (8) a nucleic acid sequence consisting of: CCACCACCCGGCCCTATTTTAC (SEQ ID NO:8) (kDNA 7 minicircle reverse primer); (9) a nucleic acid sequence consisting of: GGTCCCGGCCCAAACTTTTC (SEQ ID NO:9) (L. (L.) amazonensis kDNA 1 forward primer); (10) a nucleic acid sequence consisting of: CCGGGGTTTCGCACTCATT (SEQ ID NO:10) (L. (L.) amazonensis kDNA 1 reverse primer); (11) a nucleic acid sequence consisting of: GGTAGGGGCGTTCTGCGAAT (SEQ ID NO:11) (L. (L.) amazonensis kDNA 2 forward primer); (12) a nucleic acid sequence consisting of: CCCGGCCTATTTTACACCAACC (SEQ ID NO:12) (*L.* (L.) *amazonensis* kDNA 2 reverse primer); (13) a nucleic acid sequence consisting of: GGGTAGGGGCGTTCTGC (SEQ ID NO:13) (*L.* (L.) *amazonensis* kDNA 3 forward primer); (14) a nucleic acid sequence consisting of: TACACCAACCCCCAGTTTGC (SEQ ID NO:14) (*L.* (L.) *amazonensis* kDNA 3 reverse primer); (15) a nucleic acid sequence consisting of: TGAGTGCAGAAACCCCGTTCATA (SEQ ID NO:15) (*L.* (L.) *amazonensis* kDNA 4 forward primer); (16) a nucleic acid sequence consisting of: ACACCAACCCCCAGTTGTGA (SEQ ID NO:16) (*L.* (L.) *amazonensis* kDNA 4 reverse primer); (17) a nucleic acid sequence consisting of: AATTTCGCAGAACGCCCCTAC (SEQ ID NO:17) (*L.* (V.) *braziliensis* kDNA 1 forward primer); (18) a nucleic acid sequence consisting of: GTACTCCCCGACATGCCTCTG (SEQ ID NO:18) (*L.* (V.) *braziliensis* kDNA 1 reverse primer); (19) a nucleic acid sequence consisting of: ACGGGGTTTCTGCACCCATT (SEQ ID NO:19) (*L.* (L.) *major* Minicircle 1 forward primer); (20) a nucleic acid sequence consisting of: GTAGGGGCGTTCTGCGAAAA (SEQ ID NO:20) (*L.* (L.) *major* Minicircle 1 reverse primer); (21) a nucleic acid sequence consisting of: AATGCGAGTGTTGCCCTTTTG (SEQ ID NO:21) (*L.* (L.) *mexicana* Minicircle 1 forward primer); (22) a nucleic acid sequence consisting of: GCCGAACAACGCCATATTAACC (SEQ ID NO:22) (*L.* (L.) *mexicana* Minicircle 1 reverse primer); (23) a nucleic acid sequence consisting of: GGGGGTTGGTGTAAAATAGGG (SEQ ID NO:23) (*L.* (L.) *tropica* Minicircle 1 forward primer); (24) a nucleic acid sequence consisting of: ACCACCAGCAGAAGGTCAAAG (SEQ ID NO:24) (*L.* (L.) *tropica* Minicircle 1 reverse primer); (25) a nucleic acid sequence consisting of: GCGGTGGCTGGTTTTAGATG (SEQ ID NO:25) (*L.* (L.) *donovani* Minicircle 1 forward primer); (26) a nucleic acid sequence consisting of: TCCAATGAAGCCAAGCCAGT (SEQ ID NO:26) (*L.* (L.) *donovani* Minicircle 1 reverse primer); (27) a nucleic acid sequence consisting of: ATTTTAGTATGAGTGGTAGGTTTTGTT (SEQ ID NO:27) (Cytochrome B 1 forward primer); (28) a nucleic acid sequence consisting of: CAATAACTGGGACGGTTGCT (SEQ ID NO:28) (Cytochrome B 1 reverse primer); (29) a nucleic acid sequence consisting of: GCGGAGAGGAAAGAAAAGGCTTA (SEQ ID NO:29) (*L.* (L.) *amazonensis* Cytochrome B1 forward primer); (30) a nucleic acid sequence consisting of: AAAAGTCATGCTAAACACACACCACA (SEQ ID NO:30) (*L.* (L.) *amazonensis* Cytochrome B1 reverse primer); (31) a nucleic acid sequence consisting of: CAGGTTGCTTACTACGTGTTTATGGTG (SEQ ID NO:31) (*L.* (L.) *tropica* Cytochrome B 1 forward primer); (32) a nucleic acid sequence consisting of: TCGTATTACAAACCCTAAATCAAAATCTCA (SEQ ID NO:32) (*L.* (L.) *tropica* Cytochrome B 1 reverse primer); (33) a nucleic acid sequence consisting of: TCAGGTTGCTTACTACGTGTTTATGGTG (SEQ ID NO:33) (*L.* (L.) *tropica* Cytochrome B 2 forward primer); (34) a nucleic acid sequence consisting of: TGCTAAACAAACACCACATATGATCTGC (SEQ ID NO:34) (*L.* (L.) *tropica* Cytochrome B 2 reverse primer); (35) a nucleic acid sequence consisting of: TGACACACATATTTTAGTGTGGGTGGTAGG (SEQ ID NO:35) (*L.* (L.) *tropica* Cytochrome B 3 forward primer); (36) a nucleic acid sequence consisting of: TCCCCAATAAGACATCATTGTACATGGTAA (SEQ ID NO:36) (*L.* (L.) *tropica* Cytochrome B 3 reverse primer); (37) a nucleic acid sequence consisting of: CACATATTTTAGTGTGGGTGGTAGGTTTTG (SEQ ID NO:37) (*L.* (L.) *tropica* Cytochrome B 4 forward primer); (38) a nucleic acid sequence consisting of: TCCCCAATAAGACATCATTGTACATGGTAA (SEQ ID NO:38) (*L.* (L.) *tropica* Cytochrome B 4 reverse primer); (39) a nucleic acid sequence consisting of: GCTTGGTTGGATTATTTTTGCTG (SEQ ID NO:39) (Maxicircle 1 forward primer); (40) a nucleic acid sequence consisting of: AACAACATTTTAACTCTTGTAGGATTCG (SEQ ID NO:40) (Maxicircle 1 reverse primer); (41) a nucleic acid sequence consisting of: GAGGTGTTTGCCCGCATC (SEQ ID NO:41) (Alpha-tubulin 1 forward primer); (42) a nucleic acid sequence consisting of: CTCGCCCATGTCGTCG (SEQ ID NO:42) (Alpha-tubulin 1 reverse primer); (43) a nucleic acid sequence consisting of: AGGAGGATGGCAAGCGGAAG (SEQ ID NO:43) (DNA polymerase 2 forward primer); (44) a nucleic acid sequence consisting of: GCGACGGGTACAGGGAGTTG (SEQ ID NO:44) (DNA polymerase 2 reverse primer); (45) a nucleic acid sequence consisting of: CGAAACTTCCGGAACCTGTCTT (SEQ ID NO:45) (Mini-exon 1 forward primer); (46) a nucleic acid sequence consisting of: CACCACACGCACGCACAC (SEQ ID NO:46) (Mini-exon 1 reverse primer); (47) a nucleic acid sequence consisting of: GTGTGGTGGCGGGTGTATGT (SEQ ID NO:47) (Mini-exon 2 forward primer); (48) a nucleic acid sequence consisting of: GCCCAGGTCGCTGTGAGG (SEQ ID NO:48) (Mini-exon 2 reverse primer); (49) a nucleic acid sequence consisting of: AGAGCGTGCCTTGGATTGTG (SEQ ID NO:49) (MSP Associated Gene 1 (MAG 1) forward primer); (50) a nucleic acid sequence consisting of: CGCTGCGTTGATTGCGTTG (SEQ ID NO:50) (MSP Associated Gene 1 (MAG 1) reverse primer); (51) a nucleic acid sequence consisting of: AGTTTTGGTTGGCGCTCCTG (SEQ ID NO:51) (MSP Associated Gene 2 (MAG 2) forward primer); (52) a nucleic acid sequence consisting of: CCCACTCGCTTTCCTTGGTC (SEQ ID NO:52) (MSP Associated Gene 2 (MAG 2) reverse primer); (53) a nucleic acid sequence consisting of: CGACCCTGTCACCACCACAG (SEQ ID NO:53) (SIDER repeat 1 forward primer); (54) a nucleic acid sequence consisting of: GAGGCCACCCTATCGCTGAC (SEQ ID NO:54) (SIDER repeat 1 reverse primer); (55) a nucleic acid sequence consisting of: TCGTTGAGGGAGGAGGTGTTTC (SEQ ID NO:55) (*L.* (V.) *braziliensis* DNA polymerase 1 forward primer); (56) a nucleic acid sequence consisting of: TCGGCTTTGAGGTTGGCTTC (SEQ ID NO:56) (*L.* (V.) *braziliensis* DNA polymerase 1 reverse primer); (57) a nucleic acid sequence consisting of: ACGTCGCCAACTGCTTCACC (SEQ ID NO:57) (*L.* (V.) *braziliensis* DNA polymerase 2 forward primer); (58) a nucleic acid sequence consisting of: GTGTTCGCACCGCCTTGAC (SEQ ID NO:58) (*L.* (V.) *braziliensis* DNA polymerase 2 reverse primer); (59) a nucleic acid sequence consisting of: GTCGTTGTCCGTGTCGCTGT (SEQ ID NO:59) (*L.* (L.) *major* MSP associated gene 1 (*L. major* MAG 1) forward primer); (60) a nucleic acid sequence consisting of: CGCTGTGTGTGTCCGTGTGT (SEQ ID NO:60) (*L.* (L.) *major* MSP associated gene 1 (*L. major* MAG 1) reverse primer); (61) a nucleic acid sequence consisting of: GACGACGACGAGGAGGATGG (SEQ ID NO:61) (*L.* (L.) *amazonensis* DNA polymerase 1 forward primer); (62) a nucleic acid sequence consisting of: GCGACGGGTACAGGGAGTTG (SEQ ID NO:62) (*L.* (L.) *amazonensis* DNA polymerase 1 reverse primer); (63) a nucleic acid sequence consisting of: GAAGGTGCAGTCCCTCGTGT (SEQ ID NO:63) (HSP70-1 forward primer); (64) a nucleic acid sequence consisting of:

CCTCCGTCTGCTTGCTCTTG (SEQ ID NO:64) (HSP70-1 reverse primer); (65) a nucleic acid sequence consisting of: TCGAGATCGACGCGTTGTT (SEQ ID NO:65) (HSP70-4 forward primer); (66) a nucleic acid sequence consisting of: CCGCACAGCTCCTCGAA (SEQ ID NO:66) (HSP70-4 reverse primer); (67) a nucleic acid sequence consisting of: GGAGAAACTCACGGCACAGG (SEQ ID NO:67) (SLACS forward primer); (68) a nucleic acid sequence consisting of: GCGCCTCGTAGGTCACAGTT (SEQ ID NO:68) (SLACS reverse primer); (69) a nucleic acid sequence consisting of: TGGAGCGGGTGCATTAACTC (SEQ ID NO:69) (*Leptomonas* Mini-exon 1 forward primer); (70) a nucleic acid sequence consisting of: GGTCTCGAGGTGCCCATGAC (SEQ ID NO:70) (*Leptomonas* Mini-exon 1 reverse primer); (71) a nucleic acid sequence consisting of: AGAAGCCGGATGTGCTTGTG (SEQ ID NO:71) (*Leptomonas* GAPDH 2 forward primer); (72) a nucleic acid sequence consisting of: GCCCTCAGCCTTCACCTTGT (SEQ ID NO:72) (*Leptomonas* GAPDH 2 reverse primer); (73) a nucleic acid sequence consisting of: GCCCTGTGAGGAGGACGAAC (SEQ ID NO:73) (Human TNF alpha 1 forward primer); (74) a nucleic acid sequence consisting of: AAGAGGTTGAGGGTGTCTGAAGGA (SEQ ID NO:74) (Human TNF alpha 1 reverse primer); (75) a nucleic acid sequence consisting of: GCGCTCCCCAAGAAGACAGG (SEQ ID NO:75) (Human TNF alpha 2 forward primer); (76) a nucleic acid sequence consisting of: TGCCACGATCAGGAAGGAGAAG (SEQ ID NO:76) (Human TNF alpha 2 reverse primer); (77) a nucleic acid sequence consisting of: GGGCTCTCCAGAACATCATCC (SEQ ID NO:77) (Human GAPDH 1 forward primer); (78) a nucleic acid sequence consisting of: CCAGTGAGCTTCCCGTTCAG (SEQ ID NO:78) (Human GAPDH 1 reverse primer); (79) a nucleic acid sequence consisting of: CATCAAGAAGGTGGTGAAGCAG (SEQ ID NO:79) (Human GAPDH 2 forward primer); (80) a nucleic acid sequence consisting of: CGTCAAAGGTGGAGGAGTGG (SEQ ID NO:80) (Human GAPDH 2 reverse primer); (81) a nucleic acid sequence consisting of: GCATGGCCTTCCGTGTCC (SEQ ID NO:81) (Human GAPDH 3 forward primer); and (82) a nucleic acid sequence consisting of: CGCCTGCTTCACCACCTTCT (SEQ ID NO:82) (Human GAPDH 3 reverse primer).

The invention further provides compositions comprising novel nucleic acid primer pairs which include but not limited to the following embodiments: (1) GGGTAGGGGCGTTCTGC (SEQ ID NO:1) and TACACCAACCCCCAGTTTGC (SEQ ID NO:2) (kDNA 1 minicircle forward and reverse primers, respectively); (2) GGGTAGGGGCGTTCTGC (SEQ ID NO:3) and CCCGGCCTATTTTACACCAACC (SEQ ID NO:4) (kDNA 3 minicircle forward and reverse primers, respectively); (3) GGGTGCAGAAATCCCGTTCA (SEQ ID NO:5) and CCCGGCCCTATTTTACACCA (SEQ ID NO:6) (kDNA 4 minicircle forward and reverse primers, respectively); (4) AATGGGTGCAGAAATCCCGTTC (SEQ ID NO:7) and CCACCACCCGGCCCTATTTTAC (SEQ ID NO:8) (kDNA 7 minicircle forward and reverse primers, respectively); (5) GGTCCCGGCCCAAACTTTTC (SEQ ID NO:9) and CCGGGGTTTCGCACTCATT (SEQ ID NO:10) (*L.* (*L.*) *amazonensis* kDNA 1 forward and reverse primers, respectively); (6) GGTAGGGGCGTTCTGCGAAT (SEQ ID NO:11) and CCCGGCCTATTTTACACCAACC (SEQ ID NO:12) (*L.* (*L.*) *amazonensis* kDNA 2 forward and reverse primers, respectively); (7) GGGTAGGGGCGTTCTGC (SEQ ID NO:13) and TACACCAACCCCCAGTTTGC (SEQ ID NO:14) (*L.* (*L.*) *amazonensis* kDNA 3 forward and reverse primers, respectively); (8) TGAGTGCAGAAACCCCGTTCATA (SEQ ID NO:15) and ACACCAACCCCCAGTTGTGA (SEQ ID NO:16) (*L.* (*L.*) *amazonensis* kDNA 4 forward and reverse primers, respectively); (9) AATTTCGCAGAACGCCCCTAC (SEQ ID NO:17) and GTACTCCCCGACATGCCTCTG (SEQ ID NO:18) (*L.* (*V.*) *braziliensis* kDNA 1 forward and reverse primers, respectively); (10) ACGGGGTTTCTGCACCCATT (SEQ ID NO:19) and GTAGGGGCGTTCTGCGAAAA (SEQ ID NO:20) (*L.* (*L.*) *major* Minicircle 1 forward and reverse primers, respectively); (11) AATGCGAGTGTTGCCCTTTTG (SEQ ID NO:21) and GCCGAACAACGCCATATTAACC (SEQ ID NO:22) (*L.* (*L.*) *mexicana* Minicircle 1 forward and reverse primers, respectively); (12) GGGGGTTGGTGTAAAATAGGG (SEQ ID NO:23) and ACCACCAGCAGAAGGTCAAAG (SEQ ID NO:24) (*L.* (*L.*) *tropica* Minicircle 1 forward and reverse primers, respectively); (13) GCGGTGGCTGGTTTTAGATG (SEQ ID NO:25) and TCCAATGAAGCCAAGCCAGT (SEQ ID NO:26) (*L.* (*L.*) *donovani* Minicircle 1 forward and reverse primers, respectively); (14) ATTTTAGTATGAGTGGTAGGTTTTGTT (SEQ ID NO:27) and CAATAACTGGGACGGTTGCT (SEQ ID NO:28) (Cytochrome B 1 forward and reverse primers, respectively); (15) GCGGAGAGGAAAGAAAAGGCTTA (SEQ ID NO:29) and AAAAGTCATGCTAAACACACACCACA (SEQ ID NO:30) (*L.* (*L.*) *amazonensis* Cytochrome B1 forward and reverse primers, respectively); (16) CAGGTTGCTTACTACGTGTTTATGGTG (SEQ ID NO:31) and TCGTATTACAAACCCTAAATCAAAATCTCA (SEQ ID NO:32) (*L.* (*L.*) *tropica* Cytochrome B 1 forward and reverse primers, respectively); (17) TCAGGTTGCTTACTACGTGTTTATGGTG (SEQ ID NO:33) and TGCTAAACAAACACCACATATGATCTGC (SEQ ID NO:34) (*L.* (*L.*) *tropica* Cytochrome B 2 forward and reverse primers, respectively); (18) TGACACACATATTTTAGTGTGGGTGGTAGG (SEQ ID NO:35) and TCCCCAATAAGACATCATTGTACATGGTAA (SEQ ID NO:36) (*L.* (*L.*) *tropica* Cytochrome B 3 forward and reverse primers, respectively); (19) CACATATTTTAGTGTGGGTGGTAGGTTTTG (SEQ ID NO:37) and TCCCCAATAAGACATCATTGTACATGGTAA (SEQ ID NO:38) (*L.* (*L.*) *tropica* Cytochrome B 4 forward and reverse primers, respectively); (20) GCTTGGTTGGATTATTTTTGCTG (SEQ ID NO:39) and AACAACATTTTAACTCTTGTAGGATTCG (SEQ ID NO:40) (Maxicircle 1 forward and reverse primers, respectively); (21) GAGGTGTTTGCCCGCATC (SEQ ID NO:41) and CTCGCCCATGTCGTCG (SEQ ID NO:42) (Alpha-tubulin 1 forward and reverse primers, respectively); (22) AGGAGGATGGCAAGCGGAAG (SEQ ID NO:43) and GCGACGGGTACAGGGAGTTG (SEQ ID NO:44) (DNA polymerase 2 forward and reverse primers, respectively); (23) CGAAACTTCCGGAACCTGTCTT (SEQ ID NO:45) and CACCACACGCACGCACAC (SEQ ID NO:46) (Mini-exon 1 forward and reverse primers, respectively); (24) GTGTGGTGGCGGGTGTATGT (SEQ ID NO:47) and GCCCAGGTCGCTGTGAGG (SEQ ID NO:48) (Mini-exon 2 forward and reverse primers, respectively); (25) AGAGCGTGCCTTGGATTGTG (SEQ ID NO:49) and CGCTGCGTTGATTGCGTTG (SEQ ID NO:50) (MSP Associated Gene 1 (MAG 1) forward and reverse primers, respectively); (26) AGTTTTGGTTGGCGCTCCTG (SEQ ID NO:51) and CCCACTCGCTTTCCTTGGTC (SEQ ID NO:52) (MSP Associated Gene 2 (MAG 2) forward and reverse primers, respectively); (27) CGACCCTGTCAC-CACCACAG (SEQ ID NO:53) and GAGGCCACCC-TATCGCTGAC (SEQ ID NO:54) (SIDER repeat 1 forward and reverse primers, respectively); (28) TCGTTGAGG-GAGGAGGTGTTTC (SEQ ID NO:55) and TCGGCTTT-GAGGTTGGCTTC (SEQ ID NO:56) (*L.* (*V.*) *braziliensis* DNA polymerase 1 forward and reverse primers, respectively); (29) ACGTCGCCAACTGCTTCACC (SEQ ID NO:57) and GTGTTCGCACCGCCTTGAC (SEQ ID NO:58) (*L.* (*V.*) *braziliensis* DNA polymerase 2 forward and reverse primers, respectively); (30) GTCGTTGTCCGTGTCGCTGT (SEQ ID NO:59) and CGCTGTGTGTGTCCGTGTGT (SEQ ID NO:60) (*L.* (*L.*) *major* MSP associated gene 1 (*L. major* MAG 1) forward and reverse primers, respectively); (31) GACGACGACGAGGAGGATGG (SEQ ID NO:61) and GCGACGGGTACAGGGAGTTG (SEQ ID NO:62) (*L.* (*L.*) *amazonensis* DNA polymerase 1 forward and reverse primers, respectively); (32) GAAGGTGCAGTCCCTCGTGT (SEQ ID NO:63) and CCTCCGTCTGCTTGCTCTTG (SEQ ID NO:64) (HSP70-1 forward and reverse primers, respectively); (33) TCGAGATCGACGCGTTGTT (SEQ ID NO:65) and CCGCACAGCTCCTCGAA (SEQ ID NO:66) (HSP70-4 forward and reverse primers, respectively); (34) GGAGAAACTCACGGCACAGG (SEQ ID NO:67) and GCGCCTCGTAGGTCACAGTT (SEQ ID NO:68) (SLACS forward and reverse primers, respectively); (35) TGGAGCGGGTGCATTAACTC (SEQ ID NO:69) and GGTCTCGAGGTGCCCATGAC (SEQ ID NO:70) (*Leptomonas* Mini-exon 1 forward and reverse primers, respectively); (36) AGAAGCCGGATGTGCTTGTG (SEQ ID NO:71) and GCCCTCAGCCTTCACCTTGT (SEQ ID NO:72) (*Leptomonas* GAPDH 2 forward and reverse primers, respectively); (37) GCCCTGTGAGGAGGACGAAC (SEQ ID NO:73) and AAGAGGTTGAGGGTGTCT-GAAGGA (SEQ ID NO:74) (Human TNF alpha 1 forward and reverse primers, respectively); (38) GCGCTCCC-CAAGAAGACAGG (SEQ ID NO:75) and TGCCAC-GATCAGGAAGGAGAAG (SEQ ID NO:76) (Human TNF alpha 2 forward and reverse primers, respectively); (39) GGGCTCTCCAGAACATCATCC (SEQ ID NO:77) and CCAGTGAGCTTCCCGTTCAG (SEQ ID NO:78) (Human GAPDH 1 forward and reverse primers, respectively); (40) CATCAAGAAGGTGGTGAAGCAG (SEQ ID NO:79) and CGTCAAAGGTGGAGGAGTGG (SEQ ID NO:80) (Human GAPDH 2 forward and reverse primers, respectively); and (41) GCATGGCCTTCCGTGTCC (SEQ ID NO:81) and CGCCTGCTTCACCACCTTCT (SEQ ID NO:82) (Human GAPDH 3 forward and reverse primers, respectively).

In another embodiment, the invention provides for composition comprising a novel nucleic acid probe sequences (also referred to as a third nucleic acid probe) which include but are not limited to the following embodiments: (1) a nucleic acid sequence consisting of ACCCCCAGTTTCCCGCCCCG (SEQ ID NO:83); (2) a nucleic acid sequence consisting of CCCCAGTTTCCCGCCCCGGA (SEQ ID NO:84); (3) a nucleic acid sequence consisting of TGGCCTTGGGGCGTGCAAACTGG (SEQ ID NO:85); (4) a nucleic acid sequence consisting of TCCTGGCGGGGTTTTCGCT (SEQ ID NO:86); (5) a nucleic acid sequence consisting of CCCATACCAC-CAAACGCAGCCCA (SEQ ID NO:87); (6) a nucleic acid sequence consisting of CCATGTACGATGATGTCGTATT-GAGGTCTAACA (SEQ ID NO:88); (7) a nucleic acid sequence consisting of CTTTAGGTAGGGAGTTGTAC-TACGTTTTTTGACCT (SEQ ID NO:89); (8) a nucleic acid sequence consisting of TGAGGGCATGGAGGAGGGCG (SEQ ID NO:90); (9) a nucleic acid sequence consisting of TGGGGTCGAGCACCATGCCGCC (SEQ ID NO:91); (10) a nucleic acid sequence consisting of CGGCAAGAT-TTTGGAAGCGCGCA (SEQ ID NO:92); (11) a nucleic acid sequence consisting of TGCGCACTGCACTGTCGCCCCC (SEQ ID NO:93); (12) a nucleic acid sequence consisting of CGCT-GAGAGCGAGGCAGGCACGC (SEQ ID NO:94); (13) a nucleic acid sequence consisting of CCTTCC-CAAACGCCTCCCCTGCCCC (SEQ ID NO:95); and (14) a nucleic acid sequence consisting of CACCGCCTG-GAGCCCTGGGGC (SEQ ID NO:96).

METHODS OF THE INVENTION

The invention provides a method for determining the presence, species, and/or quantity of a *Leishmania* in a sample.

In one embodiment of the invention, the method comprises contacting the sample with a set of nucleic acid primer pairs with primer sequences so as to obtain *Leishmania*-primer pair complexes. The primer sequences may be common to all *Leishmania* species or to a subset of *Leishmania* species. The nucleic acid primer pairs may be deoxyribonucleic acid (DNA) or a modified deoxyribonucleic acid. In another example, the nucleic acid primer pairs are ribonucleic acid (RNA) or modified ribonucleic acid. In a further example, the nucleic acid primer pairs are mixed RNA-DNA hybrid or modified RNA-DNA hybrid.

Examples of nucleic acid primer pairs include, but are not limited to: GGGTAGGGGCGTTCTGC (SEQ ID NO:1) and TACACCAACCCCAGTTTGC (SEQ ID NO:2) (kDNA 1 minicircle forward and reverse primers, respectively); AACTTTTCTGGTCCTCCGGGTAG (SEQ ID NO:97) and ACCCCCAGTTTCCCGCC (SEQ ID NO:98) (kDNA 2 forward and reverse primers, respectively); GGGTAGGGGCGTTCTGC (SEQ ID NO:3) and CCCGGCCTATTTTACACCAACC (SEQ ID NO:4) (kDNA 3 minicircle forward and reverse primers, respectively); GGGTGCAGAAATCCCGTTCA (SEQ ID NO:5) and CCCGGCCCTATTTTACACCA (SEQ ID NO:6) (kDNA 4 minicircle forward and reverse primers, respectively); CTTTTCTGGTCCTCCGGGTAGG (SEQ ID NO:99) and CCACCCGGCCCTATTTTACACCAA (SEQ ID NO:100) (kDNA 5 minicircle forward and reverse primers, respectively); AATGGGTGCAGAAATCCCGTTC (SEQ ID NO:7) and CCACCACCCGGCCCTATTTTAC (SEQ ID NO:8) (kDNA 7 minicircle forward and reverse primers, respectively); GGTCCCGGCCCAAACTTTTC (SEQ ID NO:9) and CCGGGGTTTCGCACTCATTT (SEQ ID NO:10) (*L.* (*L.*) *amazonensis* kDNA 1 forward and reverse primers, respectively); GGTAGGGGCGTTCTGCGAAT (SEQ ID NO:11) and CCCGGCCTATTTTACACCAACC (SEQ ID NO:12) (*L.* (*L.*) *amazonensis* kDNA 2 forward and reverse primers, respectively); GGGTAGGGGCGTTCTGC (SEQ ID NO:13) and TACACCAACCCCAGTTTGC (SEQ ID NO:14) (*L.* (*L.*) *amazonensis* kDNA 3 forward and reverse primers, respectively); TGAGTGCAGAAACCCCGTT-CATA (SEQ ID NO:15) and ACAC-CAACCCCCAGTTGTGA (SEQ ID NO:16) (*L.* (*L.*) *amazonensis* kDNA 4 forward and reverse primers, respectively); AATTTCGCAGAACGCCCCTAC (SEQ ID NO:17) and GTACTCCCCGACATGCCTCTG (SEQ ID NO:18) (*L.* (*V.*) *braziliensis* kDNA 1 forward and reverse primers, respectively); TGCTATAAAATCGTAC-CACCCGACA (SEQ ID NO:101) and GAACGGGGTTTCTGTATGCCATTT (SEQ ID NO:1102) (*L.* (*V.*) *braziliensis* kDNA 3 forward and reverse primers, respectively); TCCGCAGGAGACTTCGTATG (SEQ ID NO:103) and CACGACTATCCACCCCATCC (SEQ ID NO:104) (*L.* (*L.*) *infantum* Minicircle 1 forward and reverse primers, respectively); ACGGGGTTTCTGCACCCATT (SEQ ID NO:19) and GTAGGGGCGTTCTGCGAAAA (SEQ ID NO:20) (*L.* (*L.*) *major* Minicircle 1 forward and reverse primers, respectively); AATGCGAGTGTTGCCCTTTTG (SEQ ID NO:21) and GCCGAACAACGCCATATTAACC (SEQ ID NO:22) (*L.* (*L.*) *mexicana* Minicircle 1 forward and reverse primers, respectively); GGGGGTTGGTGTAAAATAGGG (SEQ ID NO:23) and ACCACCAGCAGAAGGTCAAAG (SEQ ID NO:24) (*L.* (*L.*) *tropica* Minicircle 1 forward and reverse primers, respectively); GCGGTGGCTGGTTTTAGATG (SEQ ID NO:25) and TCCAATGAAGCCAAGCCAGT (SEQ ID NO:26) (*L.* (*L.*) *donovani* Minicircle 1 forward and reverse primers, respectively); ATTTTAGTAT-GAGTGGTAGGTTTTGTT (SEQ ID NO:27) and CAATAACTGGGACGGTTGCT (SEQ ID NO:28) (Cytochrome B 1 forward and reverse primers, respectively); GCGGAGAGGAAAGAAAAGGCTTA (SEQ ID NO:29) and AAAAGTCATGCTAAACACACACCACA (SEQ ID NO:30) (*L.* (*L.*) *amazonensis* Cytochrome B1 forward and reverse primers, respectively); CAGGTTGCTTAC-TACGTGTTTATGGTG (SEQ ID NO:31) and TCGTATTA-CAAACCCTAAATCAAAATCTCA (SEQ ID NO:32) (*L.* (*L.*) *tropica* Cytochrome B 1 forward and reverse primers, respectively); TCAGGTTGCTTACTACGTGTTTATGGTG (SEQ ID NO:33) and TGCTAAACAAACACCACATAT-GATCTGC (SEQ ID NO:34) (*L.* (*L.*) *tropica* Cytochrome B 2 forward and reverse primers, respectively); TGACACA-CATATTTTAGTGTGGGTGGTAGG (SEQ ID NO:35) and TCCCCAATAAGACATCATTGTACATGGTAA (SEQ ID NO:36) (*L.* (*L.*) *tropica* Cytochrome B 3 forward and reverse primers, respectively); CACATATTT-TAGTGTGGGTGGTAGGTTTTG (SEQ ID NO:37) and TCCCCAATAAGACATCATTGTACATGGTAA (SEQ ID NO:38) (*L.* (*L.*) *tropica* Cytochrome B 4 forward and reverse primers, respectively); GCTTGGTTGGATTAT-TTTTGCTG (SEQ ID NO:39) and AACAACATTT-TAACTCTTGTAGGATTCG (SEQ ID NO:40) (Maxicircle 1 forward and reverse primers, respectively); GAGGTGTTTGCCCGCATC (SEQ ID NO:41) and CTCGCCCATGTCGTCG (SEQ ID NO:42) (Alpha-tubulin 1 forward and reverse primers, respectively); TGTCGCTTGCAGACCAGATG (SEQ ID NO:105) and GCATCGCAGGTGTGAGCA (SEQ ID NO:106) (DNA polymerase 1 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (Mini-exon 1 forward and reverse primers, respectively); GTGTGGTGGCGGGTGTATGT (SEQ ID NO:47) and GCCCAGGTCGCTGTGAGG (SEQ ID NO:48) (Mini-exon 2 forward and reverse primers, respectively); AGAGCGTGCCTTGGATTGTG (SEQ ID NO:49) and CGCTGCGTTGATTGCGTTG (SEQ ID NO:50) (MSP Associated Gene 1 (MAG 1) forward and reverse primers, respectively); AGTTTTGGTTGGCGCTCCTG (SEQ ID NO:51) and CCCACTCGCTTTCCTTGGTC (SEQ ID NO:52) (MSP Associated Gene 2 (MAG 2) forward and reverse primers, respectively); CGACCCTGTCACCAC-CACAG (SEQ ID NO:53) and GAGGCCACCC-TATCGCTGAC (SEQ ID NO:54) (SIDER repeat 1 forward and reverse primers, respectively); TCGTTGAGGGAG-GAGGTGTTTC (SEQ ID NO:55) and TCGGCTTT-GAGGTTGGCTTC (SEQ ID NO:56) (*L.* (*V.*) *braziliensis* DNA polymerase 1 forward and reverse primers, respectively); ACGTCGCCAACTGCTTCACC (SEQ ID NO:57) and GTGTTCGCACCGCCTTGAC (SEQ ID NO:58) (*L.* (*V.*) *braziliensis* DNA polymerase 2 forward and reverse primers, respectively); GTCGTTGTCCGTGTCGCTGT (SEQ ID NO:59) and CGCTGTGTGTGTCCGTGTGT (SEQ ID NO:60) (*L.* (*L.*) *major* MSP associated gene 1 (*L. major* MAG 1) forward and reverse primers, respectively); GACGACGACGAGGAGGATGG (SEQ ID NO:61) and GCGACGGGTACAGGGAGTTG (SEQ ID NO:62) (*L.* (*L.*) *amazonensis* DNA polymerase 1 forward and reverse primers, respectively); CCAGATGCCGACCAAAGC (SEQ ID NO:107) and CGCGCACGTGATGGATAAC (SEQ ID NO:108) (GPI forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); TCGAGATCGACGCGTTGTT (SEQ ID NO:65) and CCGCACAGCTCCTCGAA (SEQ ID NO:66) (HSP70-4 forward and reverse primers, respectively); GGAGAAACT-CACGGCACAGG (SEQ ID NO:67) and GCGCCTCGTAGGTCACAGTT (SEQ ID NO:68) (SLACS forward and reverse primers, respectively); TGGAGCGGGTGCATTAACTC (SEQ ID NO:69) and GGTCTCGAGGTGCCCATGAC (SEQ ID NO:70) (*Leptomonas* Mini-exon 1 forward and reverse primers, respectively); AGAAGCCGGATGTGCTTGTG (SEQ ID NO:71) and GCCCTCAGCCTTCACCTTGT (SEQ ID NO:72) (*Leptomonas* GAPDH 2 forward and reverse primers, respectively); GCCCTGTGAGGAGGACGAAC (SEQ ID NO:73) and AAGAGGTTGAGGGTGTCTGAAGGA (SEQ ID NO:74) (Human TNF alpha 1 forward and reverse primers, respectively); GCGCTCCCCAAGAAGACAGG (SEQ ID NO:75) and TGCCACGATCAGGAAGGAGAAG (SEQ ID NO:76) (Human TNF alpha 2 forward and reverse primers, respectively); GGGCTCTCCAGAACATCATCC (SEQ ID NO:77) and CCAGTGAGCTTCCCGTTCAG (SEQ ID NO:78) (Human GAPDH 1 forward and reverse primers, respectively); CATCAAGAAGGTGGT-GAAGCAG (SEQ ID NO:79) and CGTCAAAGGTGGAG-GAGTGG (SEQ ID NO:80) (Human GAPDH 2 forward and reverse primers, respectively); and GCATGGCCTTCCGTGTCC (SEQ ID NO:81) and CGCCTGCTTCACCACCTTCT (SEQ ID NO:82) (Human GAPDH 3 forward and reverse primers, respectively).

Examples of *Leishmania* include but are not limited to *Leishmania tropica, Leishmania chagasi, Leishmania infantum, Leishmania donovani, Leishmania major, Leishmania braziliensis, Leishmania guyanensis, Leishmania panamensis, Leishmania mexicana,* and *Leishmania amazonensis.*

The method may further comprise exposing the *Leishmania*-primer pair to a thermo-stable polymerase (for example, a thermo-stable DNA polymerase) so as to produce double-stranded DNAs containing the primer sequences. The double stranded nucleic acid so produced may be several kilo-basepairs, less than several kilo-basepairs, less than 1 kilo-basepairs, less than 500 basepairs, less than 300 basepairs, less than 200 basepairs, or, less than 150 basepairs. For example, the double-stranded nucleic acid so produced may be less than 200 basepairs and most are less than 150 basepairs.

Such thermo-stable DNA polymerase are known in the art and include any of Taq polymerase from *Thermus aquaticus*, Pfu DNA polymerase *Pyrococcus furiosus*, Vent polymerase from *Thermococcus litoralis*, Tth polymerase from *Thermus thermophilus*, or Bst DNA polymerase from *Bacillus stearothermophilus* but are not limited to these examples.

In addition to being able to replicate DNA, thermo-stable polymerases may have 5'-to-3' exonuclease activity, 3'-to-5' exonuclease activity ("proof-reading" activity), reverse transcriptase activity, or strong strand displacement activity. The polymerase may be purified from its original organism and subsequently modified to obtain desired activity, or alternatively, produced by recombinant DNA methods true to its primary amino acid sequence or alternatively modified or truncated so as to have desired properties. In addition, the purified native or recombinant thermo-stable polymerase may be further treated with an antibody or antibodies or with chemical or chemicals so as to obtain a polymerase characteristic suitable for a particular application, as is known in the art.

Examples of recombinant modified polymerase include (1) AmpliTaq DNA polymerase (Applied Biosystems, Inc.), which is a recombinant, thermostable, 94 kDa DNA polymerase with 5'-to-3' exonuclease activity but no 3'-to-5' exonuclease activity encoded by a modified form of the *Thermus aquaticus* DNA polymerase gene which is expressed and purified from an *Escherichia coli* host; (2) AmpliTaq Gold® DNA polymerase (Applied Biosystems, Inc.), which a chemically modified form of AmpliTaq® DNA Polymerase that requires heat above the annealing temperature of primer to its template to activate its enzymatic activity; (3) AmpliTaq Gold® DNA polymerase, LD (Applied Biosystems, Inc.), which is a highly purified form of AmpliTaq Gold® DNA polymerase; (4) AmpliTaq® DNA polymerase, Stoffel Fragment, which is a modified form of AmpliTaq® DNA Polymerase from which the N-terminal 289 amino acids are deleted thereby changing it enzymatic property such that it is twice as thereto-stable with broader range of optimal polymerase activity from 2 mM to 10 mM magnesium and loss of 5'-to-3' exonuclease activity; (5) rTth DNA polymerase (Applied Biosciences, Inc.) is an ultrapure, thermostable recombinant DNA polymerase with ability to reverse transcribe RNA to cDNA in the presence of $Mn^{+2}$ ion, and to also act as a DNA polymerase for PCR amplification; and (6) rTth DNA Polymerase, XL (Applied Biosystems, Inc.) which is an ultrapure, thermostable recombinant DNA polymerase blend, designed for amplification of DNA or RNA targets>5 kb [XL (eXtra Long) PCR] and is formulated to include the optimal amount of 3'-to-5' exonuclease activity.

Examples of suitable primer pairs are found in Table 2. Additionally, primer pairs which are common to *Leishmania* species, include, but are not limited to: GGGTAGGGGCGTTCTGC (SEQ ID NO:3) and CCCGGCCTATTTTACACCAACC (SEQ ID NO:4) (e.g., referred to in some later examples as kDNA 3 mini-circle forward and reverse primers, respectively); GGGTGCAGAAATCCCGTTCA (SEQ ID NO:5) and CCCGGCCCTATTTTACACCA (SEQ ID NO:6) (e.g., referred to in some later examples as kDNA 4 mini-circle forward and reverse primers, respectively); GGGTAGGGGCGTTCTGC (SEQ ID NO:1) and TACACCAACCCCCAGTTTGC (SEQ ID NO:2) (e.g., referred to in some later examples as kDNA 1 mini-circle forward and reverse primers, respectively); AATGGGTGCAGAAATCCCGTTC (SEQ ID NO:7) and CCACCACCCGGCCCTATTTTAC (SEQ ID NO:8) (e.g., referred to in some later examples as kDNA 7 mini-circle forward and reverse primers, respectively); GGGTAGGGGCGTTCTGC (SEQ ID NO:13) and TACAC-CAACCCCCAGTTTGC (SEQ ID NO:14) (e.g., referred to in some later examples as *L. amazonensis* kDNA 3 forward and reverse primers, respectively); AGGAG-GATGGCAAGCGGAAG (SEQ ID NO:43) and GCGACGGGTACAGGGAGTTG (SEQ ID NO:44) (e.g., referred to in some later examples as DNA polymerase 2 forward and reverse primers, respectively); CGAAACTTCCGGAACCTGTCTT (SEQ ID NO:45) and CACCACACGCACGCACAC (SEQ ID NO:46) (e.g., referred to in some later examples as mini-exon 1 forward and reverse primers, respectively); GTCGTTGTCCGTGTCGCTGT (SEQ ID NO:59) and CGCTGTGTGTGTCCGTGTGT (SEQ ID NO:60) (e.g., referred to in some later examples as *L. major* MSP associated gene 1 forward and reverse primers, respectively); GACGACGACGAGGAGGATGG (SEQ ID NO:61) and GCGACGGGTACAGGGAGTTG (SEQ ID NO:62) (e.g., referred to in some later examples as *L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (e.g., referred to in some later examples as HSP70-1 forward and reverse primers, respectively); and TCGAGATCGACGCGTTGTT (SEQ ID NO:65) and CCGCACAGCTCCTCGAA (SEQ ID NO:66) (e.g., referred to in some later examples as HSP70-4 forward and reverse primers, respectively). As is the convention, sequences throughout this application are written 5' to 3' in the same direction that the text is read.

In one embodiment, at least one of the primers may be attached to a detectable marker. In another embodiment, the primer attached to the detectable marker may also be attached to a quencher.

The double-stranded DNAs containing the primer sequences may be maintained in the same temperature or may be cycled between at least two different temperatures over a suitable time period to produce multiple double-stranded DNAs containing the primer sequences. In an embodiment of the invention, when the double-stranded DNAs containing the primer sequences are cycled between at least two different temperatures, the temperature differential is more than about an 18° C. differential. In another embodiment, the temperature is cycled between 95° C. and 60° C. Additionally, in a further embodiment, the temperature is cycled for 40 cycles, but preferably measurements are read from, e.g., SYBR green assays, at 30 cycles or less. This cycle limit is based on the observation that primer dimers often occur after 30 cycles in e.g., SYBR green reactions. In yet another embodiment, the temperature is constant. In an additional embodiment, the temperature may be around 60° C. to 65° C.

Monitoring for the presence of double-stranded DNA or pyrophosphate are well-known in the art and include detection through ultraviolet absorption, fluorescence, light scattering, colorimetric, or chromogenic detection. In one embodiment, fluorescence detection includes the use of SYBR® Green Dye I as a minor groove binder for double-stranded DNA or ethidium bromide as an intercalator of double-stranded DNA or calcein as an indicator for the presence of pyrophosphate. For example, fluorescence obtained from SYBR® Green Dye I binding to double-stranded DNA can be used to monitor the production of double-stranded DNA in a real-time PCR system in which a 488 nm laser line from an argon ion laser is used to excite the fluorophore-DNA complex (peak absorption of 497 nm) and subsequent monitoring of its emission at a longer wavelength (peak emission of 520 nm). Other detection means are possible and are well known in the art.

In another example, ethidium bromide can be used to stain and quantify double-stranded DNA, which can be detected or visualized by virtue of its fluorescence following excitation by ultraviolet light.

In a third example, using manganese ion-bound calcein, the presence of pyrophosphate can be detected following displacement of manganese ion from calcein by pyrophosphate resulting in calcein fluorescence further enhanced in the presence of magnesium ion. In one embodiment, light scattering detection includes assessing the turbidity of pyrophosphate salt. The pyrophosphate salt may be magnesium pyrophosphate. In the current invention, the preferred embodiment is the detection of double-stranded DNA through SYBR® Green Dye I staining. However, other dyes are possible and well known in the art.

The method may further include a step of determining the time or number of temperature cycles at which a threshold level of double-stranded DNA product and/or pyrophosphate product is reached which may be indicative of on-target specificity and/or quantity of Leishmania in the sample. As known in the art (Applied Biosystems, Inc., Application Note, "Real-time PCR: Understanding Ct" at link http://www3.appliedbiosystems.com/cms/groups/mcb_marketing/documents/generaldocuments/cms_053906.pdf), the threshold level is set at a level corresponding to the exponential phase of DNA amplification. In one example, the threshold level is 0.2 based on SYBER® Green Dye I detection method for presence of double-stranded DNA performed in a 7900 fast real-time PCR system from Applied Biosystems, Inc., and the temperature is cycled for less than about 30 cycles. In other examples, the temperature is cycled for 40 cycles but preferably 30 cycles or less. The melting temperature of the double-stranded DNA product may be determined and a characteristic melting temperature is indicative of particular Leishmania species, either one particular species or a group of species, so detected by the primer pair.

Melting temperatures of any of the following probes can be useful for distinguishing between the Leishmania species: DNA polymerase 2, GPI, HSP70-4, kDNA 1 minicircle, kDNA 2 minicircle, kDNA 3 minicircle, kDNA 4 minicircle, kDNA 5 minicircle, L. amazonensis DNA polymerase 1, L. amazonensis kDNA 1, L. amazonensis kDNA 2, L. amazonensis kDNA 3, L. braziliensis DNA polymerase 2, L. major MAG 1, L. tropica Cytochrome B, mini-exon 1, and mini-exon 2, MAG 1. Table 7 and FIG. 1 provide examples.

TABLE 7

Melting temperature of selected SYBR green assays are listed below to exemplify the relative differences in Tm of double stranded DNA products produced from templates of different Leishmania species. The absolute Tm may vary from lab to lab because of slight differences in reagents used. Also, the below list is not exhaustive.

| Primer set | Species | Approximate Melt Temperature ° C. (±1-2° C.) |
|---|---|---|
| DNA polymerase 2 | L. (L.) chagasi | 82.2 |
| DNA polymerase 2 | L. (L.) donovani | 82.2 |
| DNA polymerase 2 | L. (V.) braziliensis | 80.9 |
| HSP70-4 | L. (L.) amazonensis | 81.8 |
| HSP70-4 | L. (L.) tropica | 83.2 |
| HSP70-4 | L. (V.) braziliensis | 82.9 |
| L. (L.) amazonensis kDNA 1 | L. (L.) major | 80.9 |
| L. (L.) amazonensis kDNA 1 | L. (L.) mexicana | 82.4 |
| L. (L.) amazonensis kDNA 2 | L. (L.) major | 80.7 |
| L. (L.) amazonensis kDNA 2 | L. (L.) mexicana | 82.2 |
| L. (L.) amazonensis kDNA 3 | L. (L.) amazonensis | 79.6 |
| L. (L.) amazonensis kDNA 3 | L. (L.) chagasi | 79.6 |
| L. (L.) amazonensis kDNA 3 | L. (L.) donovani | 79.9 |
| L. (L.) amazonensis kDNA 3 | L. (L.) infantum | 79.7 |
| L. (L.) amazonensis kDNA 3 | L. (L.) major | 81.4 |
| L. (L.) amazonensis kDNA 3 | L. (L.) mexicana | 81.2 |
| L. (L.) amazonensis kDNA 3 | L. (L.) tropica | 79 |
| L. (L.) major MSP associated gene 1 (L. major MAG 1) | L. (L.) chagasi | 83.2 |
| L. (L.) major MSP associated gene 1 (L. major MAG 1) | L. (L.) donovani | 81.65 |
| L. (L.) major MSP associated gene 1 (L. major MAG 1) | L. (L.) infantum | 83.6 |
| L. (L.) major MSP associated gene 1 (L. major MAG 1) | L. (L.) tropica | 82.5 |
| L. (L.) tropica Cytochrome B 4 | L. (L.) amazonensis | 69.7 |
| L. (L.) tropica Cytochrome B 4 | L. (L.) donovani | 69.4 |
| L. (L.) tropica Cytochrome B 4 | L. (L.) major | 71.3 |
| Mini-exon 1 | L. (L.) donovani | 79.6 |
| Mini-exon 1 | L. (L.) major | 78.45 |
| kDNA 1 minicircle | L. (L.) amazonensis | 79.3 |
| kDNA 1 minicircle | L. (L.) chagasi | 79.3 |
| kDNA 1 minicircle | L. (L.) donovani | 79.6 |
| kDNA 1 minicircle | L. (L.) infantum | 79.4 |
| kDNA 1 minicircle | L. (L.) major | 81.1 |
| kDNA 1 minicircle | L. (L.) mexicana | 80.9 |
| kDNA 1 minicircle | L. (L.) tropica | 78.5 |
| kDNA 3 minicircle | L. (L.) amazonensis | 79.5 |
| kDNA 3 minicircle | L. (L.) chagasi | 79.5 |
| kDNA 3 minicircle | L. (L.) donovani | 79.4 |
| kDNA 3 minicircle | L. (L.) infantum | 79.2 |
| kDNA 3 minicircle | L. (L.) major | 79.6 |
| kDNA 3 minicircle | L. (L.) mexicana | 80.7 |
| kDNA 3 minicircle | L. (L.) tropica | 79 |
| kDNA 3 minicircle | L. (V.) braziliensis | 78.7 |
| kDNA 4 minicircle | L. (L.) amazonensis | 78.2 |
| kDNA 4 minicircle | L. (L.) mexicana | 79.4 |

The embodiment above may be repeated until all Leishmania species of interest have been discriminated and/or examined. In using primer pairs common to all Leishmania species or a subset of Leishmania species, positive results obtained with a single primer pair along with the melting temperature of its double-stranded DNA product is in general not sufficient to establish presence of a particular Leishmania species in the sample; however, each common primer pair along with the melting temperature information of the double-stranded DNA product can be used to either exclude Leishmania species absent from the sample, and at the same time, to include Leishmania species possibly present in the sample. By repeating the same analysis with additional primer pairs shared by more than one Leishmania species, the process of excluding additional Leishmania species finally leads to narrowing of the subset of Leishmania possibly present in the sample and ultimately to one remaining Leishmania species as the particular Leishmania species present in the sample. Where available, the presence of this Leishmania species may be confirmed with a primer pair or primer pairs unique to the particular Leishmania species.

In accordance with the practice of the invention, the quantity of *Leishmania* in the sample may be determined by examining a single copy gene or a known copy gene number within a *Leishmania* species and comparing against a reference standard curve generated with different known amount of the particular *Leishmania* species. The quantity of *Leishmania* in the sample is measured relative to a standard curve from the same known *Leishmania* species. Generating a standard curve is well known in the art.

Alternatively, relative differences in the amount of *Leishmania* between samples may be determined with the primer pairs provided with the greatest sensitivity achieved using primer pairs directed towards multi-copy genes or kinetoplast DNAs (kDNAs either maxi-circle or mini-circle), using SYBR Green Dye I as a staining agent. Quantification as to the amount of *Leishmania* is desirable when monitoring a patient for changes in the level of *Leishmania* pathogens with or without a course of medicinal treatment. The patient sample so analyzed may be any material from a subject, including but not limited to skin, tissue, biopsied organ, bone marrow, bodily fluid, saliva, blood, and serum. The sample may be extracted for its nucleic acid content and/or further purified for RNA or DNA content. The sample may be free of host material, pure sample of *Leishmania*, or contain not only *Leishmania* material but also host material, such as *Leishmania* nucleic acid and e.g., human nucleic acid.

The subjects may include but are not limited to humans, monkeys, pigs, horses, cows, dogs and cats.

Known hosts for *Leishmania* include human and dog. Insect vectors include sand fly.

Examination of organisms not known to serve as a host or hosts known not to be infected by *Leishmania* can serve as negative controls for the methods described throughout this application.

*Leishmania* either in promastigote and/or amastigote stages of the *Leishmania* life cycle may be examined by the present methods.

In another embodiment, the method comprises (a) contacting the sample with a set of nucleic acid primer pairs with primer sequences unique to a particular *Leishmania* species, so as to make *Leishmania*-primer pair complexes; (b) exposing the complexes to a thermo-stable polymerase to produce double-stranded DNAs containing the primer sequences; (c) determining the time or number of temperature cycles at which a threshold level of double-stranded DNA product and/or pyrophosphate product is reached which is indicative of on-target specificity and/or quantity of *Leishmania* in the sample; and (d) identifying the particular *Leishmania* species by the unique primers used so as to thereby determine the presence, species, and/or quantity of *Leishmania* in the sample. In this embodiment, characterizing the double-stranded DNA product by its melting temperature is not necessary for identifying the particular *Leishmania* species but may be performed as a control to assure on-target specificity of the reaction.

In accordance with the practice of the invention, the quantity of *Leishmania* in the sample may be determined by examining a single copy gene or a known copy gene number within a *Leishmania* species and comparing against a reference standard curve generated with different known amount of the particular *Leishmania* species.

In yet another embodiment of the invention, the method comprises (a) contacting a sample with a nucleic acid primer having a complementary sequence so as to produce a complex; (b) contacting the sample with another nucleic acid primer having a different complementary sequence so as to produce a complex; (c) exposing the complexes to a thermo-stable polymerase so as to produce double stranded nucleic acid from the primers above; and (d) detecting the double stranded nucleic acid so produced, wherein the presence of the double stranded nucleic acid is indicative of the presence of *Leishmania* in the sample. Merely by way of example, the complementary nucleic acid sequences may have the 5' to 3' polarity such that the 3' end is directed toward each other to produce double-stranded nucleic acid corresponding to the primer pair.

In yet another embodiment, the method further comprises (e) contacting a sample with a third nucleic acid probe sequence modified at the 5' end with a detectable marker and at the 3' end with a quencher for the detectable marker. Proximity of the detectable marker to the quencher may permit fluorescence resonance energy transfer (FRET) between the quencher and the detectable marker, so as to lose or reduce the ability to detect a signal from the detectable marker. The third nucleic acid probe has a sequence complementary to a region bounded by the sequences in steps (a) and (b) above. The method further comprises (f) producing double stranded nucleic acid from the primers in (a) and (b) as in step (c). The method may optionally comprise forming primer-probe-*Leishmania* complexes and using a thermo-stable DNA polymerase with 5'-to-3' exonuclease activity, such as AmpliTaq® DNA polymerase, AmpliTaq Gold® DNA polymerase, or AmpliTaq Gold® DNA polymerase, LD, to permit double stranded nucleic acid synthesis from the primers in steps (a) and (b) and degradation of the probe encountered during the progression of the polymerase on the *Leishmania* DNA template. The method additionally comprises (g) detecting the detectable marker released from the third nucleic acid probe sequence. The excited detectable marker may no longer return to its ground state by transfer of energy to the quencher dye through FRET but rather may return to its ground state upon release of a photon with a longer wavelength. Detection of fluorescence from the released detectable marker may be indicative of the presence of *Leishmania* in the sample.

Examples of detectable markers include BioSearch Blue, acridine, coumarin, 6-carboxyfluorescein or FAM, rhodamine green, tetrachlorofluorescein or TET, tetramethylrhodamine (TAMRA), dihydrocyclopyrroloindole tripeptide (MGB), VIC, NED, CAL Fluor Gold 540 (Biosearch Technologies), JOE, HEX, CAL Fluor Orange 560, Quasar 570, Cy3, rhodamine red, CAL Fluor Red 590, Cy3.5, SuperROX (Biosearch Technologies), ROX, CAL Fluor Red 610, Texas Red, LC Red 640, CAL Fluor Red 635, Pulsar 650, Quasar 670, Quasar 705, Cy5, and Cy5.5.

Examples of a quencher for the detectable marker include tetramethylrhodamine or TAMRA as a quencher for FAM, Iowa Black as quencher for TET; BHQ (Biosearch Technologies)(e.g., BHQ-0, BHQ-1, BHQ-2 and BHQ-3) as quencher for FAM, CAL Fluor Gold 540, and SuperROX; and Dabcyl.

A preferred embodiment of the nucleic acid probe is a deoxyoligonucleotide with a detectable marker at the 5' end and/or with a quencher for the detectable marker at the 3' end. The detectable marker may be a fluorescent dye or non-fluorescent chemical entity, e.g., radioisotope, colorimetric compound, etc. The quencher may interfere or prevent the detection of a signal generated by a detectable marker. In the case of fluorescence as a mode of detection, the detectable marker may be a fluorescent dye and the quencher may be a second fluorescent dye or a non-fluorescent chemical entity so long as the quencher is able to accept the energy of the detectable marker returning from an excited energetic state to its ground energy state in a process termed fluorescence resonance energy transfer or FRET. By transferring energy to the quencher, photons that would normally be observed from the detectable marker, following excitation to a higher energetic state and subsequent return to ground energetic state, may be diminished or may no longer be observed. As the efficiency of FRET is dependent on distance between the donor (detectable marker) and acceptor (quencher), release of the detectable marker from the probe may greatly increase the distance between the donor and the acceptor and may result in the loss of FRET, thereby permitting the observance of the photons from the detectable marker.

Examples of nucleic acid primer pairs include but are not limited to GGGTAGGGGCGTTCTGC (SEQ ID NO:3) and CCCGGCCTATTTTACACCAACC (SEQ ID NO. 4) (e.g., referred to in some later examples as kDNA 3 mini-circle forward and reverse primers, respectively); GGGTGCAGAAATCCCGTTCA (SEQ ID NO:5) and CCCGGCCCTATTTTACACCA (SEQ ID NO:6) (e.g., referred to in some later examples as kDNA 4 mini-circle forward and reverse primers, respectively); GGGTAGGGGCGTTCTGC (SEQ ID NO. 1) and TACACCAACCCCCAGTTTGC (SEQ ID NO:2) (e.g., referred to in some later examples as kDNA 1 mini-circle forward and reverse primers, respectively); AATGGGTGCAGAAATCCCGTTC (SEQ ID NO:7) and CCACCACCCGGCCCTATTTTAC (SEQ ID NO. 8) (e.g., referred to in some later examples as kDNA 7 mini-circle forward and reverse primers, respectively); GGGTAGGGGCGTTCTGC (SEQ ID NO:13) and TACACCAACCCCCAGTTTGC (SEQ ID NO:14) (e.g., referred to in some later examples as L. amazonensis kDNA 3 forward and reverse primers, respectively); AGGAGGATGGCAAGCGGAAG (SEQ ID NO:43) and GCGACGGGTACAGGGAGTTG (SEQ ID NO:44) (e.g., referred to in some later examples as DNA polymerase 2 forward and reverse primers, respectively); CGAAACTTCCGGAACCTGTCTT (SEQ ID NO:45) and CACCACACGCACGCACAC (SEQ ID NO:46) (e.g., referred to in some later examples as mini-exon 1 forward and reverse primers, respectively); GTCGTTGTCCGTGTCGCTGT (SEQ ID NO:59) and CGCTGTGTGTGTCCGTGTGT (SEQ ID NO:60) (e.g., referred to in some later examples as L. major MSP associated gene 1 forward and reverse primers, respectively); GACGACGACGAGGAGGATGG (SEQ ID NO:61) and GCGACGGGTACAGGGAGTTG (SEQ ID NO:62) (e.g., referred to in some later examples as L. amazonensis DNA polymerase I forward and reverse primers, respectively); GAAGGTGCAGTCCCTCGTGT (SEQ ID NO:63) and CCTCCGTCTGCTTGCTCTTG (SEQ ID NO:64) (e.g., referred to in some later examples as HSP70-1 forward and reverse primers, respectively); and TCGAGATCGACGCGTTGTT (SEQ ID NO:65) and CCGCACAGCTCCTCGAA (SEQ ID NO:66) (e.g., referred to in some later examples as HSP70-4 forward and reverse primers, respectively); and/or combinations thereof. Additional primers are shown in Table 2.

Examples of nucleic acid probe sequence (also referred to as the third nucleic acid sequence) include but not limited to ACCCCCAGTTTCCCGCCCCG (SEQ ID NO:83); CCCCAGTTTCCCGCCCCGGA (SEQ ID NO:84); TGGCCTTGGGGCGTGCAAACTGG (SEQ ID NO:85); TCCTGGCGGGGGTTTTCGCT (SEQ ID NO:86); CCCATACCACCAAACGCAGCCCA (SEQ ID NO:87); CCATGTACGATGATGTCGTATTGAGGTCTAACA (SEQ ID NO:88); CTTTAGGTAGGGAGTTGTACTACGTTTTTTGACCT (SEQ ID NO:89); TGAGGGCATGGAGGAGGGCG (SEQ ID NO:90); TGGGGTCGAGCACCATGCCGCC (SEQ ID NO:91); CGGCAAGATTTTGGAAGCGCGCA (SEQ ID NO:92); TGCGCACTGCACTGTCGCCCCC_(SEQ_ID_NO:93); CGCTGAGAGCGAGGCAGGCACGC (SEQ ID NO:94); CCTTCCCAAACGCCTCCCCTGCCCC (SEQ ID NO:95); and CACCGCCTGGAGCCCTGGGGC (SEQ ID NO:96).

In a specific embodiment, the first nucleic acid sequence in step (a) is GGGTGCAGAAATCCCGTTCA (SEQ ID NO:5) (kDNA 4 mini-circle forward primer); the second nucleic acid sequence in step (b) is CCCGGCCCTATTTTACACCA (SEQ ID NO:6) (kDNA 4 mini-circle reverse primer); and the sequence of the third nucleic acid probe is ACCCCCAGTTTCCCGCCCCG (SEQ ID NO:83), labeled at its 5' end with e.g., FAM and/or its 3' end with e.g., TAMRA as shown in Table 2.

In a further specific embodiment for detecting the presence of *Leishmania braziliensis, Leishmania guyanensis* and/or *Leishmania panamensis*, the first nucleic acid sequence in step (a) may be TGCTATAAAAATCGTACCACCCGACA (SEQ ID NO:101) (*L. braziliensis* mini-circle kDNA 3 forward primer); the second nucleic acid sequence in step (b) may be GAACGGGGTTTCTGTATGCCATTT (SEQ ID NO:102) (*L. braziliensis* mini-circle kDNA 3 reverse primer); and the sequence of the third nucleic acid probe is TTGCAGAACGCCCCTACCCAGAGGC (SEQ ID NO:109), labeled at its 5' end with e.g., FAM and/or its 3' end with e.g., TAMRA.

In a further specific embodiment for detecting the presence of *Leishmania tropica, Leishmania donovani, Leishmania chagasi*, and/or *Leishmania infantum*, the first nucleic acid sequence in step (a) may be AGAGCGTGCCTTGGATTGTG (SEQ ID NO:49) (MSP-associated gene 1 forward primer); the second nucleic acid sequence in step (b) may be (SEQ ID NO:50) CGCTGCGTTGATTGCGTTG (MSP-associated gene 1 reverse primer); and the sequence of the third nucleic acid probe is (SEQ ID NO:93) TGCGCACTGCACTGTCGCCCCC, labeled at its 5' end with e.g., FAM and/or its 3' end with e.g., TAMRA.

In a further specific embodiment for detecting the presence of *Leishmania chagasi, Leishmania donovani, Leishmania infantum, Leishmania major, Leishmania mexicana*, and/or *Leishmania tropica*, the first nucleic acid sequence in step (a) may be (SEQ ID NO:99) CTTTTCTGGTCCTCCGGGTAGG (kDNA 5 minicircle forward primer); the second nucleic acid sequence in step (b) is CCACCCGGCCCTATTTTACACCAA (SEQ ID NO:100) (kDNA 5 minicircle reverse primer); and the sequence of the third nucleic acid probe in is TTTTCGCAGAACGCCCCTACCCGC (SEQ ID NO:110), labeled at its 5' end with e.g., FAM and/or its 3' end with e.g., TAMRA.

In a further specific embodiment for detecting the presence of *Leishmania chagasi, Leishmania donovani, Leishmania infantum*, and/or *Leishmania major*, the first nucleic acid sequence in step (a) is AATGGGTGCAGAAATCCCGTTC (SEQ ID NO:7) (kDNA 7 minicircle forward primer); the second nucleic acid sequence in step (b) is CCACCACCCGGCCCTATTTTAC (SEQ ID NO:8) (kDNA 7 minicircle reverse primer); and the sequence of the third nucleic acid probe is CCCCAGTTTCCCGCCCCGGA (SEQ ID NO:84), labeled at its 5' end with e.g., FAM and/or its 3' end with e.g., TAMRA.

In a further specific embodiment for detecting the presence of *Leishmania amazonensis, Leishmania major*, and/or *Leishmania mexicana*, the first nucleic acid sequence in step (a) is GGTAGGGGCGTTCTGCGAAT (SEQ ID NO:11) (*Leishmania amazonensis* kDNA 2 forward primer); the second nucleic acid sequence in step (b) is CCCGGCCTATTTTACACCAACC (SEQ ID NO:12) (*Leishmania amazonensis* kDNA 2 reverse primer); and the sequence of the third nucleic acid probe is TGGCCTTGGGGCGTGCAAACTGG (SEQ ID NO:85), labeled at its 5' end with e.g., FAM and/or its 3' end with e.g., TAMRA.

In a further specific embodiment for detecting the presence of *Leishmania chagasi*, the first nucleic acid sequence in step (a) is TCCGCAGGAGACTTCGTATG (SEQ ID NO:103) (*Leishmania infantum* minicircle 1 forward primer); the second nucleic acid sequence in step (b) is CACGACTATCCACCCCATCC (SEQ ID NO:104) (*Leishmania infantum* minicircle 1 reverse primer); and the sequence of the third nucleic acid probe is CTGAGAGACCCGCCGGGGCG (SEQ ID NO:111), labeled at its 5' end with e.g., FAM and/or its 3' end with e.g., TAMRA.

In a further specific embodiment for detecting the presence of *Leishmania tropica*, the first nucleic acid sequence in step (a) is GGGGGTTGGTGTAAAATAGGG (SEQ ID NO:23) (*Leishmania tropica* minicircle 1 forward primer); the second nucleic acid sequence in step (b) is ACCACCAGCAGAAGGTCAAAG (SEQ ID NO:24) (*Leishmania tropica* minicircle 1 reverse primer); and the sequence of the third nucleic acid probe is TCCTGGCGGGGGTTTTCGCT (SEQ ID NO:86), labeled at its 5' end with e.g., FAM and/or its 3' end with e.g., TAMRA.

In a further specific embodiment for detecting the presence of *Leishmania donovani*, the first nucleic acid sequence in step (a) is GCGGTGGCTGGTTTTAGATG (SEQ ID NO:25) (*Leishmania donovani* minicircle 1 forward primer); the second nucleic acid sequence in step (b) is TCCAATGAAGCCAAGCCAGT (SEQ ID NO:26) (*Leishmania donovani* minicircle 1 reverse primer); and the sequence of the third nucleic acid probe is CCCATACCACCAAACGCAGCCCA (SEQ ID NO:87), labeled at its 5' end with e.g., FAM and/or its 3' end with e.g., TAMRA.

In a further specific embodiment for detecting the presence of *Leishmania chagasi, Leishmania donovani*, and/or *Leishmania infantum*, the first nucleic acid sequence in step (a) is ATTTTAGTATGAGTGGTAGGTTTTGTT (SEQ ID NO:27) (cytochrome B 1 forward primer); the second nucleic acid sequence in step (b) is CAATAACTGGGACGGTTGCT (SEQ ID NO:28) (cytochrome B 1 reverse primer); and the sequence of the third nucleic acid probe is CCATGTACGATGATGTCGTATTGAGGTCTAACA (SEQ ID NO:88), labeled at its 5' end with e.g., FAM and/or its 3' end with e.g., TAMRA.

In a further specific embodiment for detecting the presence of *Leishmania chagasi, Leishmania donovani*, and/or *Leishmania info/1 mm*, the first nucleic acid sequence in step (a) is GCTTGGTTGGATTATTTTTGCTG (SEQ ID NO:39) (maxicircle 1 forward primer); the second nucleic acid sequence in step (b) is AACAACATTTTAACTCTTGTAGGATTCG (SEQ ID NO:40) (maxicircle 1 reverse primer); and the sequence of the third nucleic acid probe is CTTTAGGTAGGGAGTTGTAC-TACGTTTTTTGACCT (SEQ ID NO:89), labeled at its 5' end with e.g., FAM and/or its 3' end with e.g., TAMRA.

In a further specific embodiment for detecting the presence of *Leishmania amazonensis, Leishmania chagasi, Leishmania donovani, Leishmania infantum, Leishmania major, Leishmania mexicana*, and/or *Leishmania tropica*, the first nucleic acid sequence in step (a) is GAGGTGTTTGCCCGCATC (SEQ ID NO:41) (alpha-tubulin 1 forward primer); the second nucleic acid sequence in step (b) is CTCGCCCATGTCGTCG (SEQ ID NO:42) (alpha-tubulin 1 reverse primer); and the sequence of the third nucleic acid probe is TGAGGGCATGGAGGAGGGCG (SEQ ID NO:90), labeled at its 5' end with e.g., FAM and/or its 3' end with e.g., TAMRA.

In a further specific embodiment for detecting the presence of *Leishmania amazonensis, Leishmania chagasi, Leishmania donovani, Leishmania infantum, Leishmania major, Leishmania mexicana*, and/or *Leishmania tropica*, the first nucleic acid sequence in step (a) is TGTCGCTTGCAGACCAGATG (SEQ ID NO:105) (DNA polymerase 1 forward primer); the second nucleic acid sequence in step (b) is GCATCGCAGGTGTGAGCA (SEQ ID NO:106) (DNA polymerase 1 reverse primer); and the sequence of the third nucleic acid probe is CAGCAACAACTTCGAGCCTGGCACC (SEQ ID NO:112), labeled at its 5' end with e.g., FAM and/or its 3' end with e.g., TAMRA.

In a further specific embodiment for detecting the presence of *Leishmania amazonensis, Leishmania braziliensis, Leishmania chagasi, Leishmania donovani, Leishmania infantum, Leishmania major, Leishmania mexicana*, and/or *Leishmania tropica*, the first nucleic acid sequence in step (a) is AGGAGGATGGCAAGCGGAAG (SEQ ID NO:43) (DNA polymerase 2 forward primer); the second nucleic acid sequence in step (b) is GCGACGGGTACAGGGAGTTG (SEQ ID NO:44) (DNA polymerase 2 reverse primer); and the sequence of the third nucleic acid probe is TGGGGTCGAGCACCATGCCGCC (SEQ ID NO:91), labeled at its 5' end with e.g., FAM and/or its 3' end with e.g., TAMRA.

In a further specific embodiment for detecting the presence of *Leishmania amazonensis, Leishmania chagasi, Leishmania donovani, Leishmania infantum, Leishmania major*, and/or *Leishmania tropica*, the first nucleic acid sequence in step (a) is CGAAACTTCCGGAACCTGTCTT (SEQ ID NO:45) (mini-exon 1 forward primer); the second nucleic acid sequence in step (b) is CACCACACGCACGCACAC (SEQ ID NO:46) (mini-exon 1 reverse primer); and the sequence of the third nucleic acid probe is CGGCAAGATTTTGGAAGCGCGCA (SEQ ID NO:92), labeled at its 5' end with e.g., FAM and/or its 3' end with e.g., TAMRA.

In a further specific embodiment for detecting the presence of *Leishmania chagasi, Leishmania donovani*, and/or *Leishmania infantum*, the first nucleic acid sequence in step (a) is AGTTTTGGTTGGCGCTCCTG (SEQ ID NO:51) (MSP-associated gene 2 (MAG 2) forward primer); the second nucleic acid sequence in step (b) is CCCACTCGCTTTCCTTGGTC (SEQ ID NO:52) (MSP-associated gene 2 (MAG 2) reverse primer); and the sequence of the third nucleic acid probe is CGCTGAGAGCGAGGCAGGCACGC (SEQ ID NO:94), labeled at its 5' end with e.g., FAM and/or its 3' end with e.g., TAMRA.

In one embodiment of the invention, the nucleic acid probe sequence is different from the nucleic acid primers of steps (a) and (b) and includes but is not limited to any of ACCCCCAGTTTCCCGCCCCG (SEQ ID NO:83) (e.g., referred to in some later examples as kDNA 4 mini-circle probe), CCCCAGTTTCCCGCCCCGGA (SEQ ID NO:84) (e.g., referred to in some later examples as kDNA 7 mini-circle probe), TGGGGTCGAGCACCATGCCGCC (SEQ ID NO:91) (e.g., referred to in some later examples as DNA polymerase 2 probe), and CGGCAAGATTTTG-GAAGCGCGCA (SEQ ID NO:92) (e.g., referred to in some later examples as mini-exon 1 probe), labeled at their 5' end with e.g., FAM and their 3' end with e.g., TAMRA.

Suitable examples of the quenchable detectable marker e.g., a fluorescent reporter dye include but are not limited to 6-carboxyfluorescein (FAM), tetrachlorofluorescein (TET), tetramethylrhodamine (TAMRA), dihydrocyclopyrroloindole tripeptide (MGB), VIC, NED, CAL Fluor Gold 540 (Biosearch Technologies), SuperROX (Biosearch Technologies), BioSearch Blue, acridine, coumarin, rhodamine green, JOE, HEX, CAL Fluor Orange 560, Quasar 570, Cy3, rhodamine red, CAL Fluor Red 590, Cy3.5, ROX, CAL Fluor Red 610, Texas Red, LC Red 640, CAL Fluor Red 635, Pulsar 650, Quasar 670, Quasar 705, Cy5 and Cy5.5.

Suitable examples of the quencher for detectable marker include but not limited to tetramethylrhodamine (TAMRA), Black Hole Quencher (BHQ; Biosearch Technologies) (e.g., BHQ-0, BHQ-1, BHQ-2 and BHQ-3), Dabcyl and Iowa Black. In one embodiment, the fluorescent reporter dye may be detected by fluorescence.

The invention further provides a method for determining the presence of Leishmania braziliensis in a sample from a subject infected with Leishmania. The method comprises (a) contacting the sample with a primer X1 so as to produce a complex; (b) contacting the sample with a primer Y1 so as to produce a complex; (c) producing double stranded nucleic acid from the primers in steps (a) and (b); and (d) detecting the double-stranded DNA so produced, the presence of double-stranded DNA is indicative of the presence of a Leishmania species Leishmania braziliensis. In the method, primer X1 so selected is different from primer Y1.

Examples of primers X1 and Y1, include but are not limited to AATTTCGCAGAACGCCCCTAC (SEQ ID NO:17) (L. braziliensis kDNA 1 forward primer) and GTACTCCCCGACATGCCTCTG (SEQ ID NO:18) (L. braziliensis kDNA 1 reverse primer); and, TGC-TATAAAATCGTACCACCCGACA (SEQ ID NO:101) (L. braziliensis kDNA 3 forward primer) and GAACGGGGTTTCTGTATGCCATTT (SEQ ID NO:102) (L. braziliensis kDNA 3 reverse primer); GGGTAGGGGCGTTCTGC (SEQ ID NO:3) and CCCGGCCTATTTTACACCAACC (SEQ ID NO:4) (kDNA 3 mini-circle forward and reverse primers, respectively); and GGGTGCAGAAATCCCGTTCA (SEQ ID NO:5) and CCCGGCCCTATTTTACACCA (SEQ ID NO:6) (kDNA 4 mini-circle forward and reverse primers, respectively); GGGTAGGGGCGTTCTGC (SEQ ID NO:1) and TACACCAACCCCCAGTTTGC (SEQ ID NO:2) (kDNA 1 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (L. amazonensis kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (L. major MSP associated gene 1 forward and reverse primers, respectively); GACGACGACGAGGAGGATGG (SEQ ID NO:61) and GCGACGGGTACAGGGAGTTG (SEQ ID NO:62) (L. amazonensis DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); TCGAGATCGACGCGTTGTT (SEQ ID NO:65) and CCGCACAGCTCCTCGAA (SEQ ID NO:66) (HSP70-4 forward and reverse primers, respectively); and GGAGAAACTCACGGCACAGG (SEQ ID NO:67) and GCGCCTCGTAGGTCACAGTT (SEQ ID NO:68) (SLACS forward and reverse primers, respectively); and/or combinations thereof.

In one embodiment of the invention, the melting temperature of the double-stranded DNA so produced for L. (V.) braziliensis DNA polymerase 2 forward primer and L. (V.) braziliensis DNA polymerase 2 reverse primer is a melting temperature that is approximately 1.5 to 2° C. below the melting temperature of the double-stranded DNA molecule produced using the same primers to amplify DNA from L. amazonensis, L. chagasi, L. donovani, L. infantum, L. major, L. mexicana or L. tropica, when assayed in the same salt, buffer, pH, volume and template conditions in presence of SYBR Green Dye I. Melt temperatures of other SYBR green assays can also be used for distinguishing between species, as illustrated in Table 7.

Additionally, the invention provides a method for determining the presence of Leishmania tropica in a sample. The method comprises contacting the sample with a primer X2 so as to produce a complex; contacting the sample with a primer Y2 so as to produce a complex; producing double stranded nucleic acid from the primers X2 and Y2; and detecting the double-stranded DNA so produced. The presence of double-stranded DNA is indicative of the presence of a Leishmania species Leishmania tropica.

Examples of primers X2 and Y2, include but are not limited to GGGTAGGGGCGTTCTGC (SEQ ID NO:1) and TACACCAACCCCCAGTTTGC (SEQ ID NO:2) (kDNA 1 mini-circle forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (L. amazonensis kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (L. major MSP associated gene 1 forward and reverse primers, respectively); GACGACGACGAGGAG-GATGG (SEQ ID NO:61) and GCGACGGGTACAGG- GAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); and/or a combination thereof. Further, the double-stranded DNA so produced by kDNA 1 mini-circle forward primer and kDNA 1 mini-circle reverse primer may have a lower melting temperature for the *Leishmania tropica* than the melting temperature of the double-stranded DNA so produced from *Leishmania mexicana, Leishmania major, Leishmania tropica, Leishmania amazonensis, Leishmania chagasi, Leishmania infantum,* or *Leishmania donovani.*

In one embodiment of the invention, the melting temperature of the double-stranded DNA so produced by kDNA 1 mini-circle forward primer and kDNA 1 mini-circle reverse primer for *Leishmania tropica* is a melting temperature about 0.4° C. to 1.5° C. lower than for *Leishmania amazonensis, Leishmania chagasi, Leishmania infantum,* or *Leishmania donovani* and/or 2.0° C. to 3.1° C. lower than for *Leishmania mexicana* or *Leishmania major,* e.g., as assayed in the presence of SYBR Green Dye I.

In another embodiment, the melting temperature of the double-stranded DNA so produced for kDNA 1 minicircle forward primer and kDNA 1 minicircle reverse primer has a melting temperature that is approximately 1° C. below the melting temperature of the double-stranded DNA molecule produced from the reaction of the same primers with DNA from *L. donovani, L. chagasi, L. infantum,* and/or *L. amazonensis* DNA, and/or approximately 2° C. below the melting temperature of the double-stranded DNA molecule produced when the same primers are used to amplify *L. mexicana* or *L. major* DNA, when assayed in the same salt, buffer, pH, volume and template conditions in presence of SYBR Green Dye I. Melt temperatures of other SYBR green assays can also be used for distinguishing between species, as illustrated in Table 7.

The invention also provides a method for determining the presence of *Leishmania mexicana* in a sample from a subject infected with *Leishmania*. This method comprises (a) contacting the sample with a primer X3 so as to produce a complex; (b) contacting the sample with a primer Y3 so as to produce a complex; (c) producing double stranded nucleic acid from the primers in (a) and (b); and (d) detecting the double-stranded DNA so produced. The presence of double-stranded DNA is indicative of the presence of a *Leishmania* species *Leishmania mexicana*.

Examples of primers X3 and Y3 include but are not limited to any of GGGTAGGGGCGTTCTGC (SEQ ID NO:1) and TACACCAACCCCCAGTTTGC (SEQ ID NO:2) (kDNA 1 mini-circle forward and reverse primers, respectively); AATGCGAGTGTTGCCCTTTTG (SEQ ID NO:21) and GCCGAACAACGCCATATTAACC (SEQ ID NO:22) (*L. mexicana* mini-circle 1 forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (*L. major* MSP associated gene 1 forward and reverse primers, respectively); GACGACGACGAGGAGGATGG (SEQ ID NO:61) and GCGACGGGTACAGGGAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); and/or a combination thereof.

In an embodiment of the invention, the double-stranded DNA so produced by kDNA 1 mini-circle forward primer and kDNA 1 mini-circle reverse primer has a similar melting temperature for *Leishmania mexicana* as the melting temperature of the double-stranded DNA so produced from *Leishmania major* but a higher melting temperature for *Leishmania mexicana* than the melting temperature of the double-stranded DNA so produced from *Leishmania tropica, Leishmania amazonensis, Leishmania chagasi, Leishmania infantum,* or *Leishmania donovani.*

In another embodiment, double-stranded DNA is so produced by *L. mexicana* mini-circle 1 forward and reverse primers for *Leishmania mexicana.*

In another embodiment, the melting temperature of the double-stranded DNA so produced by kDNA 1 mini-circle forward primer and kDNA 1 mini-circle reverse primer for *Leishmania mexicana* is a melting temperature about e.g., 1.5±0.4° C. higher than that of *Leishmania donovani, Leishmania amazonensis, Leishmania infantum* or *Leishmania chagasi,* or about 2.6±0.4° C. higher than that of *Leishmania tropica,* e.g., as assayed in the presence of SYBR Green Dye I.

In another embodiment, the melting temperature of the double-stranded DNA so produced for *L. (L.) amazonensis* kDNA 1 forward primer and *L. (L.) amazonensis* kDNA 1 reverse primer is a melting temperature that is approximately 1-2° C. above the melting temperature of the double-stranded DNA molecule produced from a reaction using the same primers to amplify *L. amazonensis* or *L. major* DNA, assayed in the same salt, buffer, pH, volume and template conditions in presence of SYBR Green Dye I. Melt temperatures of other SYBR green assays can also be used for distinguishing between species, as illustrated in Table 7.

The invention further provides a method for determining the presence of *Leishmania major* in a sample from a subject infected with *Leishmania*. This method comprises (a) contacting the sample with a primer X4 so as to produce a complex; (b) contacting the sample with a primer Y4 so as to produce a complex; (c) contacting the sample with a primer X5 so as not to produce a complex; (d) contacting the sample with a primer Y5 so as not to produce a complex; (e) producing double stranded nucleic acid from the primers in (a) and (b) but not from the primers in (c) and (d); and (f) detecting the double-stranded DNA so produced from the primers in (a) and (b). The presence of double-stranded DNA from the primers in (a) and (b) but not the primers in (c) and (b), is indicative of the presence of a *Leishmania* species *Leishmania major*.

Examples of primers X4 and Y4 include but are not limited to any of, GGGTAGGGGCGTTCTGC (SEQ ID NO:1) and TACACCAACCCCCAGTTTGC (SEQ ID NO:2) (kDNA 1 mini-circle forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) nd CGCTGTGTGTGTCCGTGTGT (SEQ ID NO:60) (*L. major* MSP associated gene 1 forward and reverse primers, respectively); GACGACGACGAGGAGGATGG (SEQ ID NO:61) and GCGACGGGTACAGGGAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); and/or combinations thereof.

Examples of primers X5 and Y5 may include AATGCGAGTGTTGCCCTTTTG (SEQ ID NO:21) and GCCGAACAACGCCATATTAACC (SEQ ID NO:22) (*L. mexicana* mini-circle 1 forward and reverse primers respectively).

In one embodiment, the double-stranded DNA so produced by kDNA 1 mini-circle forward primer and kDNA 1 mini-circle reverse primer has about a similar melting temperature for *Leishmania major* as the double-stranded DNA so produced from *Leishmania mexicana* but a higher melting temperature for *Leishmania major* than the double-stranded DNA so produced from *Leishmania tropica, Leishmania amazonensis, Leishmania chagasi, Leishmania infantum*, or *Leishmania donovani*.

In another embodiment, the melting temperature of the double-stranded DNA so produced by kDNA 1 mini-circle forward primer and kDNA 1 mini-circle reverse primer for *Leishmania major* is a melting temperature about e.g. 1.5±0.4° C. higher than that of *Leishmania donovani, Leishmania amazonensis, Leishmania infantum* or *Leishmania chagasi*, or about 2.6±0.4° C. higher than that of *Leishmania tropica*, e.g., as assayed in the presence of SYBR Green Dye I.

In another embodiment, the melting temperature of the double-stranded DNA so produced for *L. (L.) amazonensis* kDNA 2 forward primer and *L. (L.) amazonensis* kDNA 2 reverse primer is a melting temperature that is approximately 1 or 2° C. below the melting temperature of the double-stranded DNA molecule produced from a reaction using the same primers to amplify *L. amazonensis, L. mexicana* or *L. infantum* DNA, assayed in the same salt, buffer, pH, volume and template conditions in presence of SYBR Green Dye I. Melt temperatures of other SYBR green assays can also be used for distinguishing between species, as illustrated in Table 7.

The invention additionally provides a method for determining the presence of whether a subject is infected with *Leishmania amazonensis*. The method comprises (a) contacting the sample with a primer X6 so as to produce a complex; (b) contacting the sample with a primer Y6 so as to produce a complex; (c) producing double stranded nucleic acid from the primers in (a) and (b); and (d) detecting for the double-stranded DNA so produced. The presence of double-stranded DNA or absence of double-stranded DNA is indicative of the presence of a *Leishmania* species *Leishmania amazonensis*.

Examples of primers X6 and Y6 include but are not limited to any of GGGTAGGGGCGTTCTGC (SEQ ID NO:1) and TACACCAACCCCCAGTTTGC (SEQ ID NO:2) (kDNA 1 mini-circle forward and reverse primers, respectively); GGTAGGGGCGTTCTGCGAAT (SEQ ID NO:11) and CCCGGCCTATTTTACACCAACC (SEQ ID NO:12) (*L. amazonensis* kDNA 2 forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (*L. major* MSP associated gene 1 forward and reverse primers, respectively); GACGACGACGAGGAGGATGG (SEQ ID NO:61) and GCGACGGGTACAGGGAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); TCGAGATCGACGCGTTGTT (SEQ ID NO:65) and CCGCACAGCTCCTCGAA (SEQ ID NO:66) (HSP70-4 forward and reverse primers, respectively); and AGAGCGTGCCTTGGATTGTG (SEQ ID NO:49) and CGCTGCGTTGATTGCGTTG (SEQ ID NO:50) (MSP-associated gene 1 forward and reverse primers, respectively); and/or, combinations thereof.

In another embodiment, the double-stranded DNA so produced by kDNA 1 mini-circle forward primer and kDNA 1 mini-circle reverse primer has a similar melting temperature for *Leishmania amazonensis* as the double-stranded DNA so produced from *Leishmania chagasi, Leishmania infantum*, and/or *Leishmania donovani* but a lower melting temperature for *Leishmania amazonensis* than the melting temperature of the double-stranded DNA so produced from *Leishmania major* and/or *Leishmania mexicana*, and a higher melting temperature for *Leishmania amazonensis* than the melting temperature of the double-stranded DNA so produced from *Leishmania tropica*.

In another embodiment, the double-stranded DNA is so produced by *L. amazonensis* kDNA 2 forward primer and *L. amazonensis* kDNA 2 reverse primer for the *L. amazonensis, L. donovani, L. infantum, L. major* or *L. mexicana* but not *L. braziliensis, L. chagasi* or *L. tropica*.

In another embodiment, the double-stranded DNA is so produced by MSP-associated gene 1 forward primer and MSP-associated gene 1 reverse primer for the *L. chagasi, L. donovani, L. infantum*, or *L. tropica* but not *L. amazonensis, L. braziliensis, L. major*, or *L. mexicana*.

In a further embodiment, the melting temperature of the double-stranded DNA so produced by kDNA 1 mini-circle forward primer and kDNA 1 mini-circle reverse primer for *Leishmania amazonensis* is a melting temperature about e.g., 1.5±0.4° C. lower than that of *Leishmania major* or *Leishmania mexicana* or 1.0±0.4° C. higher than that of *Leishmania tropica*, e.g., as assayed in the presence of SYBR Green Dye I.

In another embodiment, the melting temperature of the double-stranded DNA so produced for HSP70-4 forward primer and HSP70-4 reverse primer is a melting temperature that is approximately 1-2° C. below the melting temperature of the double-stranded DNA molecule produced from a reaction using the same primers to amplify DNA from *L. donovani, L. mexicana, L. braziliensis* or *L. tropica*, assayed in the same salt, buffer, pH, volume and template conditions in presence of SYBR Green Dye I. Melt temperatures of other SYBR green assays can also be used for distinguishing between species, as illustrated in Table 7.

Moreover, the invention also provides a method for determining the presence of whether a subject is infected with the *Leishmania chagasi* and/or *Leishmania infantum*. The method comprises contacting the sample with a primer X7 so as to produce a complex; contacting the sample with a primer Y7 so as to produce a complex; producing double stranded nucleic acid from the X7 and Y7 primers; and detecting the double-stranded DNA so produced. The presence of double-stranded DNA with a characteristic melting temperature is indicative of the presence of a *Leishmania* species *Leishmania chagasi* and/or *Leishmania infantum*. In one example, the melting temperature may be about 1.5±0.4° C. lower than that of *Leishmania major* or *Leishmania mexicana* or 1.0±0.4° C. higher than that of *Leishmania tropica*, e.g., as assayed in the presence of SYBR Green Dye I. In another example, the melting temperature of the double-stranded DNA so produced by MSP-associated gene 1 forward primer and MSP-associated gene 1 reverse primer for *Leishmania chagasi* and *Leishmania infantum* is a melting temperature about e.g. 2.1±0.4° C. higher than that of *Leishmania donovani*, e.g., as assayed in the presence of SYBR Green Dye I.

In another embodiment, the melting temperature of the double-stranded DNA so produced for MAG1 forward primer and MAG1 reverse primer is a melting temperature that is approximately 1 or 2° C. above the melting temperature of the double-stranded DNA molecule produced from a reaction using the same primers to amplify *L. tropica* or *L. donovani*, but the same as the melting temperature of the double-stranded DNA molecule produced from a reaction using the same primers to amplify *L. infantum* DNA, assayed in the same salt, buffer, pH, volume and template conditions in presence of SYBR Green Dye I. Melt temperatures of other SYBR green assays can also be used for distinguishing between species, as illustrated in Table 7.

In another embodiment, the melting temperature of the double-stranded DNA so produced for MAG1 forward primer and MAG1 reverse primer is a melting temperature that is approximately 1 or 2° C. above the melting temperature of the double-stranded DNA molecule produced from a reaction using the same primers to amplify *L. tropica* or *L. donovani*, but the same as the melting temperature of the double-stranded DNA molecule produced from a reaction using the same primers to amplify *L. chagasi* DNA, assayed in the same salt, buffer, pH, volume and template conditions in presence of SYBR Green Dye I. Melt temperatures of other SYBR green assays can also be used for distinguishing between species, as illustrated in Table 7.

The primers X7 and Y7 include but are not limited to any of GGGTAGGGGCGTTCTGC (SEQ ID NO:1) and TACACCAACCCCCAGTTTGC (SEQ ID NO:2) (kDNA 1 mini-circle forward and reverse primers, respectively); AGAGCGTGCCTTGGATTGTG (SEQ ID NO:49) and CGCTGCGTTGATTGCGTTG (SEQ ID NO:50) (MSP-associated gene 1 forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (*L. major* MSP associated gene 1 forward and reverse primers, respectively); GACGACGACGAGGAG-GATGG (SEQ ID NO:61) and GCGACGGGTACAGG-GAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); and/or combinations thereof.

In one embodiment, the double-stranded DNA so produced by kDNA 1 mini-circle forward primer and kDNA 1 mini-circle reverse primer has a similar melting temperature for *Leishmania chagasi* and/or *Leishmania infantum* as the double-stranded DNA so produced from *Leishmania amazonensis* and/or *Leishmania donovani* but a lower melting temperature for *Leishmania chagasi* and/or *Leishmania infantum* than the melting temperature of the double-stranded DNA so produced from *Leishmania major* and/or *Leishmania mexicana*, and a higher melting temperature for *Leishmania chagasi* and/or *Leishmania infantum* than the melting temperature of the double-stranded DNA so produced from *Leishmania tropica*; and wherein the double-stranded DNA so produced by MSP-associated gene 1 forward primer and MSP-associated gene 1 reverse primer has a higher melting temperature for *Leishmania chagasi* and/or *Leishmania infantum* than the melting temperature of the double-stranded DNA so produced from *Leishmania donovani*.

The invention additionally provides a method for determining the presence of whether a sample contains *Leishmania donovani*. The method comprises contacting the sample with a primer X8 so as to produce a complex; contacting the sample with a primer Y8 so as to produce a complex; producing double stranded nucleic acid from the primers X8 and Y8; and detecting the double-stranded DNA so produced. The presence of double-stranded DNA with a characteristic melting temperature is indicative of the presence of a *Leishmania* species *Leishmania donovani*.

In one embodiment, the double-stranded DNA so produced by kDNA 1 mini-circle forward primer and kDNA 1 mini-circle reverse primer has a similar melting temperature for *Leishmania donovani* as the double-stranded DNA so produced from *Leishmania amazonensis, Leishmania chagasi*, and/or *Leishmania infantum* but a lower melting temperature for *Leishmania donovani* than the melting temperature of the double-stranded DNA so produced from *Leishmania major* and/or *Leishmania mexicana*, and a higher melting temperature for *Leishmania donovani* than the melting temperature of the double-stranded DNA so produced from *Leishmania tropica*.

In another embodiment, the double-stranded DNA so produced by MSP-associated gene 1 forward primer and MSP-associated gene 1 reverse primer has a lower melting temperature for *Leishmania donovani* than the melting temperature of the double-stranded DNA so produced from *Leishmania chagasi* and/or *Leishmania infantum*.

In one example, the melting temperature of the double-stranded DNA so produced by kDNA 1 mini-circle forward primer and kDNA 1 mini-circle reverse primer for *Leishmania donovani* is a melting temperature about e.g., 1.5±0.4° C. lower than that of *Leishmania major* or *Leishmania mexicana* or 1.0±0.4° C. higher than that of *Leishmania tropica*, e.g., as assayed in the presence of SYBR Green Dye I. In another example, the melting temperature of the double-stranded DNA so produced by MSP-associated gene 1 forward primer and MSP-associated gene 1 reverse primer for *Leishmania donovani* is a melting temperature about e.g., 2.1±0.4° C. lower than that of *Leishmania infantum* or *Leishinani chagasi*, e.g., as assayed in the presence of SYBR Green Dye I.

In another embodiment, the melting temperature of the double-stranded DNA so produced for MAG1 forward primer and MAG1 reverse primer is a melting temperature that is approximately 1 or 2° C. below the melting temperature of the double-stranded DNA molecule produced from a reaction using the same primers to amplify *L. tropica, L. chagasi* or *L. infantum* DNA, assayed in the same salt, buffer, pH, volume and template conditions in presence of SYBR Green Dye I. Melt temperatures of other SYBR green assays can also be used for distinguishing between species, as illustrated in Table 7.

Examples of primers X8 and Y8 include but are not limited to any of GGGTAGGGGCGTTCTGC (SEQ ID NO:1) and TACACCAACCCCCAGTTTGC (SEQ ID NO:2) (kDNA 1 mini-circle forward and reverse primers, respectively); AGAGCGTGCCTTGGATTGTG (SEQ ID NO:49) and CGCTGCGTTGATTGCGTTG (SEQ ID NO:50) (MSP-associated gene 1 forward and reverse primers, respectively); GGGTAGGGGCGTTCTGC (SEQ ID NO:3) and CCCGGCCTATTTTACACCAACC (SEQ ID NO:4) (kDNA 3 mini-circle forward and reverse primers, respectively); GGGTGCAGAAATCCCGTTCA (SEQ ID NO:5) and CCCGGCCCTATTTTACACCA (SEQ ID NO:6) (kDNA 4 mini-circle forward and reverse primers, respectively); AATGGGTGCAGAAATCCCGTTC (SEQ ID NO:7) and CCACCACCCGGCCCTATTTTAC (SEQ ID NO:8) (kDNA 7 mini-circle forward and reverse primers, respectively); GGGTAGGGGCGTTCTGC (SEQ ID NO:13) and TACACCAACCCCCAGTTTGC (SEQ ID NO:14) (*L. amazonensis* kDNA 3 forward and reverse primers, respectively); AGGAGGATGGCAAGCGGAAG (SEQ ID NO:43) and GCGACGGGTACAGGGAGTTG (SEQ ID NO:44) (DNA polymerase 2 forward and reverse primers, respectively); CGAAACTTCCGGAACCTGTCTT (SEQ ID NO:45) and CACCACACGCACGCACAC (SEQ ID NO:46) (mini-exon 1 forward and reverse primers, respectively); GTCGTTGTCCGTGTCGCTGT (SEQ ID NO:59) and CGCTGTGTGTGTCCGTGTGT (SEQ ID NO:60) (*L. major* MSP associated gene 1 forward and reverse primers, respectively); GACGACGACGAGGAGGATGG (SEQ ID NO:61) and GCGACGGGTACAGGGAGTTG (SEQ ID NO:62) (*L. amazonensis* DNA polymerase I forward and reverse primers, respectively); GAAGGTGCAGTCCCTCGTGT (SEQ ID NO:63) and CCTCCGTCTGCTTGCTCTTG (SEQ ID NO:64) (HSP70-1 forward and reverse primers, respectively); and TCGAGATCGACGCGTTGTT (SEQ ID NO:65) and CCGCACAGCTCCTCGAA (SEQ ID NO:66) (HSP70-4 forward and reverse primers, respectively); and/or a combination thereof.

The invention additionally provides a method for determining the presence of whether a sample contains *Leishmania guyanensis, Leishmania panamensis*, and/or *Leishmania braziliensis*, and/or a combination thereof. The method comprises contacting the sample with a primer X9 so as to produce a complex; contacting the sample with a primer Y9 so as to produce a complex; exposing the complexes to a thermo-stable polymerase to produce double stranded nucleic acid from the primers X9 and Y9; and detecting the double-stranded DNA so produced. The presence of double-stranded DNA is indicative of the presence of a *Leishmania* species *Leishmania guyanensis, Leishmania panamensis*, and/or *Leishmania braziliensis* or a combination thereof.

Examples of primers X9 and Y9 include but are not limited to any of AATTTCGCAGAACGCCCCTAC (SEQ ID NO:17) and GTACTCCCCGACATGCCTCTG (SEQ ID NO:18) (*L. braziliensis* kDNA 1 forward and reverse primers, respectively); and TGCTATAAAATCGTACCACCCGACA (SEQ ID NO:101) and GAACGGGGTTTCTGTATGCCATTT (SEQ ID NO:102) (*L. braziliensis* kDNA 3 forward and reverse primers, respectively).

In one embodiment, the double-stranded DNA so produced by kDNA 1 mini-circle forward primer and kDNA 1 mini-circle reverse primer has a similar melting temperature for *Leishmania donovani* as the double-stranded DNA so produced from *Leishmania amazonensis, Leishmania chagasi*, and/or *Leishmania infantum* but a lower melting temperature for *Leishmania donovani* than the melting temperature of the double-stranded DNA so produced from *Leishmania major* and/or *Leishmania mexicana*, and a higher melting temperature for *Leishmania donovani* than the melting temperature of the double-stranded DNA so produced from *Leishmania tropica*; and wherein the double-stranded DNA so produced by MSP-associated gene 1 forward primer and MSP-associated gene 1 reverse primer has a lower melting temperature for *Leishmania donovani* than the melting temperature of the double-stranded DNA so produced from *Leishmania chagasi* and/or *Leishmania infantum*.

In one embodiment, the invention also provides a method for determining in a sample the presence of *Leishmania guyanensis* or *Leishmania panamensis*, and/or combination thereof. But absence of *Leishmania braziliensis* in the same sample, which requires the methods of the invention, wherein primers X9 and Y9 produced double-stranded DNAs but primers X1 and Y1 failed to produce a double-stranded DNA.

In one embodiment, the invention provides a method for determining the presence, quantity and/or species of *Leishmania* in a sample. The method comprises (a) contacting the sample with a set of nucleic acid primer pairs with primer sequences common to all *Leishmania* species or to a subset of *Leishmania* species, so as to make *Leishmania*-primer pair complexes; (b) contacting the sample with a set of nucleic acid probe or probes modified with a quenchable detectable marker and a quencher for the detectable marker and having a sequence complementary to a region bounded by each primer pair in (a); (c) exposing the complexes to a thermo-stable polymerase to produce multiple double-stranded DNAs containing the primer sequences; (d) detecting the presence and/or rate of release of the detectable marker from the modified nucleic acid in (b), which is indicative of quantity and/or particular *Leishmania* species; thereby determining the presence, quantity and/or species of *Leishmania* in the sample. The steps in (a) to (d) above are repeated until all *Leishmania* species of interest have been discriminated and examined.

In another embodiment for determining the presence, quantity and/or species of *Leishmania* in a sample, the method comprises (a) contacting the sample with a set of nucleic acid primer pairs with primer sequences unique to a particular *Leishmania* species, so as to make *Leishmania*-primer pair complexes; (b) contacting the sample with a set of nucleic acid probe or probes modified with a quenchable detectable marker and a quencher for the detectable marker and having a sequence complementary to a region bounded by each primer pair in (a); (c) exposing the complexes to a thermo-stable polymerase to produce multiple double-stranded DNAs containing the primer sequences; (d) detecting the presence and/or rate of release of the detectable marker from the modified nucleic acid in (b), which is indicative of quantity and/or presence of *Leishmania* in the sample; and (e) identifying the particular *Leishmania* species by the unique primers used; thereby determining the presence, quantity and/or species of *Leishmania* in the sample.

In another embodiment, the invention provides a method for increasing throughput of analyzing the presence of *Leishmania* nucleic acid in a sample requiring simultaneous use of more than one method from the list of methods of the invention. The quenchable detectable markers have distinct fluorescent spectrum, thereby allowing one detectable marker associated with one method to be distinguished from other detectable marker or markers associated with other method or methods, respectively.

The invention also provides a method for determining whether a subject is suffering from a *Leishmania* infection by detecting the presence of *Leishmania* in a sample from the subject by the methods of the invention.

Kits

According to another aspect of the invention, kits are provided. Kits according to the invention include package(s) comprising the compositions of the invention.

The phrase "package" means any vessel containing compounds or compositions presented herein. In preferred embodiments, the package can be a box or wrapping. Packaging materials for use in packaging pharmaceutical products are well known to those of skill in the art. See, e.g., U.S. Pat. No. 5,323,907. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for using the diagnostic agents used in the present invention. Kits may also comprise instructions for approved uses of diagnostic agents herein by regulatory agencies, such as the United States Food and Drug Administration. Kits may optionally contain labeling or product inserts for the diagnostic agents useful in the invention. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other agents for use in diagnosis as described herein. Such agents include but are not limited to any thermo-stable enzyme as described above.

The kit can be directed towards the more prevalent *Leishmania* species endemic to a particular geographical area, such as that given in Table 5.

The kit can include the sequence provided in this application with primers designed to perform nucleic acid amplification through a temperature cycling process or at a near constant temperature, in this latter case, preferably somewhere around 60° C. to 65° C., with a polymerase with strong strand displacement activity such as Bst DNA polymerase from *Bacillus stearothermophilus*, in a process called "loop-mediated isothermal amplification of DNA" (Notomi, T. et al., 2000. Loop-mediated isothermal amplification of DNA. Nucleic Acid Res. 28:e63).

The following examples are provided to further illustrate aspects of the invention. These examples are non-limiting and should not be construed as limiting any aspect of the invention.

EXAMPLES

Example 1

Materials and Methods

*Leishmania* Species and Strains.

Promastigotes were cultivated in modified minimal essential medium [HOMEM; (6)] or in Schneider's Insect Medium with 10% heat-inactivated FCS and 50 µg gentamicin/ml. DNA was extracted from the species and strains listed in Table 1. The *Leishmania* isolates were originally isolated from humans infected with leishmaniasis.

TABLE 1

Sources of *Leishmania* spp. isolates used in this project development.

| *Leishmania* species | Source | Name if any |
| --- | --- | --- |
| *L.* (*L.*) *tropica* 1 | F. Steurer, CDC | FJ |
| *L.* (*L.*) *tropica* 2 | F. Steurer, CDC | You |
| *L.* (*L.*) *tropica* 3 | F. Steurer, CDC | Sp |
| *L.* (*L.*) *tropica* 4 | F. Steurer, CDC | KiR |
| *L.* (*L.*) *tropica* 5 | F. Steurer, CDC | GH |
| *L.* (*L.*) *tropica* 6 | F. Steurer, CDC | TAM |
| *L.* (*L.*) *chagasi* | S. Jeronimo, UFRN, Natal, Brasil | MHOM/BR/00/1669 |
| *L.* (*L.*) *chagasi* attenuated | Above isolate multiply passaged in vitro, M. Wilson | MHOM/BR/00/1669 strain L5 |
| *L.* (*L.*) *infantum* | D. McMahon-Pratt, Yale U. | (2) |
| *L.* (*L.*) *donovani* | Buddy Ullman, OHSU | D1700(29) |
| *L.* (*L.*) *donovani* Reference | Shyam Sundar, Banaras Hindu University | LEM 138(MHOM/IN/DEVI) |
| *L.* (*L.*) *donovani* 1 | Shyam Sundar, Banaras Hindu University | BHU 764 |
| *L.* (*L.*) *donovani* 2 | Shyam Sundar, Banaras Hindu University | BHU 770 |
| *L.* (*L.*) *donovani* 3 | Shyam Sundar, Banaras Hindu University | BHU782 |
| *L.* (*L.*) *donovani* 4 | Shyam Sundar, Banaras Hindu University | BHU796 |
| *L.* (*L.*) *donovani* 5 | Shyam Sundar, Banaras Hindu University | BHU814 |
| *L.* (*L.*) *donovani* 6 | Shyam Sundar, Banaras Hindu University | BHU 921 |
| *L.* (*L.*) *donovani* 7 | Shyam Sundar, Banaras Hindu University | BHU922 |
| *L.* (*L.*) *major* | M. Wilson, University of Iowa | CDCID:LW9 |
| *L.* (*V.*) *braziliensis* | R. Almeida and E. Carvalho, UFBA, Salvador, Brazil | CDCID:LW10 |
| *L.* (*V.*) *braziliensis* | A. Schriefer, UFBA, Salvador, Brazil | 13330 |
| *L.* (*V.*) *braziliensis* | A. Schriefer, UFBA, Salvador, Brazil | 13968 |
| *L.* (*V.*) *guyanensis* (French Guyana) | N. Aronson, WRAIR | WR 2853 |
| *L.* (*V.*) *guyanensis* (French Guyana) | N. Aronson, WRAIR | WR 2334 |
| *L.* (*V.*) *panamensis* (Panama) | N. Aronson, WRAIR | WR 2306 |
| *L.* (*V.*) *panamensis* (Panama) | N. Aronson, WRAIR | WR 2307 |
| *L.* (*L.*) *mexicana* | R. Almeida and E. Carvalho, UFBA, Salvador, Brazil | CDCID:LW5 |
| *L.* (*L.*) *amazonensis* | Diane McMahon-Pratt, Yale University | 4588 |
| *Leptomonas* sp. BHU | Shyam Sundar, Banaras Hindu University | BHU 151(*Leptomonas seymouri* like) |
| *Crithidia fasciculate* | ATCC | LEM 138(MHOM/IN/DEVI) | qPCR Primers and Probe Design.

Primers targeting kinetoplast minicircle, maxicircle, and the nuclear genome were designed to be used in a SYBR green qPCR assay for detection, species discrimination and quantification (Table 2 Forward and Reverse Primers). In four cases, these assays were designed using primers from a previously reported Taqman assay (marked as "adapted from" in Table 2). All other primer pairs used for SYBR green qPCR assays were designed from sequence databases to amplify either genes that had been targeted by other PCR diagnostic assays of leishmaniasis, or genes targeted uniquely for the current study. In addition to SYBR green assays, we developed primers within a subset of these sequences as Taqman assays. Taqman probes were designed by JW with the exception of the two sequences indicated in Table 2 (kDNA5, DNA polymerase 1).

TABLE 2

Primers and probes used for Leishmania qPCR diagnosis and speciation. All sequences were developed for use either as SYBR green and/or Taqman assays.

| | Designation | Forward Primer | Reverse Primer | Taqman Probe 5' FAM ™/3' TAMRA ™ | Sequence Source[1] | Reference |
|---|---|---|---|---|---|---|
| Mini-circle | kDNA 1 minicircle | GGGTAGGGGC GTTCTGC (SEQ ID NO: 1) | TACACCAACCCC CAGTTTGC (SEQ ID NO: 2) | | M94088 | JW[1] |
| | kDNA 2 | AACTTTTCTGG TCCTCCGGGTA G (SEQ ID NO: 97) | ACCCCCAGTTTCC CGCC (SEQ ID NO: 98) | | EU437406 | Leish1 and 2 in (21) |
| | kDNA 3 minicircle | GGGTAGGGGC GTTCTGC (SEQ ID NO: 3) | CCCGGCCTATTTT ACACCAACC (SEQ ID NO: 4) | | M94088 | JW |
| | kDNA 4 minicircle | GGGTGCAGAA ATCCCGTTCA (SEQ ID NO: 5) | CCCGGCCCTATTT TACACCA (SEQ ID NO: 6) | ACCCCCAGTTTCCC GCCCCG | Conserved kDNA[2] as found in AF027578 | JW |
| | kDNA 5 minicircle | CTTTTCTGGTC CTCCGGGTAG (SEQ ID NO: 99) | CCACCCGGCCCT ATTTTACACCAA (SEQ ID NO: 100) | TTTTCGCAGAACGC CCCTACCCGC | Z35500 | Taqman ™ qPCR (42)[3] |
| | kDNA 7 minicircle | AATGGGTGCA GAAATCCCGT TC (SEQ ID NO: 7) | CCACCACCCGGC CCTATTTTAC (SEQ ID NO: 8) | CCCCAGTTTCCCGC CCCGGA | Conserved kDNA[2] as found in Z35500 | JW |
| | L. (L.) amazonensis kDNA 1 | GGTCCCGGCC CAAACTTTTC (SEQ ID NO: 9) | CCGGGGTTTCGC ACTCATTT (SEQ ID NO: 10) | | U19810 | JW |
| | L. (L.) amazonensis kDNA 2 | GGTAGGGGCG TTCTGCGAAT (SEQ ID NO: 11) | CCCGGCCTATTTT ACACCAACC (SEQ ID NO: 12) | TGGCCTTGGGGCGT GCAAACTGG | EU370875 | JW |
| | L. (L.) amazonensis kDNA 3 | GGGTAGGGGC GTTCTGC (SEQ ID NO: 13) | TACACCAACCCC CAGTTTGC (SEQ ID NO: 14) | | M94089 | JW |
| | L. (L.) amazonensis kDNA 4 | TGAGTGCAGA AACCCCGTTC ATA (SEQ ID NO: 15) | ACACCAACCCCC AGTTGTGA (SEQ ID NO: 16) | | EU370875 | JW |
| | L (V.) brazilien-sis kDNA 1 | AATTTCGCAG AACGCCCCTA C (SEQ ID NO: 17) | GTACTCCCCGAC ATGCCTCTG (SEQ ID NO: 18) | | U19807 | JW |
| | L (V.) brazilien-sis kDNA 3 | TGCTATAAAA TCGTACCACCC GACA (SEQ ID NO: 101) | GAACGGGTTTC TGTATGCCATTT (SEQ ID NO: 102) | TTGCAGAACGCCCC TACCCAGAGGC | AF231100 | Adapted from PCR (58)[4] |
| | L (L.) infantum Minicircle 1 | TCCGCAGGAG ACTTCGTATG (SEQ ID NO: 103) | CACGACTATCCA CCCCATCC (SEQ ID NO: 104) | CTGAGAGACCCGCC GGGGCG | AF032997 | Adapted from nested PCR (23) |

TABLE 2-continued

Primers and probes used for *Leishmania* qPCR diagnosis and speciation. All sequences were developed for use either as SYBR green and/or Taqman assays.

| | Designation | Forward Primer | Reverse Primer | Taqman | Sequence Source[1] | Reference |
|---|---|---|---|---|---|---|
| | *L. (L.) major* Minicircle 1 | ACGGGGTTTCT GCACCCATT (SEQ ID NO: 19) | GTAGGGGCGTTC TGCGAAAA (SEQ ID NO: 20) | | EU370908; AJ275330; J04654; LM15_BIN_ Contig406; PMID: 16020728 | JW |
| | *L. (L.) mexicana* Minicircle 1 | AATGCGAGTG TTGCCCTTTTG (SEQ ID NO: 21) | GCCGAACAACGC CATATTAACC (SEQ ID NO: 22) | | AY145437 | JW |
| | *L. (L.) tropica* Minicircle 1 | GGGGGTTGGT GTAAAATAGG G (SEQ ID NO: 23) | ACCACCAGCAGA AGGTCAAAG (SEQ ID NO: 24) | TCCTGGCGGGGTT TTCGCT | AF308689 | JW |
| | *L. (L.) donovani* Minicircle 1 | GCGGTGGCTG GTTTTAGATG (SEQ ID NO: 25) | TCCAATGAAGCC AAGCCAGT (SEQ ID NO: 26) | CCCATACCACCAAA CGCAGCCCA | FJ416603 | JW |
| Maxi-circle | Cytochrome B 1 | ATTTTAGTATG AGTGGTAGGT TTTGTT (SEQ ID NO: 27) | CAATAACTGGGA CGGTTGCT (SEQ ID NO: 28) | CCATGTACGATGAT GTCGTATTGAGGTC TAACA | AB095960 | JW |
| | *L. (L.) amazonensis* Cytochrome B1 | GCGGAGAGGA AAGAAAAGGC TTA (SEQ ID NO: 29) | AAAAGTCATGCT AAACACACACCA CA (SEQ ID NO: 30) | | AB095964 | JW |
| | *L. (L.) tropica* Cytochrome B 1 | CAGGTTGCTTA CTACGTGTTTA TGGTG (SEQ ID NO: 31) | TCGTATTACAAA CCCTAAATCAAA ATCTCA (SEQ ID NO: 32) | | AB095960 | JW |
| | *L. (L.) tropica* Cytochrome B 2 | TCAGGTTGCTT ACTACGTGTTT ATGGTG (SEQ ID NO: 33) | TGCTAAACAAAC ACCACATATGAT CTGC (SEQ ID NO: 34) | | AB095960 | JW |
| | *L. (L.) tropica* Cytochrome B 3 | TGACACACAT ATTTTAGTGTG GGTGGTAGG (SEQ ID NO: 35) | TCCCCAATAAGA CATCATTGTACAT GGTAA (SEQ ID NO: 36) | | EF579904 | JW |
| | *L. (L.) tropica* Cytochrome B 4 | CACATATTTTA GTGTGGGTGG TAGGTTTTG (SEQ ID NO: 37) | TCCCCAATAAGA CATCATTGTACAT GGTAA (SEQ ID NO: 38) | | EF579904 | JW |
| | Maxicircle 1 | GCTTGGTTGG ATTATTTTTGC TG (SEQ ID NO: 39) | AACAACATTTTA ACTCTTGTAGGAT TCG (SEQ ID NO: 40) | CTTTAGGTAGGAG TTGTACTACGTTTTT TGACCT | DQ492252 | JW |
| Genomic | Alpha-tubulin 1 | GAGGTGTTTG CCCGCATC (SEQ ID NO: 41) | CTCGCCCATGTCG TCG (SEQ ID NO: 42) | TGAGGGCATGGAGG AGGGCG | XM_001681731 | JW |
| | DNA polymerase 1 | TGTCGCTTCA GACCAGATG (SEQ ID NO: 105) | GCATCGCAGGTG TGAGCA (SEQ ID NO: 106) | CAGCAACAACTTCG AGCCTGGCACC | AF009147 | Taqman ™ qPCR (9)[4] |

TABLE 2-continued

Primers and probes used for *Leishmania* qPCR diagnosis and speciation. All sequences were developed for use either as SYBR green and/or Taqman assays.

| Designation | Forward Primer | Reverse Primer | Taqman | Sequence Source[1] | Reference |
|---|---|---|---|---|---|
| DNA polymerase 2 | AGGAGGATGG CAAGCGGAAG (SEQ ID NO: 43) | GCGACGGGTACA GGGAGTTG (SEQ ID NO: 44) | TGGGGTCGAGCACC ATGCCGCC | AF009136 | JW |
| Mini-exon 1 | CGAAACTTCC GGAACCTGTC TT (SEQ ID NO: 45) | CACCACACGCAC GCACAC (SEQ ID NO: 46) | CGGCAAGATTTTGG AAGCGCGCA | AL389894 | JW |
| Mini-exon 2 | GTGTGGTGGC GGGTGTATGT (SEQ ID NO: 47) | GCCCAGGTCGCT GTGAGG (SEQ ID NO: 48) | | LbrM02_V2.0710 | JW |
| MSP Associated Gene 1 (MAG 1) | AGAGCGTGCC TTGGATTGTG (SEQ ID NO: 49) | CGCTGCGTTGATT GCGTTG (SEQ ID NO: 50) | TGCGCACTGCACTG TCGCCCCC | AF058760 | JW |
| MSP Associated Gene 2 (MAG 2) | AGTTTTGGTTG GCGCTCCTG (SEQ ID NO: 51) | CCCACTCGCTTTC CTTGGTC (SEQ ID NO: 52) | CGCTGAGAGCGAGG CAGGCACGC | AF058760 | JW |
| SIDER repeat 1 | CGACCCTGTC ACCACCACAG (SEQ ID NO: 53) | GAGGCCACCCTA TCGCTGAC (SEQ ID NO: 54) | | AM937229 | JW |
| L. (V.) braziliensis DNA polymerase 1 | TCGTTGAGGG AGGAGGTGTT TC (SEQ ID NO: 55) | TCGGCTTTGAGGT TGGCTTC (SEQ ID NO: 56) | | XM_001563712 | JW |
| L. (V.) braziliensis DNA polymerase 2 | ACGTCGCCAA CTGCTTCACC (SEQ ID NO: 57) | GTGTTCGCACCG CCTTGAC (SEQ ID NO: 58) | | XM_001563712 | JW |
| L. (L.) major MSP associated gene 1 (L. major MAG 1) | GTCGTTGTCCG TGTCGCTGT (SEQ ID NO: 59) | CGCTGTGTGTGTC CGTGTGT (SEQ ID NO: 60) | | XM_001681328 | JW |
| L (L.) amazonensis DNA polymerase 1 | GACGACGACG AGGAGGATGG (SEQ ID NO: 61) | GCGACGGGTACA GGGAGTTG (SEQ ID NO: 62) | | AF009136 | JW |
| GPI | CCAGATGCCGA CCAAAGC (SEQ ID NO: 107) | CGCGCACGTGATG GATAAC (SEQ ID NO: 108) | | AM117195 | (68) |
| HSP70-1 | GAAGGTGCAG TCCCTCGTGT (SEQ ID NO: 63) | CCTCCGTCTGCTT GCTCTTG (SEQ ID NO: 64) | | FN395029 | JW |
| HSP70-4 | TCGAGATCGAC GCGTTGTT (SEQ ID NO: 65) | CCGCACAGCTCCT CGAA (SEQ ID NO: 66) | | FN395037 | JW |

TABLE 2-continued

Primers and probes used for *Leishmania* qPCR diagnosis and speciation. All sequences were developed for use either as SYBR green and/or Taqman assays.

| | Designation | Forward Primer | Reverse Primer | Taqman | Sequence Source[1] | Reference |
|---|---|---|---|---|---|---|
| | SLACS | GGAGAAACTC ACGGCACAGG (SEQ ID NO: 67) | GCGCCTCGTAGGT CACAGTT (SEQ ID NO: 68) | | XM_001562078 | JW |
| Lepto-monas DNA | *Leptomonas* Mini-exon 1 | TGGAGCGGGT GCATTAACTC (SEQ ID NO: 69) | GGTCTCGAGGTGC CCATGAC (SEQ ID NO: 70) | | S78663 | JW |
| | *Leptomonas* GAPDH 2 | AGAAGCCGGA TGTGCTTGTG (SEQ ID NO: 71) | GCCCTCAGCCTTC ACCTTGT (SEQ ID NO: 72) | | AF053738 | JW |
| Human DNA | | | | Probe 5' VIC ®/3' TAMRA ™ | | |
| | Human TNF alpha 1 | GCCCTGTGAGG AGGACGAAC (SEQ ID NO: 73) | AAGAGGTTGAGG GTGTCTGAAGGA (SEQ ID NO: 74) | CCTTCCCAAACGCC TCCCCTGCCCC | NM_000594 | JW |
| | Human TNF alpha 2 | GCGCTCCCCA AGAAGACAGG (SEQ ID NO: 75) | TGCCACGATCAG GAAGGAGAAG (SEQ ID NO: 76) | CACCGCCTGGAGCC CTGGGGC | NM_000594 | JW |
| | Human GAPDH 1 | GGGCTCTCCA GAACATCATC C (SEQ ID NO: 77) | CCAGTGAGCTTC CCGTTCAG (SEQ ID NO: 78) | | NG_007073 | JW |
| | Human GAPDH 2 | CATCAAGAAG GTGGTGAAGC AG (SEQ ID NO: 79) | CGTCAAAGGTGG AGGAGTGG (SEQ ID NO: 80) | | NG_007073 | JW |
| | Human GAPDH 3 | GCATGGCCTTC CGTGTCC (SEQ ID NO: 81) | CGCCTGCTTCACC ACCTTCT (SEQ ID NO: 82) | | NG_007073 | JW |

[1]JW - Primers and probes were designed by inventor. The Sequence Source is GenBank or NCBI RefSeq, National Center for Biotechnology Information (Bethesda, MD) at www.ncbi.nlm.nih.gov. Sequence provided may be used to search publically available databases through the National Center for Biotechnology Information using BLAST program to obtain additional sequence sources that those listed in the table. PMID - PubMed ID number used to query PubMed database for associated article at www.ncbi.nlm.nih.gov.
[2]The 'conserved kDNA' sequences used multiple sources aligned with CLUSTALW.
[3]Taqman qPCR - Primers and probes are exact ones used for a Taqman, but not a SYBR green, assay reported in the literature citation.
[4]"Adapted from (ref)" The targeted sequence in the literature reference was used to re-design primers and probes by JW.

Sequences from kinetoplast minicircles were derived from the NCBI Entrez nucleotide database (http://www.ncbi.nlm.nih.gov/sites/entrez?db=nuccore). Primers and probes suitable for qPCR were designed using the Primer3 website (http://frodo.wi.mit.edu/primer3/) (58). Product sizes were designed to be less than 150 bp.

Minicircle primers were designed against both conserved targets and species-specific sequences. Sequences from the kinetoplast maxicircles were derived from protein coding sequences that are not subject to the extensive RNA editing (26). The maxicircle 1 primer set was specifically designed against a variable region to maximize usefulness in species discrimination. Other maxicircle genes were designed to amplify cytochrome B sequences.

Within the nuclear genome, the assay for the DNA polymerase 1 gene was based upon a reported Taqman™ assay (9). The flanking primer set for this Taqman assay was found to be adequate for an independent SYBR green qPCR. The DNA polymerase gene is a single copy gene, raising its utility for quantitative assay of parasites. Mini-exon 1 and 2, alpha-tubulin 1, HSP70 and the SIDER repeat 1 primer sets were chosen because they amplify repetitive sequences and should therefore be sensitive. The MSP Associated Gene (mag) 1 and 2 primer sets were designed against mag gene sequences only known to be present in the *Leishmania* (L.) *infantum* and *L.* (L.) *chagasi* (46), in anticipation that these sequences could be useful in species discrimination. *L.* (L.) *major* contains a hypothetical ortholog to mag (LmjF.10.0483), identified by a shared P-fam B domain (21814) identified by the ADDA algorithm (28). This prompted the design of primers for the *L.* (L.) *major MSP* associated gene 1. Finally, the gene encoding glucose phosphate isomerase (GPI) was selected due to prior reports of its use in qPCR assays (68).

The genus *Leishmania* has two subgenuses, designated *L. viannia* spp. or *L. leishmania* spp. Examination of genomes has revealed that *L. Viannia braziliensis* has retrotransposable elements not found in *L. leishmania* species (52). We designed a primer set to target the splice-leader associated (SLACS) retrotransopons of *L.* (V.) *braziliensis*. Although genome sequences are not available for other members of the *Viannia* subgenus *L.* (V.) *guyanensis* and *L.* (V.) *panamensis*, we also tested the ability of this primer set to differentiate between *L.* (V.) *braziliensis* and each of these other species.

Two non-*Leishmania* species members of the Trypanosomatidae (*Crithidia fasciculata* and *Leptomonas*) were studied for potential cross-reactivity of primers. The latter organism, *Leptomonas* sp., has been recovered from the spleens of several individuals with symptoms of visceral leishmaniasis (62). Primers for human TNF alpha 1 and 2 target the single copy human TNF alpha gene (23). These and primers for human GAPDH were designed as positive controls for qPCR amplification.

DNA Extraction.

5-10 ml cultures were suspended in lysis buffer (150 mM NaCl, 4 mg/ml SDS, 10 mM EDTA, 10 mM Tris-HCl, pH 7.5) with 200 μg proteinase K/ml for 1 hr. at 56° C. DNA was extracted in Tris-equilibrated phenol, then Phenol:CHCl$_3$:IsoAmyl Alcohol (25:24:1) followed by CHCl$_3$:IsoAmylAlcohol (49:1). Samples were ethanol precipitated and resuspended in water.

qPCR Assay Conditions.

All reactions were conducted on a 7900 Fast Real-Time PCR system from Applied Biosystems (ABI) in 10 ul reaction volumes. SYBR green reactions were composed of ABI Power SYBR green 2× master mix, and 500 nM each of forward and reverse primers. TaqMan reactions were performed with ABI TaqMan universal PCR 2× master mix, 375 nM each of forward and reverse primers, and 250 nM of probe (label 5'FAM, quench 3' TAMRA). Thermocycling parameters were: hold (95 degrees, 10 min) followed by 40 temperature cycles (95 degrees for 15 sec, 60 degrees for 1 min). A melt curve analysis was performed on all SYBR green reactions. Results were analyzed in SDS 2.4 software with an automatic baseline and a manual cycle threshold (CT) of 0.2 for all reactions. The R software package was used to generate melt curve plots for primer sets in which melting temperatures differed by at least 1 degree between species.

Multiplex TaqMan qPCR.

A multiplex Taqman qPCR assay was designed to detect all tested *Leishmania* species, and simultaneously differentiate between members of the visceralizing *L. donovani* complex and other species that cause primarily tegumentary disease. The DNA polymerase 2 primers and probe (label 5' TET, quench Iowa Black), and MSP associated gene 2 (label 5' FAM, quench TAMRA) were used together in 10 μl reaction with 125 nM of each forward and reverse primers and 83 nM of each probe. Thermocycling parameters were identical to the conditions described above.

Results

Detection and Differentiation Between *Leishmania* Species.

Based on the above designed SYBR green primer sets and Taqman probes, we developed qPCR assays with the dual objectives of developing a sensitive assay that could detect all *Leishmania* species infections in clinical or experimental specimens, and discriminating between the different *Leishmania* species. For these purposes, forty one *Leishmania* specific primer pairs were tested in SYBR green assays. All were tested in the presence of 10-fold excess of human DNA compared to DNA extracted from parasites. Seventeen targeted the kinetoplast minicircle, seven targeted maxicircle sequences and seventeen targeted genes in the nuclear genome. Two primer pairs were developed to identify the related *Leptomonas* spp. protozoa, which have been reported as co-isolates with *L. donovani* (62). Five primer pairs were also included as positive controls for human DNA in specimens. These could additionally be used for normalization to a baseline of human DNA in clinical samples tested.

For some but not all primer sets, differences in melt temperature curves were useful in distinguishing between *Leishmania* species (FIG. 1). For instance, kDNA1 clearly distinguished between *L.* (L.) *amazonensis* and *L.* (L.) *mexicana* or *L.* (L.) *tropica* and *L.* (L.) *major*, whereas *L.* (L.) *donovani*, *L.* (L.) *chagasi* and *L.* (L.) *infantum* exhibited very similar Tm peaks. In contrast, the MSP associated gene 1 primer pair distinguished *L.* (L.) *donovani* from *L.* (L.) *chagasi/L.* (L.) *infantum*.

Taqman assays corresponding to a subset of the SYBR primers that are listed on Table 2 were experimentally validated. Table 3 spells out the relative efficiency of each SYBR green or Taqman assay for detecting and differentiating between *Leishmania* spp. CT values listed on this table reflect the cycle in which the intensity exceeded a threshold of 0.2 when amplifying 0.1 ng of total parasite DNA in the presence of 1 ng of human DNA. Products that amplified with a CT greater than 30 were excluded because these extreme values were often caused by primer-dimers or off-target amplification in SYBR green reaction assays. Such artifacts can be discerned using melt curve analyses (not shown) for some primer sets. The cutoff could be raised for Taqman assays, as primer-dimers do not impact those results. The cutoff of 30 cycles is roughly equivalent to 0.005 parasites per well when amplifying minicircle sequences, or 102 parasites when amplifying a genomic sequence with SYBR green reagents.

TABLE 3

Relative efficiency of SYBR green or Taqman assays for detecting and differentiating *Leishmania* spp., or for *Leptomonas* spp. or *Crithidia fasciculata*. Data indicate the average CT values of 2 replicates for *Leptomonas* and *L. amazonensis*, or 4 replicates for all other species. CT values reflect the cycle in which fluorescence intensity reached 0.2 when amplifying 0.1 ng of total parasite DNA in the presence of 1 ng of human DNA. The cutoff of CT = 30 avoids ambiguities caused by primer dimers in SYBR green assays. Please note that CT cutoffs could differ between different strains, or when assays are performed in different labs.

|  | *L.* (L.) amazonensis | *L.* (V.) braziliensis | *L.* (L.) chagasi | *L.* (L.) donovani | *L.* (L.) infantum | *L.* (L.) major | *L.* (L.) mexicana | *L.* (L.) tropica | Leptomonas | Crithidia |
|---|---|---|---|---|---|---|---|---|---|---|
| SYBR GREEN | | | | | | | | | | |
| Alpha-tubulin | 21.4 | >30 | 20.7 | 20.3 | 21.1 | 20.8 | 21.4 | 23.4 | 27.8 | 28.3 |
| Cytochrome B 1 | >30 | >30 | 23.8 | 20.0 | 22.0 | >30 | >30 | >30 | >30 | >30 |

TABLE 3-continued

Relative efficiency of SYBR green or Taqman assays for detecting and differentiating *Leishmania* spp., or for *Leptomonas* spp. or *Crithidia fasciculata*. Data indicate the average CT values of 2 replicates for *Leptomonas* and *L. amazonensis*, or 4 replicates for all other species. CT values reflect the cycle in which fluorescence intensity reached 0.2 when amplifying 0.1 ng of total parasite DNA in the presence of 1 ng of human DNA. The cutoff of CT = 30 avoids ambiguities caused by primer dimers in SYBR green assays. Please note that CT cutoffs could differ between different strains, or when assays are performed in different labs.

| | *L. (L.) amazonensis* | *L. (V.) braziliensis* | *L. (L.) chagasi* | *L. (L.) donovani* | *L. (L.) infantum* | *L. (L.) major* | *L. (L.) mexicana* | *L. (L.) tropica* | *Leptomonas* | *Crithidia* |
|---|---|---|---|---|---|---|---|---|---|---|
| DNA polymerase 1 | 25.1 | 29.0 | 23.5 | 23.0 | 24.7 | 24.5 | 25.6 | 27.5 | >30 | >30 |
| DNA polymerase 2 | 24.1 | 23.4 | 22.9 | 22.5 | 24.3 | 24.2 | 24.7 | 27.9 | 29.2 | 26.5 |
| GPI | 24.3 | 29.4 | 23.1 | 22.9 | 24.4 | 24.6 | 25.2 | 27.1 | >30 | >30 |
| HSP70-1 | 21.3 | 21.4 | 19.8 | 19.4 | 21.3 | 20.8 | 22.5 | 23.7 | >30 | >30 |
| HSP70-4 | 21.7 | 22.1 | 20.1 | 19.9 | 21.5 | 20.9 | 22.8 | 24.0 | 27.0 | 23.6 |
| kDNA 1 | 15.6 | 27.2 | 15.7 | 14.4 | 15.3 | 19.6 | 16.5 | 15.4 | 26.6 | 13.2 |
| kDNA 2 | >30 | 29.3 | 14.6 | 12.8 | 14.4 | 11.8 | 19.2 | 29.8 | 26.4 | 29.6 |
| kDNA 3 | 14.7 | 18.9 | 14.8 | 13.0 | 14.3 | 11.4 | 13.7 | 15.4 | 23.4 | 18.3 |
| kDNA 4 | 16.3 | 25.6 | 14.6 | 12.9 | 14.4 | 11.7 | 14.8 | 21.5 | 26.0 | 27.8 |
| kDNA 5 | >30 | 28.7 | 14.8 | 13.1 | 14.3 | 11.6 | 20.3 | 19.0 | 26.7 | 26.5 |
| kDNA 7 | 19.8 | 28.9 | 14.8 | 12.6 | 14.2 | 11.5 | 18.6 | 23.9 | 25.6 | 29.4 |
| *L. (L.) amazonensis* Cytochrome B 1 | 28.4 | 25.6 | 29.1 | 29.8 | 27.4 | >30 | >30 | >30 | >30 | >30 |
| *L. (L.) amazonensis* DNA polymerase 1 | 24.4 | 23.2 | 23.4 | 22.9 | 24.8 | 25.4 | 24.7 | 28.0 | 29.1 | 25.5 |
| *L. (L.) amazonensis* kDNA 3 | 15.6 | 27.0 | 15.6 | 14.5 | 15.2 | 19.3 | 16.5 | 15.2 | 27.2 | 13.1 |
| *L. (L.) amazonensis* kDNA 4 | 15.9 | >30 | >30 | >30 | >30 | >30 | 19.0 | >30 | >30 | >30 |
| *L. (L.) amazonensis* kDNA 2 | 15.2 | >30 | >30 | 28.2 | 29.5 | 24.3 | 21.8 | >30 | >30 | >30 |
| *L. (L.) amazonensis* kDNA 1 | 15.0 | 29.8 | >30 | 27.9 | >30 | 23.8 | 21.6 | >30 | >30 | >30 |
| *L. (V.) braziliensis* DNA polymerase 1 | >30 | 22.9 | >30 | >30 | >30 | >30 | >30 | >30 | >30 | >30 |
| *L. (V.) braziliensis* DNA polymerase 2 | 28.1 | 23.1 | 24.3 | 23.7 | 25.5 | >30 | 28.6 | 28.3 | 26.6 | >30 |
| *L. (V.) braziliensis* kDNA 1 | >30 | 13.5 | >30 | >30 | >30 | >30 | >30 | >30 | >30 | >30 |
| *L. (V.) braziliensis* kDNA 2 | >30 | 23.9 | >30 | >30 | >30 | >30 | >30 | >30 | >30 | >30 |
| *L. (V.) braziliensis* kDNA 3 | >30 | 17.7 | >30 | >30 | >30 | >30 | >30 | >30 | >30 | >30 |
| *L. (L.) chagasi* SIDER 1 | >30 | >30 | 21.7 | 21.7 | 22.4 | >30 | >30 | 26.4 | >30 | >30 |
| *L. (L.) infantum* minicircle 1 | >30 | >30 | 23.8 | >30 | 26.6 | >30 | >30 | >30 | >30 | >30 |
| *L (L.) major* MSP associated gene 1 (*L. major* MAG 1) | 23.2 | 27.6 | 22.4 | 21.3 | 24.5 | 24.1 | 25.1 | 23.2 | >30 | >30 |
| *L. (L.) major* minicircle 1 | 18.6 | 29.4 | 16.1 | 22.6 | 15.9 | 22.6 | 18.9 | >30 | 25.9 | 29.9 |
| *L. (L.) mexicana* minicircle 1 | >30 | >30 | >30 | >30 | >30 | >30 | 20.1 | >30 | >30 | >30 |
| *L. (L.) tropica* Cytochrome B 1 | >30 | >30 | >30 | >30 | >30 | >30 | >30 | 25.1 | >30 | >30 |
| *L. (L.) tropica* Cytochrome B 2 | >30 | >30 | 24.6 | 26.2 | 22.7 | >30 | >30 | 24.3 | >30 | >30 |
| *L (L.). tropica* Cytochrome B 3 | 28.4 | >30 | >30 | 29.4 | >30 | 23.2 | >30 | 26.2 | >30 | >30 |
| *L. (L.) tropica* Cytochrome B 4 | 24.1 | >30 | 26.7 | 23.2 | 24.8 | 22.0 | 24.5 | 25.0 | >30 | >30 |
| *L. (L.) tropica* minicircle 1 | >30 | >30 | >30 | >30 | >30 | >30 | >30 | 19.8* | >30 | >30 |
| *L. (L.) donovani* minicircle 1 | >30 | >30 | 29.4 | 15.3 | 25.9 | >30 | >30 | >30 | >30 | >30 |
| *Leptomonas* GAPDH 2 | >30 | 24.1 | >30 | >30 | >30 | >30 | >30 | >30 | 26.6 | 23.5 |
| *Leptomonas* mini-exon 1 | >30 | >30 | >30 | >30 | >30 | >30 | >30 | >30 | 20.7 | >30 |
| MSP associated gene 1 (MAG 1) | >30 | >30 | 21.2 | 20.8 | 23.6 | >30 | >30 | 25.8 | >30 | >30 |
| MSP associated gene 2 (MAG 2) | >30 | >30 | 21.0 | 20.8 | 23.4 | >30 | >30 | >30 | >30 | >30 |
| maxicircle 1 | >30 | >30 | 22.3 | 19.6 | 19.2 | >30 | >30 | >30 | >30 | >30 |
| mini-exon 1 | 21.6 | 26.3 | 17.9 | 16.7 | 19.6 | 19.0 | 25.5 | 18.9 | 29.6 | 29.1 |
| mini-exon 2 | 29.9 | 16.9 | 29.0 | 29.9 | 29.3 | 29.3 | 30.0 | >30 | >30 | >30 |
| SLACS | 29.9 | 19.7 | 29.8 | 30.0 | 29.9 | >30 | 29.9 | >30 | >30 | 29.8 |
| TAQMAN | | | | | | | | | | |
| taqman alpha-tubulin | 26.1 | >30 | 25.0 | 24.9 | 25.9 | 24.7 | 26.2 | 28.8 | >30 | >30 |
| taqman Cytochrome B 1 | >30 | >30 | 27.7 | 24.5 | 26.1 | >30 | >30 | >30 | >30 | >30 |
| taqman DNA polymerase 1 | 27.1 | >30 | 25.8 | 25.1 | 27.3 | 26.7 | 27.8 | 29.4 | >30 | >30 |
| taqman DNA polymerase 2 | 27.0 | 26.7 | 26.5 | 26.0 | 27.9 | 26.9 | 27.9 | 28.8 | >30 | >30 |
| taqman kDNA 4 | >30 | >30 | 18.1 | 17.3 | 17.8 | >30 | >30 | >30 | >30 | >30 |
| taqman kDNA 5 | >30 | >30 | 18.1 | 16.1 | 18.0 | 16.1 | 25.5 | 25.3 | >30 | >30 |
| taqman kDNA 7 | >30 | >30 | 18.4 | 17.5 | 18.1 | 23.6 | >30 | >30 | >30 | >30 |
| taqman *L. (V.) braziliensis* kDNA 3 | >30 | 21.9 | >30 | >30 | >30 | >30 | >30 | >30 | >30 | >30 |
| taqman *L. (L.) infantum* minicircle 1 | >30 | >30 | 28.8 | >30 | >30 | >30 | >30 | >30 | >30 | >30 |
| taqman *L. (L.) tropica* minicircle 1 | >30 | >30 | >30 | >30 | >30 | >30 | >30 | 23.6* | >30 | >30 |
| taqman *L. (L.) donovani* minicircle 1 | >30 | >30 | >30 | 18.1 | >30 | >30 | >30 | >30 | >30 | >30 |

TABLE 3-continued

Relative efficiency of SYBR green or Taqman assays for detecting and differentiating Leishmania spp., or for Leptomonas spp. or Crithidia fasciculata. Data indicate the average CT values of 2 replicates for Leptomonas and L. amazonensis, or 4 replicates for all other species. CT values reflect the cycle in which fluorescence intensity reached 0.2 when amplifying 0.1 ng of total parasite DNA in the presence of 1 ng of human DNA. The cutoff of CT = 30 avoids ambiguities caused by primer dimers in SYBR green assays. Please note that CT cutoffs could differ between different strains, or when assays are performed in different labs.

| | L. (L.) amazonensis | L. (V.) braziliensis | L. (L.) chagasi | L. (L.) donovani | L. (L.) infantum | L. (L.) major | L. (L.) mexicana | L. (L.) tropica | Leptomonas | Crithidia |
|---|---|---|---|---|---|---|---|---|---|---|
| taqman MSP associated gene 1 (MAG 1) | >30 | >30 | 23.5 | 24.3 | 25.9 | >30 | >30 | 28.3 | >30 | >30 |
| taqman MSP associated gene 2 (MAG 2) | >30 | >30 | 23.8 | 23.5 | 26.1 | >30 | >30 | >30 | >30 | >30 |
| taqman maxicircle 1 | >30 | >30 | 26.7 | 25.0 | 24.2 | >30 | >30 | >30 | >30 | >30 |
| taqman mini-exon 1 | 23.8 | >30 | 26.5 | 24.0 | 26.8 | 22.0 | >30 | 22.9 | >30 | >30 |
| Multiplex TAQMAN | | | | | | | | | | |
| taqman MSP associated gene 2 (MAG 2; 5' FAM/3' TAMRA) | >30 | >30 | 23.7 | 23.4 | 26.0 | >30 | >30 | >30 | >30 | >30 |
| taqman DNA polymerase 2 (5' TET/3'Iowa Black) | 25.3 | 24.9 | 25.7 | 24.9 | 26.6 | 25.6 | 25.9 | 28.8 | >30 | >30 |

Primer pairs targeting the multi-copy minicircle kDNA (kinetoplast DNA) were the most sensitive tests to detect any species of Leishmania. For many of the minicircle primers, exponential amplification occurred at a CT below 15 when amplifying 100 femtograms of parasite DNA using SYBR green. Maxicircle and nuclear genome targets were also effective in detecting parasites, although these primer sets were not as sensitive and required 25 or more cycles to reach detection (Table 3). Some of the late-amplifying markers demonstrated melt curves that were useful for distinguishing between species (Table 3). L. (L.) major MSP associated gene 1 is notable in that it amplifies all Leishmania species without amplifying the Leptomonas or Crithidia negative controls. The CT values in Table 3 can be used to assess the relative performance difference between species, but strains within species may differ slightly. Also, absolute CT values may vary somewhat between different laboratories.

Species in the subgenus Viannia were recognized by the primer set designated L. (V.) braziliensis kDNA 3, which was designed against the L. (V.) braziliensis genome (average CT values were 17.7, 13.5 or 13.3 when amplifying from L. (V.) braziliensis, L. (V.) guyanensis or L. (V.) panamensis genomic DNA, respectively). Therefore we tested additional primers that might differentiate this from the other Viannia subgenus members. The splice-leader associated (SLACS) retrotransposons are found in the L. (V) braziliensis genome, but not the subgenus Leishmania spp. analyzed to date (52). The primer pair SLACS amplified L. (V.) braziliensis DNA as predicted, although the primer set suffered from primer-dimer peaks at CTs greater than 28 in many species (Table 3). Because of a lack of genomic sequence information, it was unknown whether these primers would also amplify DNA from other Viannia subgenus members L. (V.) guyanensis or L. (V.) panamensis. Analyses revealed that despite the background amplification at CT values>28 due to primer-dimers, the SLACS primer set specifically amplified sequences in genomic DNA of L. (V.) braziliensis, but not L. (V.) guyanensis or L. (V.) panamensis DNA (average CT values were 19.7. 30.2 or 32.5 using genomic DNA from L. (V.) braziliensis, L. (V.) guyanensis or L. (V.) panamensis as templates). SLACS, therefore, provided the only set tested that distinguished between species within the Viannia subgenus.

To quantitatively assess the relative sensitivity of SYBR green versus Taqman assays of kDNA or genomic DNA sequences, we used kDNA 5 (minicircle) or DNA polymerase to amplify L. (L.) chagasi DNA. Standard curves were generated from DNA extracted from a known number of parasites. The approximate CT values for detection of a single parasite and the number of parasites detected at the CT cutoff point of 30 were determined (Table 4). The table demonstrates, first, increased sensitivity of the minicircle target sequence compared to the single copy gene target, as expected (20,400 fold enhanced sensitivity in the SYBR green assay). The table also showed increased sensitivity of SYBR green compared to Taqman for detection of either sequence when using earliest amplification as a measure of performance. Taqman is expected to have greater specificity than SYBR green, although when used in combination with melt curve analysis SYBR green can approach the sensitivity of Taqman assays for numbers of parasites exceeding the threshold.

TABLE 4

Sensitivity of qPCR assays for parasite detection. DNA extracted from known numbers of L. infantum chagasi promastigotes was amplified with kDNA 5 minicircle primers, or with primers hybridizing to the single copy gene DNA polymerase. The average CT values corresponding to numbers of promastigote genomes in a single well are indicated. Please note that this table should not be used for exact quantification, because the efficiency of the PCR reaction is expected to vary between the Leishmania species.

| | Approximate CT for 1 promastigote | Detection threshold with CT cutoff of 30 |
|---|---|---|
| Minicircle, SYBR green | 24.2 | 0.005 |
| Minicircle, Taqman | 27.7 | 0.18 |
| Genomic, SYBR green | 37.0 | 102 |
| Genomic, Taqman | 38.5 | 318 |

Specificity of Primer Pairs.

The reactions in Table 3 were carried out using 0.1 ng of parasite DNA in the presence of 1.0 ng of human DNA. No primer sets amplified in human DNA alone at a CT lower than 30. alpha-tubulin, DNA polymerase 2, HSP70-4, L. amazonensis DNA polymerase 1, L. (V.) braziliensis DNA polymerase 2, kDNA 1-7, L. (L.) amazonensis kDNA 3, L.

(L.) *major* minicircle 1, and mini-exon 1 showed cross-reactivity with *Crithidia fasciculata* or *Leptomonas* but not human DNA, indicating primer hybridization to sequences in other trypanosomatid protozoa. The CT can be used to differentiate species. A low CT serves as a criterion for choosing one marker over another with a higher expected CT for the species of interest. Examination of melt curves for some of these primer sets (e.g. mini-exon 2 in FIG. 1) show low amplification (high CT, shown as dotted lines in the figure) for many different species, migrating at a lower melt temperature than the main peak amplifying at the lowest CT value (*L.* (V.) *braziliensis* in FIG. 1). This low amplification could have been caused by the production of primer-dimers, although we cannot rule out a universally shared off-target DNA sequence. The final identification of *Leishmania* rather than cross-reactive sequence can be made either by examining the melt temperature in SYBR green assays, or by use of the Taqman probe at the validation step.

*Leishmania* Species Identification.

The above qPCR assays can be used, first, to identify and quantify any organism belonging to the genus *Leishmania*, and second, to discriminate between *Leishmania* species. Species identification is accomplished either by observing the melt temperature of the amplicon, or observing the presence or absence of some amplicons. Nine of the designed primer sets were found to be useful in discriminating between *Leishmania* species based upon the melt temperature of the amplicon (see FIG. 1). *L.* (L.) *infantum* and *L.* (L.) *chagasi* could not be distinguished based on any melt curve analysis. This provides validity to the melt temperature approach. More distantly related but non-identical *Leishmania* species could be readily distinguished depending on the primer set used. In some instances, species identification could be attained through the exclusive amplification of one or a few species by a primer set. For example, *L.* (L.) *mexicana* minicircle 1 uniquely amplifies *L.* (L.) *mexicana* DNA but not other species.

We used the above information to generate a flow chart of qPCR tests recommended to (1) determine whether any *Leishmania* spp. is present in a clinical or environmental sample and (2) identify which species is present (FIG. 2). The example shows a sequence of tests appropriate for species found in Latin America. According to the figure, the DNA is first amplified using SYBR green qPCR assays for kDNA1 and *L.* (V.) *braziliensis* kDNA 3, to detect all *Leishmania* species. The next step is examination of the melting temperature of kDNA amplicons, a step that will differentiate false from true positives. Samples that test positive for *Leishmania* DNA would undergo a secondary set of SYBR green qPCR reactions to determine the species of infecting parasite, and to validate the initial result. These include *L.* (L.) *amazonensis* kDNA 2 and MSP associated gene 1 for specimens in which *L.* (L.) *amazonensis, L.* (L.) *chagasi/infantum* or *L.* (L.) *donovani* are suspected from the kDNA 1 melt curve, and *L. mexicana* minicircle 1 when *L. mexicana* or *L. major* are suspected. The melting temperature differs based on size and GC composition and should be unique to each species. It is recommended to conduct the species test along with appropriate positive control DNAs, as melt curve temperatures may vary slightly between experiments due to subtle differences in buffers or between machines. As a final verification, which could be considered optional especially in settings where cost is a primary issue, a Taqman assay specific for the infecting *Leishmania* species may be used. The inability of any primers to distinguish between *L. chagasi* and *L. infantum* is consistent with the current belief that these species seem to be genetically identical (17,44).

Other series of tests would be recommended for detection/species discrimination in other geographic regions (see Table 5 for a list of markers to distinguish common species). The list is not exhaustive, and existing tests will need to be tested for their capacity to distinguish additional species as needed for some regions.

TABLE 5

Serial qPCR studies recommended for detection and speciation of *Leishmania* spp. in clinical or environmental specimens based on geographic region.

| Region | Clinical Syndrome[a] | Expected *Leishmania* species | First step: Detection | Second step: Species discrimination |
|---|---|---|---|---|
| North, Central and South America | LCL | *L.* (L.) *amazonensis*<br>*L.* (L.) *mexicana*<br>*L.* (V.)[b] *braziliensis,*<br>*L.* (V.) *panamensis,*<br>*L.* (V.) *guyanensis*<br>*L.* (L.) *infantum chagasi* (rare) | kDNA 1<br>*L. braziliensis*<br>kDNA 3 | kDNA 1 melt curve<br>MAG 1 melt curve<br>*L. braziliensis* kDNA 3<br>SLACS |
| North, Central and South America | MCL, DL, DCL | *L.* (V.) *braziliensis,*<br>*L.* (V.) *panamensis,*<br>*L.* (V.) *guyanensis*<br>*L.* (L.) *amazonensis*<br>*L.* (L.) *mexicana* | *L. amazonensis*<br>kDNA 3<br>*L braziliensis*<br>kDNA 3 | *L. amazonensis*<br>kDNA3 melt curve<br>*L. braziliensis*<br>kDNA 3<br>SLACS |
| North, Central and South America | VL | *L.* (L.) *infantum*<br>*L.* (L.) *amazonensis* (rare) | kDNA 2<br>*L. amazonensis*<br>kDNA4 | kDNA 2*<br>*L. amazonensis*<br>kDNA4* |
| Europe | VL | *L.* (L.) *infantum*<br>*L.* (L.) *donovani* | kDNA 1 | MAG 1 melt curve |
| Middle East, Northern and sub-Saharan Africa | CL, DCL, LR | *L.* (L.) *major*<br>*L.* (L.) *tropica*<br>*L.* (L.) *infantum* (rare)<br>*L* (L.) *donovani* (rare) | kDNA 1 | kDNA 1 melt curve<br>MSP associated gene 1 (MAG 1) melt curve<br>*L. tropica* Cytochrome B 1* |

TABLE 5-continued

Serial qPCR studies recommended for detection and speciation of Leishmania spp. in clinical or environmental specimens based on geographic region.

| Region | Clinical Syndrome[a] | Expected Leishmania species | First step: Detection | Second step: Species discrimination |
|---|---|---|---|---|
| Middle East, Northern and sub-Saharan Africa | VL, PKDL | L. (L.) infantum L. (L.) donovani L. (L.) tropica (rare) | kDNA 1 | kDNA 1 melt curve MAG 1 melt curve L. tropica cytochromeB1* |
| India/Bangladesh/ Pakistan/Nepal | VL, PKDL | L. (L.) donovani | kDNA 1-7 (any one) | |
| Asia | VL | L. (L.) donovani | kDNA 1-7 (any one) | |

[a]Clinical syndromes are: DCL—diffuse cutaneous leishmaniasis; DL—disseminated leishmaniasis; LCL—localized cutaneous leishmaniasis; LR—leishmaniasis recidivans; MCL—mucocutaneous leishmaniasis; VL—visceral leishmaniasis
[b]Viannia or V. refers to parasites belonging to the subgenuses Viannia. All other species listed belong to the Leishmania subgenus.
*Marker amplifies only one species listed in the 3$^{rd}$ column.

The combination of DNA polymerase 2 and MSP associated gene 2 taqman qPCR assays was developed into a multiplex reaction that distinguished between visceralizing versus other Leishmania species. DNA polymerase 2 is capable of amplifying DNA from all species, albeit less efficiently in L. (L.) tropica. The latter required several more cycles of amplification compared to other species tested. Among the visceralizing species L. (L.) chagasi, L. (L.) donovani and L. (L.) infantum, the MSP associated gene was amplified at earlier CTs than DNA polymerase, mitigating the possibility that the DNA polymerase 2 amplification could consume the reaction reagents and mask the results (Table 3). L. (L,) tropica did show some amplification at late CTs with the MSP associated gene 2 primer set. However since these occurred late in the reaction, and later than the DNA polymerase 2 amplification, it is easily discernable from the L. (L.) donovani complex members. This finding is of interest due to the ability of L. (L.) tropica to cause not only cutaneous ulcers but also disseminated disease (37), although one cannot draw conclusions without sequence and functional data.

kDNA Copy Numbers.

Real time and Taqman PCR are capable of quantifying parasite numbers in clinical or experimental specimens. Absolute quantification is determined by comparison to standard curves from parasite DNA. Since kDNA probes are most sensitive, it makes sense to perform quantification with these primers. However, the use of kDNA for quantification is complicated by the fact that Leishmania species contain multiple copies of both minicircle and maxicircle kDNA. It is not known whether copy numbers differ between the Leishmania species, between different isolates of the same species, or between parasite stages. We therefore employed minicircle and maxicircle kDNA qPCR assays to determine the relative difference in minicircle and maxicircle kDNA copy numbers between three different species of Leishmania (Table 6), between a recent and a multiply-passaged line of the same L. (L.) chagasi isolate (Table 6A), between eight strains of L. (L.) donovani derived from patients in the same endemic region of Bihar State, India (Table 6B), and between four L. (L.) tropica isolates recently derived from infected humans in the Middle East (Table 6C). L. tropica isolates were kindly provided by Dr. F. Steurer of the Centers for Diseases Control. kDNA copy numbers were normalized to the DNA polymerase I gene, which is a single copy gene in the parasite genome. Relative copy numbers were calculated using the delta delta CT method.

TABLE 6

(A) The relative copy number difference in kinetoplast mini- and maxicircle sequences between the indicated Leishmania donovani complex species. Expression changes are relative to the (*) indicated sample. (B) The relative copy number of maxi- or minicircle DNA is indicated between 8 isolates of L. donovani and (C) 5 isolates of L. tropica.

| Leishmania species | Maxicircle | Minicircle |
|---|---|---|
| (A) L. donovani complex | | |
| L. (L.) chagasi | 6.75 | 4.21 |
| L. (L.) chagasi (attenuated) | 4.36 | 1.85 |
| L. (L.) donovani | 2.34 | 7.19 |
| L. (L.) infantum* | 1.00 | 1.00 |
| Mean ± SE fold increase | 3.6 ± 1.45 | 3.5 ± 1.6 |
| (B) L. donovani isolates | | |
| L. (L.) donovani (reference)* | 1.00 | 1.00 |
| L. (L.) donovani 1 | 0.38 | 0.21 |
| L. (L.) donovani 2 | 0.23 | 0.16 |
| L. (L.) donovani 3 | 0.39 | 0.23 |
| L. (L.) donovani 4 | 1.72 | 0.66 |
| L. (L.) donovani 5 | 0.41 | 0.23 |
| L. (L.) donovani 6 | 0.99 | 1.80 |
| L. (L.) donovani 7 | 0.56 | 1.03 |
| Mean ± SE fold decrease/increase | 2.2 ± 0.4 | 3.1 ± 0.8 |
| (C) L. tropica isolates | | |
| L. (L.) tropica 1* | 1.00 | 1.00 |
| L. (L.) tropica 2 | 1.99 | 1.53 |
| L. (L.) tropica 3 | 4.25 | 5.64 |
| L. (L.) tropica 4 | 3.92 | 2.76 |
| L. (L.) tropica 5 | 1.04 | 1.72 |
| Mean ± SE fold increase | 2.4 ± 0.8 | 2.5 ± 0.9 |

These data showed that there are indeed differences between the copy numbers of maxi- or minicircle DNA both between species and between isolates within a single species. The minicircle or maxicircle copy numbers varied by 2.53±0.92 or 2.44±0.78-fold (average±SE), respectively, between different isolates of L. tropica (Table 6C). Mini- or maxicircle copy numbers differed by 3.13±0.77 or 2.18±0.41-fold, respectively, between different isolates of L. donovani (Table 6B). Although we did not compare all Leishmania species listed in Tables 1 and 3, there were differences in maxi- or minicircle copy numbers between the 3 species tested (3.61±1.45 or 3.56±1.60, respectively).

Figure 3:
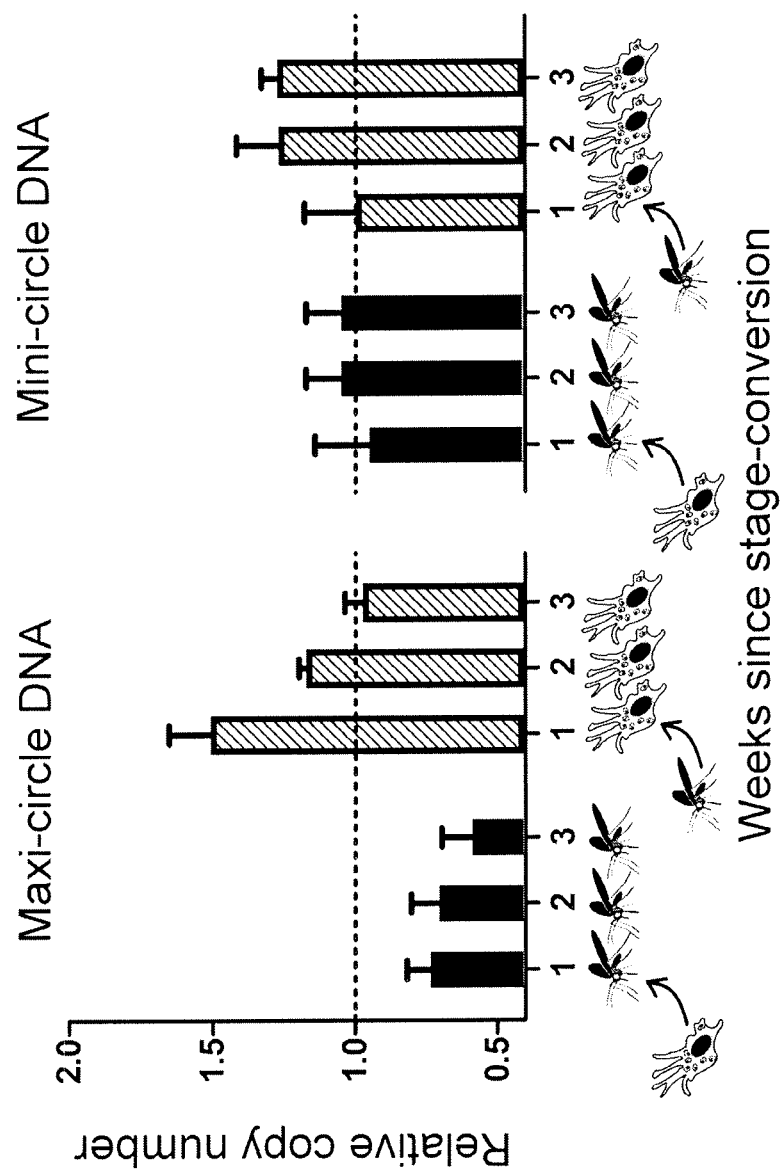
FIG. 3. kDNA copy numbers during stage transition. Maxicircle (left) or minicircle (right) kDNA primer pairs were used to quantify copy numbers in the promastigote and amastigote life stages when converting in vitro between the two life stage forms. Solid bars: Total parasite DNA was extracted from amastigotes to determine basal expression, and then weekly after in vitro conversion to promastigotes for comparison. Striped bars: Total parasite DNA was extracted from promastigotes to use as baseline, and then weekly after in vitro conversion to amastigotes for comparison. kDNA abundance was normalized to the single copy gene DNA polymerase I, and expressed as fold change in promastigotes (sold bars) or amastigotes (striped bars) relative to the pre-conversion stage.

As a means of addressing changes in kDNA copy numbers during stage transition, we applied the same technique to an L. (L.) chagasi strain capable of transforming between promastigote and axenic amastigote in culture. Mini- and maxicircle copies were quantified weekly during the conversion from promastigote to amastigote, or from amastigote to promastigote, in response to culture conditions inducing stage transition (FIG. 3). At the week one time-point there was no significant difference between minicircle copies as parasites converted either from amastigote to promastigote or from promastigote to amastigote (p>0.1, n=3; two-tailed T-test assuming unequal variances). Maxicircle copies underwent a greater fold change although this did not reach significance. One week after the transition from amastigote to promastigote, newly transformed promastigotes contained 0.74 fold fewer copies of maxicircles than the amastigote baseline (solid bar week 1; p=0.09, N=3). Conversely, one week after conversion from promastigotes, axenic amastigotes contained 1.50 fold higher numbers of maxicircle copies than the baseline in promastigotes (striped bar week 1; p=0.08, N=3). Although axenic amastigotes are not identical to tissue-derived amastigotes, these findings suggest that standard curves generated from promastigote-derived DNA, particularly using minicircle kDNA probes, can be validly applied to quantification of amastigotes of the same species/strain.

Detection of *L. donovani* in Clinical and Other Unknown Isolates.

Figure 4:
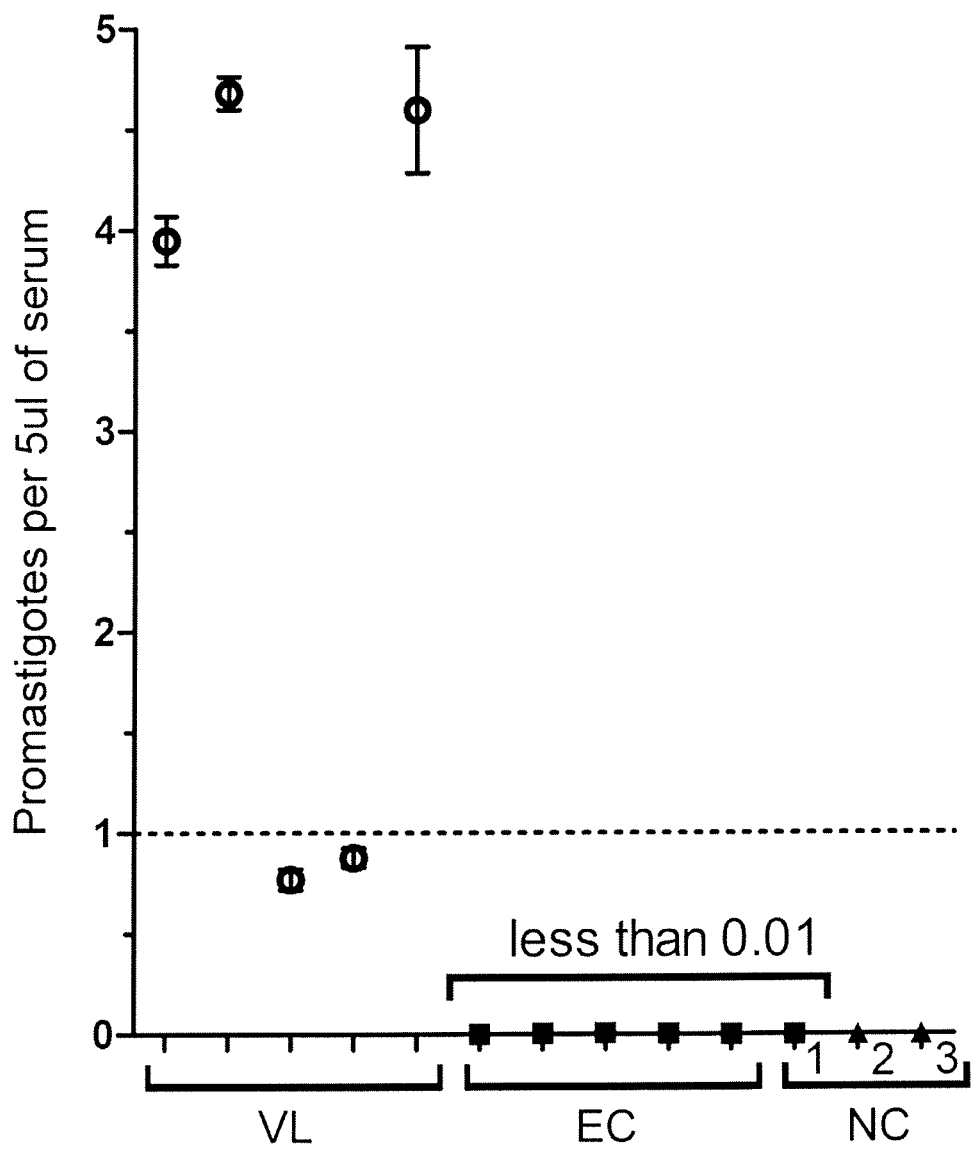
FIG. 4. qPCR detection of L. (L.) donovani in human sera. DNA extracted from 200 µl of serum was used to detect and quantify Leishmania DNA in five VL patients from Bangladesh (VL). The low numbers of parasites detected may either be the result of whole parasites being sampled or lysed parasite DNA floating in peripheral blood. Non-VL endemic control (EC) patients and donor serum without exposure to Leishmania (NC 1) showed no evidence of infection. Other negative controls (NC) were a human DNA template NC 2 and water NC 3.

SYBR green based qPCR assays were applied to serum samples from patients with visceral leishmaniasis (VL) caused by *L. donovani*, and control patients undergoing treatment for other diseases (non-VL) (FIG. 4). A priori, serum specimens would be expected to be cell-free, and therefore not contain DNA from intracellular *Leishmania* spp. parasites. Nonetheless, if there were inapparent lysis of leukocytes during blood collection, DNA could be present. Indeed, there was DNA extracted from serum specimens, and these were positive for *Leishmania* DNA in all five patients with VL, using the kDNA 3 SYBR green assay (FIG. 4). All negative controls were negative for parasite DNA, including five control Bangladeshi subjects, one individual from Iowa, and control human DNA from a North American subject. Parasites were quantified in all positive subjects, revealing 595±178 (standard error) *Leishmania* parasites per ml of serum.

Serial qPCR was used to speculate parasites from a different type of clinical specimens, i.e. cutaneous biopsies for diagnosis of cutaneous leishmaniasis. Biopsy specimens are routinely obtained for diagnostic evaluation of cutaneous ulcers that are suspected to be cutaneous leishmaniasis in clinical settings in northeast Brazil. To evaluate the serial qPCR for diagnosis/speciation using these specimens, DNA was extracted from the biopsies of three patients living in a region of the state of Bahia, Brazil where *L.* (V.) *braziliensis* and *L.* (L.) *amazonensis* have been endemic (5,60). Extracted DNA samples from all three patient biopsies were tested by serial qPCR as in FIG. 2, and all three were positive for the presence *L. Viannia* spp. according to the *L.* (V.) *braziliensis* kDNA 3 probe pair. We tested an additional 11 DNA samples extracted from parasites isolated from cutaneous lesions of subjects living in Manaus, Amazonas, Brazil, as well as 19 DNA samples from different clinical forms of tegumentary leishmaniasis from Corte de Pedra, Bahia, Brazil (6 from cutaneous, 7 from disseminated, and 6 from mucosal leishmaniasis). *L.* (V.) *braziliensis* kDNA 3 amplified members of the *L. Viannia* spp. subgenus regardless of species. Furthermore, all 19 isolates from subjects in Corte de Pedra amplified with the primer sets SLACS (31), which has specifically amplified *L.* (V.) *braziliensis* from among the *Viannia* sub-genus, suggesting that these samples were *L.* (V.) *braziliensis*, as opposed to *L.* (V.) *guyanensis* or *L.* (V.) *panamensis*. These data also suggested that the SLACS genes were present regardless of clinical form. None of the 11 samples from Manaus were amplified by the SLACS primer set, indicating that these 11 isolates were *Leishmania Viannia* sub-genus, but not *L.* (V.) *braziliensis*.

The presence LRV1 RNA viruses in *L.* (V.) *guyanensis* has been recently reported to be associated with distinct clinical presentations of disease (31). It was of interest to consider whether retrotransposons might also be a biomarker for the clinical presentation of symptomatic infections with *Leishmania* subgenus *Viannia braziliensis* infections. However, no significant differences in SLACS genomic copy numbers were observed between isolates with different clinical presentations (tested via delta-delta CT method relative to the genomic *L.* (V.) *braziliensis* DNA polymerase 2 primer set, according to a student's T-tests at p<0.05 between each clinical presentation).

Five DNA samples originally obtained from patients in different regions of the world were tested as unknowns using the serial qPCR assay. No information about geographic location or species was provided at the time of serial qPCR testing. Species identification of the isolates, determined at the Centers for Diseases Control by isoenzyme testing, indicated they were *L.* (V.) *braziliensis*, *L.* (L.) *donovani*, *L.* (L.) *infantum*, *L.* (L.) *mexicana*, and *L.* (L.) *major*. Using the qPCR primer pair selection strategy outlined in Table 5, the species identified through the qPCR serial testing corresponded to the species designation according to isoenzyme analysis for all 5 unknowns. Primer sets used in this analysis were kDNA 1, *L.* (V.) *braziliensis* kDNA 3, MSP associated gene 1 (MAG 1), and *L.* (L.) *mexicana* mini-circle 1.

Discussion

The global burden of leishmaniasis is high (19). Visceral leishmaniasis has reached epidemic proportions in three regions (Bangladesh/Nepal/Bihar State, India, southern Sudan-Ethiopia/Afghanistan and Brazil). Drug resistance has further augmented the disease burden in northern India (12), and the HIV epidemic has led to new patterns of visceral leishmaniasis in Spain and Portugal (3). Across the ocean, urbanization has caused spread of visceral leishmaniasis in peri-urban settings of northeast and southern Brazil (32). Cutaneous leishmaniasis is highest in the Middle East, Syria, Brazil and Peru (66), but imported cutaneous leishmaniasis is becoming problematic in the USA particularly in military personnel (1,59). Leishmaniasis in the blood supply is becoming a concern (11,51), and an outbreak of *Leishmania* (L.) *infantum* infection has affected foxhounds has introduced a possible reservoir into the USA (54). As such, leishmaniasis is emerging as a concerning disease of both human and veterinary importance.

Diagnostic testing for leishmaniasis is less than optimal. The need for improved diagnostic procedures is prominent in the current setting of expanding disease burden. Clinical presentation and a positive test of immune response to the parasite (serology during visceral leishmaniasis or *Leishmania* skin testing during cutaneous leishmaniasis) can be suggestive, but definitive diagnosis requires parasite identification. The latter can be in the form of microscopic examination of tissue biopsies, bone marrow or splenic aspirates, and/or cultivation of live organisms from clinical tissue specimens. The sensitivity is variable with the specimen source. Microscopic exam and culture from splenic aspirate has >95% and close to 100% sensitivity for diagnosis of Indian kala azar, respectively, but the procedure is risky in all but a few clinicians' hands. The sensitivity of bone marrow aspirate is lower (52-69%) but the procedure is safer albeit still invasive (8, 45, 47, 69). Microscopic identification and/or culture from biopsied cutaneous lesions is less sensitive and very dependent on the disease form, with parasites isolated from only 30-50% of localized cutaneous ulcers and rarely isolated from lesions mucosal or disseminated leishmaniasis. The species of Leishmania is most commonly differentiated by electrophoretic mobility of isoenzymes from cultured promastigotes (65), a lengthy method that is only feasible if parasites are isolated in culture.

Molecular methods to detect Leishmania spp. DNA include hybridization of infected tissues (18) and amplification using routine PCR (polymerase chain reaction), PCR-ELISA, (36, 55, 57), (14) or quantitative PCR (41, 49, 64). These methods have been successfully applied for detection of individual Leishmania species in clinical samples, including peripheral blood leukocytes of patients with visceral leishmaniasis or asymptomatic infection (39, 50, 61). Discrimination between the Leishmania species has been reported using RAPD (random amplification of polymorphic DNA) (27) and qPCR. Species-discriminating qPCR assays that can distinguish between the two Leishmania subgenuses Viannia and Leishmania, between Leishmania complexes (L. (L.) mexicana, L. (L.) donovani/infantum, L. (L.) major) or between L. (L.) donovani strains (56) have been reported. Despite many reports, a standardized rapid and sensitive test that distinguishes the spectrum of common Leishmania species is still needed (48).

The purpose of this study was to develop a comprehensive series of qPCR assays adequate for detection and speciation of Leishmania spp. in clinical, environmental or experimental samples. To approach this goal, we chose qPCR targets that were multi-copy genes, or reported targets for conventional or quantitative PCR in the literature. Targets included kinetoplast minicircle DNA (49,64), other repetitive sequences such as rRNA coding or intergenic spacer regions, and single copy genes including those encoding DNA polymerase (9) or glucose phosphate isomerase (68). From these we designed a series of primers and probes that were then tested for their sensitivity and specificity to detect eight different Leishmania species. All assays retained specificity in the presence of 10-fold excess human DNA.

As expected, multi-copy targets were the most sensitive assays for detection of Leishmania spp. DNA. The most efficient was minicircle kDNA, although the sensitivity of individual kDNA primer sets differed between Leishmania species. A combination of two kDNA primers was finally chosen (kDNA1, L. (V.) braziliensis kDNA 3) to detect all Leishmania spp., with the latter used to detect L. (V.) braziliensis alone. Species discrimination was approached starting with the melt curve information from the kDNA1 primer set. The MAUI primer set could be used to differentiate L. (L.) donovani from L. (L.) infantum chagasi. Identification of L. (L.) amazonensis could be confirmed with the L. (L.)amazonensis kDNA 2 primer set. The L. mexicana minicircle 1 primer set was found to differentiate L. mexicana from L. major. If the above led to ambiguity regarding species identification, a number of other primer sets could be employed, with melt-curve criteria used for species differentiation as shown in FIG. 1. Thus, detection and speciation can be achieved using SYBR green alone, without a need for expensive TaqMan probes. Thus, the sets should provide enough flexibility to detect and differentiate infections with Leishmania isolates in many clinical specimens.

In addition to the above SYBR green assays, we also tested several Taqman probes and primer sets. These could be used to provide additional validation of findings in problematic cases. Furthermore, at least some of these can be developed into multiplex assays for detection/species determination, illustrated by the ability of a multiplex assay containing MSP associated gene 2 and DNA polymerase 2 Taqman primer pairs to distinguish visceralizing species from all other Leishmania species (Table 3).

There are a few reports documenting individuals with symptoms resembling visceral leishmaniasis, from whom Leptomonas has been isolated alone or in combination with L. donovani (62). Whether these are primary causes of disease or coinfections is not yet clear. Therefore we incorporated Leptomonas into our set of primers and probes. GAPDH and repetitive mini-exon sequences were sufficient to identify and quantify Leptomonas species. Although Leptomonas GAPDH 2 primer sets also amplified L. braziliensis, Leptomonas mini-exon 1 did not, making these primer sets useful even in the case of Leptomonas-Leishmania spp. co-infections.

Because of a need to quantify parasites in clinical specimens using the most sensitive primer sets, we investigated the validity of minicircle primer for comparison of clinical samples with standard curves of promastigote DNA. Therefore we applied qPCR tests using primers for mini- or maxicircles, normalized to a single copy gene (DNA polymerase I), to compare kDNA copy numbers between the promastigote and amastigote life stages, between different strains of individual Leishmania species, and between different species of Leishmania.

There were not significant differences between copy numbers of either mini- or maxicircle DNA between the promastigote and the amastigote stages, suggesting the use of promastigote DNA to quantify amastigotes in mammalian specimens would be valid. However copy numbers differed moderately between strains of the same species, and even more between different species of the Leishmania donovani complex. The latter conclusions are complicated by the expected variability of primer hybridization to kDNA of different species. We conclude that the use of minicircle primer sets for quantification might be most accurate by comparison with a curve generated using DNA from the same species, but absolute numbers would not be as accurate as quantification based on a chromosomal gene target. Logically it seems valid to use the kDNA primer set for relative quantification in a single patient to follow response to therapy, or in a single household or family that might share parasite strains. However caution must be used in comparing absolute parasite numbers between isolates or species using kDNA primers.

In conclusion, we report herein a series of qPCR assays that is sufficient to identify and speculate parasite DNA in serum samples from patients with visceral leishmaniasis or lesion biopsies of subjects with tegumentary leishmaniasis. The validation using SYBR green makes this a rapid and relatively inexpensive means of detecting, quantifying and determining the species of Leishmania in clinical or epidemiologic samples. In addition to diagnosis, additional useful applications could include quantitative analysis of parasites in buffy coat or serum specimens to document response to therapy, species determination in tissue biopsies or tissues scraped from microscopic slides, and studies of parasite loads in sand flies from endemic regions. The qPCR serial testing strategy requires a reference lab with the technical capacity to perform qPCR. This technology is becoming available in many countries and could be developed in a central diagnostic laboratory in endemic countries.

Example 2

*L. amazonensis*
Melt-Curve Analysis

Melt-curve analysis with the SYBR green primer set TCGAGATCGACGCGTTGTT (SEQ ID NO:65) and CCGCACAGCTCCTCGAA (SEQ ID NO:66) (HSP70-4 forward and reverse, respectively) can be used to distinguish *L. amazonensis* from the species *L. tropica*. Melt-curve analysis with the SYBR green primer set GGGTAGGGGCGTTCTGC (SEQ ID NO:13) and TACACCAACCCCCAGTTTGC (SEQ ID NO:14) (*L. amazonensis* kDNA 3 forward and reverse, respectively) can be used to distinguish *L. amazonensis* from both *L. major* and *L. mexicana*. Melt-curve analysis with the SYBR green primer set CACATATTTTAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) can be used to distinguish *L. amazonensis* from the species *L. major*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. amazonensis* from both *L. major* and *L. mexicana*.

SYBR Green Amplification

The SYBR green primer set GAGGTGTTTGCCCGCATC (SEQ ID NO:41) and CTCGCCCATGTCGTCG (SEQ ID NO:42) (Alpha-tubulin 1 forward and reverse, respectively) was capable of discriminating *L. amazonensis* from the species *L. braziliensis*, which did not amplify. The primer set, using SYBR green chemistry, GGTCCCGGCCCAAACTTTTC (SEQ ID NO:9) and CCGGGGTTTCGCACTCATTT (SEQ ID NO:10) (*L. amazonensis* kDNA 1 forward and reverse, respectively) was useful in distinguishing *L. amazonensis* from the species *L. chagasi*, and *L. tropica*, for which no amplification occurred. The SYBR green primer set GGTAGGGGCGTTCTGCAAT (SEQ ID NO:11) and CCCGGCCTATTTTACACCAACC (SEQ ID NO:12) (*L. amazonensis* kDNA 2 forward and reverse, respectively) was useful in distinguishing *L. amazonensis* from the species *L. chagasi*, and *L. braziliensis*, for which no amplification occurred. The SYBR green primer set TGAGTGCAGAAACCCCGTTCATA (SEQ ID NO:15) and ACACCAACCCCCAGTTGTGA (SEQ ID NO:16) (*L. amazonensis* kDNA 4 forward and reverse, respectively) was capable of discriminating *L. amazonensis* from the species *L. chagasi, L. donovani, L. infantum, L. major*, and *L. braziliensis*, none of which amplified. The SYBR green primer set ACGGGGTTTCTGCACCCATT (SEQ ID NO:19) and GTAGGGGCGTTCTGCGAAAA (SEQ ID NO:20) (*L. major* Minicircle 1 forward and reverse, respectively) was capable of discriminating *L. amazonensis* from the species *L. tropica*, which did not amplify. The primer set, using SYBR green chemistry, CACATATTTTAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was useful in distinguishing *L. amazonensis* from the species *L. braziliensis*, which did not amplify.

Taqman Amplification

The Taqman primer/probe set GAGGTGTTTGCCCGCATC (SEQ ID NO:41), CTCGCCCATGTCGTCG (SEQ ID NO:42), and TGAGGGCATGGAGGAGGGCG (SEQ ID NO:90) (Alpha-tubulin 1 forward, reverse, and probe, respectively) was useful in distinguishing *L. amazonensis* from the species *L. braziliensis*, which did not amplify.

*L. chagasi*
Melt-Curve Analysis

Melt-curve analysis with the SYBR green primer set GGGTAGGGGCGTTCTGC (SEQ ID NO:13) and TACACCAACCCCCAGTTTGC (SEQ ID NO:14) (*L. amazonensis* kDNA 3 forward and reverse, respectively) can be used to distinguish *L. chagasi* from both *L. major* and *L. mexicana*. Melt-curve analysis with the SYBR green primer set GTCGTTGTCCGTGTCGCTGT (SEQ ID NO:59) and CGCTGTGTGTGTCCGTGTGT (SEQ ID NO:60) (*L. major* MSP associated gene 1 (*L. major* MAG 1) forward and reverse, respectively) can be used to distinguish *L. chagasi* from the species *L. donovani*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. chagasi* from both *L. major* and *L. mexicana*. The SYBR green primer set AGAGCGTGCCTTGGATTGTG (SEQ ID NO:49) and CGCTGCGTTGATTGCGTTG (SEQ ID NO:50) (MSP associated gene 1 forward and reverse, respectively) can be used to distinguish *L. chagasi* from the species *L. donovani*.

SYBR Green Amplification

The SYBR green primer set GAGGTGTTTGCCCGCATC (SEQ ID NO:41) and CTCGCCCATGTCGTCG (SEQ ID NO:42) (Alpha-tubulin 1 forward and reverse, respectively) was capable of discriminating *L. chagasi* from the species *L. braziliensis*, which did not amplify. The primer set, using SYBR green chemistry, ATTTTAGTATGAGTGGTAGGTTTTGTT (SEQ ID NO:27) and CAATAACTGGGACGGTTGCT (SEQ ID NO:28) (Cytochrome B 1 forward and reverse, respectively) was useful in distinguishing *L. chagasi* from the species *L. amazonensis, L. major, L. mexicana*, and *L. braziliensis*, none of which amplified. The primer set, using SYBR green chemistry, CGACCCTGTCACCACCACAG (SEQ ID NO:53) and GAGGCCACCCTATCGCTGAC (SEQ ID NO:54) (*L. chagasi* SIDER repeat 1 forward and reverse, respectively) was useful in distinguishing *L. chagasi* from the species *L. amazonensis, L. major*, and *L. braziliensis*, for which no amplification occurred. The SYBR green primer set TCCGCAGGAGACTTCGTATG (SEQ ID NO:103) and CACGACTATCCACCCCATCC (SEQ ID NO:104) (*L. infantum* Minicircle 1 forward and reverse, respectively) was capable of discriminating *L. chagasi* from the species *L. amazonensis, L. donovani, L. major, L. mexicana*, and *L. braziliensis*, for which no amplification occurred. The SYBR green primer set ACGGGGTTTCTGCACCCATT (SEQ ID NO:19) and GTAGGGGCGTTCTGCGAAAA (SEQ ID NO:20) (*L. major* Minicircle 1 forward and reverse, respectively) was useful in distinguishing *L. chagasi* from the species *L. tropica*, which did not amplify. The primer set, using SYBR green chemistry, TCAGGTTGCTTACTACGTGTTTATGGTG (SEQ ID NO:33) and TGCTAAACAAACACCACATATGATCTGC (SEQ ID NO:34) (*L. tropica* Cytochrome B 2 forward and reverse, respectively) was useful in distinguishing *L. chagasi* from the species *L. amazonensis, L. major*, and *L. braziliensis*, none of which amplified. The primer set, using SYBR green chemistry, ACGTCGCCAACTGCTTCACC (SEQ ID NO:57) and GTGTTCGCACCGCCTTGAC (SEQ ID NO:58) (*L. braziliensis* DNA polymerase 2 forward and reverse, respectively) was useful in distinguishing *L. chagasi* from the species *L. major*, which did not amplify. The primer set, using SYBR green chemistry, AGAGCGTGCCTTGGATTGTG (SEQ ID NO:49) and CGCTGCGTTGATTGCGTTG (SEQ ID NO:50) (MSP Associated Gene 1 (MAG 1) forward and reverse, respectively) was capable of discriminating *L. chagasi* from the species *L. amazonensis, L. major*, and *L. braziliensis*, for which no amplification occurred. The SYBR green primer set AGTTTTGGTTGGCGCTCCTG (SEQ ID NO:51) and CCCACTCGCTTTCCTTGGTC (SEQ ID NO:52) (MSP Associated Gene 2 (MAG 2) forward and reverse, respectively) was useful in distinguishing *L. chagasi* from the species *L. amazonensis, L. major, L. mexicana*, and *L. braziliensis*, for which no amplification occurred. The SYBR green primer set GCTTGGTTGGATTAT-TTTTGCTG (SEQ ID NO:39) and AACAACATTT-TAACTCTTGTAGGATTCG (SEQ ID NO:40) (Maxicircle 1 forward and reverse, respectively) was useful in distinguishing *L. chagasi* from the species *L. amazonensis, L. major, L. mexicana*, and *L. braziliensis*, none of which amplified.

Taqman Amplification

The Taqman primer and probe set GAGGTGTTTGCCCGCATC (SEQ ID NO:41), CTCGCC-CATGTCGTCG (SEQ ID NO:42), and TGAGGGCATG-GAGGAGGGCG (SEQ ID NO:90) (Alpha-tubulin 1 forward, reverse, and probe, respectively) was useful in distinguishing *L. chagasi* from the species *L. braziliensis*, which did not amplify. The Taqman primer/probe set ATTT-TAGTATGAGTGGTAGGTTTTGTT (SEQ ID NO:27), CAATAACTGGGACGGTTGCT (SEQ ID NO:28), and CCATGTACGATGATGTCGTATTGAGGTCTAACA (SEQ ID NO:88) (Cytochrome B 1 forward, reverse, and probe, respectively) was capable of discriminating *L. chagasi* from the species *L. amazonensis, L. major, L. mexicana*, and *L. braziliensis*, for which no amplification occurred. The Taqman primer and probe set GGGTGCAGAAATCCCGTTCA (SEQ ID NO:5), CCCGGCCCTATTTTACACCA (SEQ ID NO:6), and ACCCCCAGTTTCCCGCCCCG (SEQ ID NO:83) (kDNA 4 minicircle forward, reverse, and probe, respectively) was useful in distinguishing *L. chagasi* from the species *L. amazonensis, L. major, L. mexicana*, and *L. braziliensis*, for which no amplification occurred. The Taqman primer/probe set AATGGGTGCAGAAATCCCGTTC (SEQ ID NO:7), CCACCACCCGGCCCTATTTTAC (SEQ ID NO:8), and CCCCAGTTTCCCGCCCCGGA (SEQ ID NO:84) (kDNA 7 minicircle forward, reverse, and probe, respectively) was useful in distinguishing *L. chagasi* from the species *L. amazonensis, L. mexicana*, and *L. braziliensis*, none of which amplified.

*L. donovani*

Melt-Curve Analysis

Melt-curve analysis with the SYBR green primer set GGGTAGGGGCGTTCTGC (SEQ ID NO:13) and TACAC-CAACCCCCAGTTTGC (SEQ ID NO:14) (*L. amazonensis* kDNA 3 forward and reverse, respectively) can be used to distinguish *L. donovani* from the species *L. major*. Melt-curve analysis with the SYBR green primer set GTCGTTGTCCGTGTCGCTGT (SEQ ID NO:59) and CGCTGTGTGTGTCCGTGTGT (SEQ ID NO:60) (*L. major* MSP associated gene 1 (*L. major* MAG 1) forward and reverse, respectively) can be used to distinguish *L. donovani* from both *L. chagasi* and *L. infantum*. Melt-curve analysis with the SYBR green primer set CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) can be used to distinguish *L. donovani* from the species *L. major*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. donovani* from the species *L. major*. The SYBR green primer set AGAGCGTGCCTTGGATTGTG (SEQ ID NO:49) and CGCTGCGTTGATTGCGTTG (SEQ ID NO:50) (MSP associated gene 1 forward and reverse, respectively) can be used to distinguish *L. donovani* from both *L. chagasi* and *L. infantum*.

SYBR Green Amplification

The SYBR green primer set GAGGTGTTTGCCCG-CATC (SEQ ID NO:41) and CTCGCCCATGTCGTCG (SEQ ID NO:42) (Alpha-tubulin 1 forward and reverse, respectively) was useful in distinguishing *L. donovani* from the species *L. braziliensis*, which did not amplify. The primer set, using SYBR green chemistry, ATTTTAGTAT-GAGTGGTAGGTTTTGTT (SEQ ID NO:27) and CAATAACTGGGACGGTTGCT (SEQ ID NO:28) (Cytochrome B 1 forward and reverse, respectively) was useful in distinguishing *L. donovani* from the species *L. amazonensis, L. major, L. mexicana*, and *L. braziliensis*, for which no amplification occurred. The primer set, using SYBR green chemistry, CGACCCTGTCACCACCACAG (SEQ ID NO:53) and GAGGCCACCCTATCGCTGAC (SEQ ID NO:54) (*L. chagasi* SIDER repeat 1 forward and reverse, respectively) was capable of discriminating *L. donovani* from the species *L. amazonensis, L. major*, and *L. braziliensis*, for which no amplification occurred. The primer set, using SYBR green chemistry, GCGGTGGCTGGTTTTA-GATG (SEQ ID NO:25) and TCCAATGAAGC-CAAGCCAGT (SEQ ID NO:26) (*L. donovani* Minicircle 1 forward and reverse, respectively) was useful in distinguishing *L. donovani* from the species *L. amazonensis, L. major, L. mexicana*, and *L. braziliensis*, none of which amplified. The primer set, using SYBR green chemistry, ACGGGGTTTCTGCACCCATT (SEQ ID NO:19) and GTAGGGGCGTTCTGCGAAAA (SEQ ID NO:20) (*L. major* Minicircle 1 forward and reverse, respectively) was capable of discriminating *L. donovani* from the species *L. tropica*, which did not amplify. The primer set, using SYBR green chemistry, CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was capable of discriminating *L. donovani* from the species *L. braziliensis*, which did not amplify. The primer set, using SYBR green chemistry, ACGTCGC-CAACTGCTTCACC (SEQ ID NO:57) and GTGTTCGCACCGCCTTGAC (SEQ ID NO:58) (*L. braziliensis* DNA polymerase 2 forward and reverse, respectively) was capable of discriminating *L. donovani* from the species *L. major*, which did not amplify. The SYBR green primer set AGAGCGTGCCTTGGATTGTG (SEQ ID NO:49) and CGCTGCGTTGATTGCGTTG (SEQ ID NO:50) (MSP Associated Gene 1 (MAG 1) forward and reverse, respectively) was useful in distinguishing *L. donovani* from the species *L. amazonensis, L. major*, and *L. braziliensis*, none of which amplified. The SYBR green primer set AGTTTTGGTTGGCGCTCCTG (SEQ ID NO:51) and CCCACTCGCTTTCCTTGGTC (SEQ ID NO:52) (MSP Associated Gene 2 (MAG 2) forward and reverse, respectively) was capable of discriminating *L. donovani* from the species *L. amazonensis, L. major, L. mexicana*, and *L. braziliensis*, for which no amplification occurred. The primer set, using SYBR green chemistry, GCTTGGTTGGATTATTTTTGCTG (SEQ ID NO:39) and AACAACATTTTAACTCTTGTAGGATTCG (SEQ ID NO:40) (Maxicircle 1 forward and reverse, respectively) was capable of discriminating *L. donovani* from the species *L. amazonensis, L. major, L. mexicana*, and *L. braziliensis*, none of which amplified.

Taqman Amplification

The Taqman primer/probe set GAGGTGTTTGCCCGCATC (SEQ ID NO:41), CTCGCCCATGTCGTCG (SEQ ID NO:42), and TGAGGGCATGGAGGAGGGCG (SEQ ID NO:90) (Alpha-tubulin 1 forward, reverse, and probe, respectively) was capable of discriminating *L. donovani* from the species *L. braziliensis*, which did not amplify. The Taqman primer/probe set ATTTTAGTATGAGTGGTAGGTTTTGTT (SEQ ID NO:27), CAATAACTGGGACGGTTGCT (SEQ ID NO:28), and CCATGTACGATGATGTCGTATTGAGGTCAACA (SEQ ID NO:88) (Cytochrome B 1 forward, reverse, and probe, respectively) was useful in distinguishing *L. donovani* from the species *L. amazonensis, L. major, L. mexicana*, and *L. braziliensis*, none of which amplified. The Taqman primer and probe set GGGTGCAGAAATCCCGTTCA (SEQ ID NO:5), CCCGGCCCTATTTTACACCA (SEQ ID NO:6), and ACCCCCAGTTTCCCGCCCCG (SEQ ID NO:83) (kDNA 4 minicircle forward, reverse, and probe, respectively) was useful in distinguishing *L. donovani* from the species *L. amazonensis, L. major, L. mexicana*, and *L. braziliensis*, for which no amplification occurred. The Taqman primer and probe set AATGGGTGCAGAAATCCCGTTC (SEQ ID NO:7), CCACCACCCGGCCCTATTTTAC (SEQ ID NO:8), and CCCCAGTTTCCCGCCCCGGA (SEQ ID NO:84) (kDNA 7 minicircle forward, reverse, and probe, respectively) was capable of discriminating *L. donovani* from the species *L. amazonensis, L. mexicana*, and *L. braziliensis*, none of which amplified.

*L. infantum*
Melt-Curve Analysis

Melt-curve analysis with the SYBR green primer set GGGTAGGGGCGTTCTGC (SEQ ID NO:13) and TACACCAACCCCCAGTTTGC (SEQ ID NO:14) (*L. amazonensis* kDNA 3 forward and reverse, respectively) can be used to distinguish *L. infantum* from both *L. major* and *L. mexicana*. Melt-curve analysis with the SYBR green primer set GTCGTTGTCCGTGTCGCTGT (SEQ ID NO:59) and CGCTGTGTGTGTCCGTGTGT (SEQ ID NO:60) (*L. major* MSP associated gene 1 (*L. major* MAG 1) forward and reverse, respectively) can be used to distinguish *L. infantum* from the species *L. donovani*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. infantum* from both *L. major* and *L. mexicana*. Melt-curve analysis with the SYBR green primer set GGGTAGGGGCGTTCTGC (SEQ ID NO:3) and CCCGGCCTATTTTACACCAACC (SEQ ID NO:4) (kDNA 3 minicircle forward and reverse, respectively) can be used to distinguish *L. infantum* from the species *L. mexicana*. The SYBR green primer set AGAGCGTGCCTTGGATTGTG (SEQ ID NO:49) and CGCTGCGTTGATTGCGTTG (SEQ ID NO:50) (MSP associated gene 1 forward and reverse, respectively) can be used to distinguish *L. infantum* from the species *L. donovani*.

SYBR Green Amplification

The SYBR green primer set GAGGTGTTTGCCCGCATC (SEQ ID NO:41) and CTCGCCCATGTCGTCG (SEQ ID NO:42) (Alpha-tubulin 1 forward and reverse, respectively) was useful in distinguishing *L. infantum* from the species *L. braziliensis*, which did not amplify. The SYBR green primer set ATTTTAGTATGAGTGGTAGGTTTTGTT (SEQ ID NO:27) and CAATAACTGGGACGGTTGCT (SEQ ID NO:28) (Cytochrome B 1 forward and reverse, respectively) was useful in distinguishing *L. infantum* from the species *L. amazonensis, L. major, L. mexicana*, and *L. braziliensis*, for which no amplification occurred. The SYBR green primer set CGACCCTGTCACCACCACAG (SEQ ID NO:53) and GAGGCCACCCTATCGCTGAC (SEQ ID NO:54) (*L. chagasi* SIDER repeat 1 forward and reverse, respectively) was capable of discriminating *L. infantum* from the species *L. amazonensis, L. major*, and *L. braziliensis*, none of which amplified. The SYBR green primer set ACGGGGTTTCTGCACCCATT (SEQ ID NO:19) and GTAGGGGCGTTCTGCGAAAA (SEQ ID NO:20) (*L. major* Minicircle 1 forward and reverse, respectively) was capable of discriminating *L. infantum* from the species *L. tropica*, which did not amplify. The SYBR green primer set TCAGGTTGCTTACTACGTGTTTATGGTG (SEQ ID NO:33) and TGCTAAACAAACACCACATATGATCTGC (SEQ ID NO:34) (*L. tropica* Cytochrome B 2 forward and reverse, respectively) was useful in distinguishing *L. infantum* from the species *L. amazonensis, L. major*, and *L. braziliensis*, for which no amplification occurred. The SYBR green primer set CACATATTTAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was useful in distinguishing *L. infantum* from the species *L. braziliensis*, which did not amplify. The primer set, using SYBR green chemistry, AGAGCGTGCCTTGGATTGTG (SEQ ID NO:49) and CGCTGCGTTGATTGCGTTG (SEQ ID NO:50) (MSP Associated Gene 1 (MAG 1) forward and reverse, respectively) was useful in distinguishing *L. infantum* from the species *L. amazonensis, L. major*, and *L. braziliensis*, for which no amplification occurred. The SYBR green primer set AGTTTTGGTTGGCGCTCCTG (SEQ ID NO:51) and CCCACTCGCTTTCCTTGGTC (SEQ ID NO:52) (MSP Associated Gene 2 (MAG 2) forward and reverse, respectively) was useful in distinguishing *L. infantum* from the species *L. amazonensis, L. major, L. mexicana*, and *L. braziliensis*, for which no amplification occurred. The primer set, using SYBR green chemistry, GCTTGGTTGGATTATTTTTGCTG (SEQ ID NO:39) and AACAACATTTTAACTCTTGTAGGATTCG (SEQ ID NO:40) (Maxicircle 1 forward and reverse, respectively) was useful in distinguishing *L. infantum* from the species *L. amazonensis, L. major, L. mexicana*, and *L. braziliensis*, for which no amplification occurred.

Taqman Amplification

The Taqman primer and probe set GAGGTGTTTGCCCGCATC (SEQ ID NO:41), CTCGCCCATGTCGTCG (SEQ ID NO:42), and TGAGGGCATGGAGGAGGGCG (SEQ ID NO:90) (Alpha-tubulin 1 forward, reverse, and probe, respectively) was useful in distinguishing *L. infantum* from the species *L. braziliensis*, which did not amplify. The Taqman primer and probe set ATTTTAGTATGAGTGGTAGGTTTTGTT (SEQ ID NO:27), CAATAACTGGGACGGTTGCT (SEQ ID NO:28), and CCATGTACGATGATGTCGTATT-GAGGTCTAACA (SEQ ID NO:88) (Cytochrome B 1 forward, reverse, and probe, respectively) was capable of discriminating *L. infantum* from the species *L. amazonensis, L. major, L. mexicana*, and *L. braziliensis*, none of which amplified. The Taqman primer/probe set GGGTGCAGAAATCCCGTTCA (SEQ ID NO:5), CCCGGCCCTATTTTACACCA (SEQ ID NO:6), and ACCCCCAGTTTCCCGCCCCG (SEQ ID NO:83) (kDNA 4 minicircle forward, reverse, and probe, respectively) was useful in distinguishing *L. infantum* from the species *L. amazonensis, L. major, L. mexicana*, and *L. braziliensis*, none of which amplified. The Taqman primer and probe set AATGGGTGCAGAAATCCCGTTC (SEQ ID NO:7), CCACCACCCGGCCCTATTTTAC (SEQ ID NO:8), and CCCCAGTTTCCCGCCCCGGA (SEQ ID NO:84) (kDNA 7 minicircle forward, reverse, and probe, respectively) was capable of discriminating *L. infantum* from the species *L. amazonensis, L. mexicana*, and *L. braziliensis*, for which no amplification occurred.

*L. major*

Melt-Curve Analysis

Melt-curve analysis with the SYBR green primer set GGTCCCGGCCCAAACTTTTC (SEQ ID NO:9) and CCGGGGTTTCGCACTCATTT (SEQ ID NO:10) (*L. amazonensis* kDNA 1 forward and reverse, respectively) can be used to distinguish *L. major* from the species *L. mexicana*. Melt-curve analysis with the SYBR green primer set GGTAGGGGCGTTCTGCGAAT (SEQ ID NO:11) and CCCGGCCTATTTTACACCAACC (SEQ ID NO:12) (*L. amazonensis* kDNA 2 forward and reverse, respectively) can be used to distinguish *L. major* from the species *L. mexicana*. Melt-curve analysis with the SYBR green primer set GGGTAGGGGCGTTCTGC (SEQ ID NO:13) and TACAC-CAACCCCCAGTTTGC (SEQ ID NO:14) (*L. amazonensis* kDNA 3 forward and reverse, respectively) can be used to distinguish *L. major* from *L. amazonensis, L. chagasi, L. donovani*, and *L. tropica*. Melt-curve analysis with the SYBR green primer set CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) can be used to distinguish *L. major* from both *L. amazonensis* and *L. donovani*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. major* from *L. amazonensis, L. chagasi, L. donovani*, and *L. tropica*.

SYBR Green Amplification

The SYBR green primer set GAGGTGTTTGCCCG-CATC (SEQ ID NO:41) and CTCGCCCATGTCGTCG (SEQ ID NO:42) (Alpha-tubulin 1 forward and reverse, respectively) was capable of discriminating *L. major* from the species *L. braziliensis*, which did not amplify. The SYBR green primer set GGTCCCGGCCCAAACTTTTC (SEQ ID NO:9) and CCGGGGTTTCGCACTCATTT (SEQ ID NO:10) (*L. amazonensis* kDNA 1 forward and reverse, respectively) was useful in distinguishing *L. major* from the species *L. chagasi*, and *L. tropica*, none of which amplified. The primer set, using SYBR green chemistry, GGTAGGGGCGTTCTGCGAAT (SEQ ID NO:11) and CCCGGCCTATTTTACACCAACC (SEQ ID NO:12) (*L. amazonensis* kDNA 2 forward and reverse, respectively) was useful in distinguishing *L. major* from the species *L. chagasi*, and *L. braziliensis*, for which no amplification occurred. The SYBR green primer set ACGGGGTTTCTGCACCCATT (SEQ ID NO:19) and GTAGGGGCGTTCTGCGAAAA (SEQ ID NO:20) (*L. major* Minicircle 1 forward and reverse, respectively) was useful in distinguishing *L. major* from the species *L. tropica*, which did not amplify. The primer set, using SYBR green chemistry, TGACACACATATTT-TAGTGTGGGTGGTAGG (SEQ ID NO:35) and TCCC-CAATAAGACATCATTGTACATGGTAA (SEQ ID NO:36) (*L. tropica* Cytochrome B 3 forward and reverse, respectively) was capable of discriminating *L. major* from the species *L. chagasi, L. infantum*, and *L. braziliensis*, for which no amplification occurred. The primer set, using SYBR green chemistry, CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was capable of discriminating *L. major* from the species *L. braziliensis*, which did not amplify.

Taqman Amplification

The Taqman primer and probe set GAGGTGTTTGCCCGCATC (SEQ ID NO:41), CTCGCC-CATGTCGTCG (SEQ ID NO:42), and TGAGGGCATG-GAGGAGGGCG (SEQ ID NO:90) (Alpha-tubulin 1 forward, reverse, and probe, respectively) was useful in distinguishing *L. major* from the species *L. braziliensis*, which did not amplify. The Taqman primer/probe set AATGGGTGCAGAAATCCCGTTC (SEQ ID NO:7), CCACCACCCGGCCCTATTTTAC (SEQ ID NO:8), and CCCCAGTTTCCCGCCCCGGA (SEQ ID NO:84) (kDNA 7 minicircle forward, reverse, and probe, respectively) was useful in distinguishing *L. major* from the species *L. amazonensis, L. mexicana*, and *L. braziliensis*, for which no amplification occurred.

*L. mexicana*

Melt-Curve Analysis

Melt-curve analysis with the SYBR green primer set GGTCCCGGCCCAAACTTTTC (SEQ ID NO:9) and CCGGGGTTTCGCACTCATTT (SEQ ID NO:10) (*L. amazonensis* kDNA 1 forward and reverse, respectively) can be used to distinguish *L. mexicana* from the species *L. major*. Melt-curve analysis with the SYBR green primer set GGTAGGGGCGTTCTGCGAAT (SEQ ID NO:11) and CCCGGCCTATTTTACACCAACC (SEQ ID NO:12) (*L. amazonensis* kDNA 2 forward and reverse, respectively) can be used to distinguish *L. mexicana* from the species *L. major*. Melt-curve analysis with the SYBR green primer set GGGTAGGGGCGTTCTGC (SEQ ID NO:13) and TACAC-CAACCCCCAGTTTGC (SEQ ID NO:14) (*L. amazonensis* kDNA 3 forward and reverse, respectively) can be used to distinguish *L. mexicana* from *L. amazonensis, L. chagasi*, and *L. tropica*. Melt-curve analysis with the SYBR green primer set GGGTAGGGGCGTTCTGC (SEQ ID NO:1) and TACACCAACCCCCAGTTTGC (SEQ ID NO:2) (kDNA 1 minicircle forward and reverse, respectively) can be used to distinguish *L. mexicana* from *L. amazonensis, L. chagasi*, and *L. tropica*. Melt-curve analysis with the SYBR green primer set GGGTAGGGGCGTTCTGC (SEQ ID NO:3) and CCCGGCCTATTTTACACCAACC (SEQ ID NO:4) (kDNA 3 minicircle forward and reverse, respectively) can be used to distinguish *L. mexicana* from *L. infantum*, and *L. braziliensis*.

SYBR Green Amplification

The primer set, using SYBR green chemistry, GAGGTGTTTGCCCGCATC (SEQ ID NO:41) and CTCGCCCATGTCGTCG (SEQ ID NO:42) (Alpha-tubulin 1 forward and reverse, respectively) was useful in distinguishing *L. mexicana* from the species *L. braziliensis*, which did not amplify. The primer set, using SYBR green chemistry, GGTCCCGGCCCAAACTTTTC (SEQ ID NO:9) and CCGGGGTTTCGCACTCATTT (SEQ ID NO:10) (*L. amazonensis* kDNA 1 forward and reverse, respectively) was useful in distinguishing *L. mexicana* from the species *L. chagasi*, and *L. tropica*, for which no amplification occurred. The SYBR green primer set GGTAGGGGCGTTCTGCGAAT (SEQ ID NO:11) and CCCGGCCTATTTTACACCAACC (SEQ ID NO:12) (*L. amazonensis* kDNA 2 forward and reverse, respectively) was capable of discriminating *L. mexicana* from the species *L. chagasi*, and *L. braziliensis*, none of which amplified. The SYBR green primer set TGAGTGCAGAAACCCCGTT-CATA (SEQ ID NO:15) and ACAC-CAACCCCCAGTTGTGA (SEQ ID NO:16) (*L. amazonensis* kDNA 4 forward and reverse, respectively) was capable of discriminating *L. mexicana* from the species *L. chagasi*, *L. donovani*, *L. infantum*, *L. major*, and *L. braziliensis*, for which no amplification occurred. The SYBR green primer set ACGGGGTTTCTGCACCCATT (SEQ ID NO:19) and GTAGGGGCGTTCTGCGAAAA (SEQ ID NO:20) (*L. major* Minicircle 1 forward and reverse, respectively) was useful in distinguishing *L. mexicana* from the species *L. tropica*, which did not amplify. The SYBR green primer set AATGCGAGTGTTGCCCTTTTG (SEQ ID NO:21) and GCCGAACAACGCCATATTAACC (SEQ ID NO:22) (*L. mexicana* Minicircle 1 forward and reverse, respectively) was capable of discriminating *L. mexicana* from the species *L. amazonensis*, *L. chagasi*, *L. donovani*, *L. infantum*, *L. major*, and *L. braziliensis*, none of which amplified. The SYBR green primer set CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was capable of discriminating *L. mexicana* from the species *L. braziliensis*, which did not amplify.

Taqman Amplification

The Taqman primer/probe set GAGGTGTTTGCCCG-CATC (SEQ ID NO:41), CTCGCCCATGTCGTCG (SEQ ID NO:42), and TGAGGGCATGGAGGAGGGCG (SEQ ID NO:90) (Alpha-tubulin 1 forward, reverse, and probe, respectively) was capable of discriminating *L. mexicana* from the species *L. braziliensis*, which did not amplify.

*L. tropica*

Melt-Curve Analysis

Melt-curve analysis with the SYBR green primer set TCGAGATCGACGCGTTGTT (SEQ ID NO:65) and CCGCACAGCTCCTCGAA (SEQ ID NO:66) (HSP70-4 forward and reverse, respectively) can be used to distinguish *L. tropica* from the species *L. amazonensis*. Melt-curve analysis with the SYBR green primer set GGGTAGGGGCGTTCTGC (SEQ ID NO:13) and TACAC-CAACCCCCAGTTTGC (SEQ ID NO:14) (*L. amazonensis* kDNA 3 forward and reverse, respectively) can be used to distinguish *L. tropica* from both *L. major* and *L. mexicana*. Melt-curve analysis with the SYBR green primer set GGGTAGGGGCGTTCTGC (SEQ ID NO:1) and TACAC-CAACCCCCAGTTTGC (SEQ ID NO:2) (kDNA 1 minicircle forward and reverse, respectively) can be used to distinguish *L. tropica* from both *L. major* and *L. mexicana*. Melt-curve analysis with the SYBR green primer set GGGTAGGGGCGTTCTGC (SEQ ID NO:3) and CCCGGCCTATTTTACACCAACC (SEQ ID NO:4) (kDNA 3 minicircle forward and reverse, respectively) can be used to distinguish *L. tropic* from the species *L. mexicana*.

SYBR Amplification

The primer set, using SYBR green chemistry, GAGGTGTTTGCCCGCATC (SEQ ID NO:41) and CTCGCCCATGTCGTCG (SEQ ID NO:42) (Alpha-tubulin 1 forward and reverse, respectively) was useful in distinguishing *L. tropica* from the species *L. braziliensis*, which did not amplify. The primer set, using SYBR green chemistry, TCAGGTTGCTTACTACGTGTTTATGGTG (SEQ ID NO:33) and TGCTAAACAAACACCACATAT-GATCTGC (SEQ ID NO:34) (*L. tropica* Cytochrome B 2 forward and reverse, respectively) was useful in distinguishing *L. tropica* from the species *L. amazonensis*, *L. major*, and *L. braziliensis*, for which no amplification occurred. The primer set, using SYBR green chemistry, CACATATTT-TAGTGTGGGTGGTAGGTTTTG (SEQ ID NO:37) and TCCCCAATAAGACATCATTGTACATGGTAA (SEQ ID NO:38) (*L. tropica* Cytochrome B 4 forward and reverse, respectively) was useful in distinguishing *L. tropica* from the species *L. braziliensis*, which did not amplify. The primer set, using SYBR green chemistry, GGGGGTTGGTGTAAAATAGGG (SEQ ID NO:23) and ACCACCAGCAGAAGGTCAAAG (SEQ ID NO:24) (*L. tropica* Minicircle 1 forward and reverse, respectively) was capable of discriminating *L. tropica* from the species *L. amazonensis*, *L. chagasi*, *L. donovani*, *L. infantum*, *L. major*, and *L. braziliensis*, for which no amplification occurred.

*L. braziliensis*

Melt-Curve Analysis

Melt-curve analysis with the SYBR green primer set GGGTAGGGGCGTTCTGC (SEQ ID NO:3) and CCCGGCCTATTTTACACCAACC (SEQ ID NO:4) (kDNA 3 minicircle forward and reverse, respectively) can be used to distinguish *L. braziliensis* from the species *L. mexicana*.

SYBR Green Amplification

The primer set, using SYBR green chemistry, TCGTT-GAGGGAGGAGGTGTTTC (SEQ ID NO:55) and TCGGCTTTGAGGTTGGCTTC (SEQ ID NO:56) (*L. braziliensis* DNA polymerase 1 forward and reverse, respectively) was capable of discriminating *L. braziliensis* from the species *L. amazonensis*, *L. chagasi*, *L. donovani*, *L. infantum*, *L. major*, and *L. tropica*, for which no amplification occurred. The SYBR green primer set ACGTCGC-CAACTGCTTCACC (SEQ ID NO:57) and GTGTTCGCACCGCCTTGAC (SEQ ID NO:58) (*L. braziliensis* DNA polymerase 2 forward and reverse, respectively) was capable of discriminating *L. braziliensis* from the species *L. major*, which did not amplify. The SYBR green primer set AATTTCGCAGAACGCCCTAC (SEQ ID NO:17) and GTACTCCCCGACATGCCTCTG (SEQ ID NO:18) (*L. braziliensis* kDNA 1 forward and reverse, respectively) was useful in distinguishing *L. braziliensis* from the species *L. amazonensis*, *L. chagasi*, *L. donovani*, *L. infantum*, *L. major*, and *L. tropica*, none of which amplified. The primer set, using SYBR green chemistry, TGC-TATAAAATCGTACCACCCGACA (SEQ ID NO:101) and GAACGGGGTTTCTGTATGCCATTT (SEQ ID NO:102) (*L. braziliensis* kDNA 3 forward and reverse, respectively) was capable of discriminating *L. braziliensis* from the species *L. amazonensis*, *L. chagasi*, *L. donovani*, *L. infantum*, *L. major*, and *L. tropica*, for which no amplification occurred. The primer set, using SYBR green chemistry, AGAAGCCGGATGTGCTTGTG (SEQ ID NO:71) and GCCCTCAGCCTTCACCTTGT (SEQ ID NO:72) (*Leptomonas* GAPDH 2 forward and reverse, respectively) was capable of discriminating *L. braziliensis* from the species *L. amazonensis*, *L. chagasi*, *L. donovani*, *L. infantum*, *L. major*, and *L. tropica*, none of which amplified. The SYBR green primer set GTGTGGTGGCGGGTGTATGT (SEQ ID NO:47) and GCCCAGGTCGCTGTGAGG (SEQ ID NO:48) (Mini-exon 2 forward and reverse, respectively) was capable of discriminating *L. braziliensis* from the species *L. tropica*, which did not amplify. The primer set, using SYBR green chemistry, GGAGAAACTCACGGCACAGG (SEQ ID NO:67) and GCGCCTCGTAGGTCACAGTT (SEQ ID NO:68) (SLACS forward and reverse, respectively) was useful in distinguishing *L. braziliensis* from the species *L. panamensis* and *L. guyanensis*.

Taqman Amplification

The Taqman primer and probe set TGCTATAAAATCGTACCACCCGACA (SEQ ID NO:101), GAACGGGGTTTCTGTATGCCATTT (SEQ ID NO:102), and TTGCAGAACGCCCCTACCCAGAGGC (SEQ ID NO:109) (*L. braziliensis* kDNA 3 forward, reverse, and probe, respectively) was capable of discriminating *L. braziliensis* from the species *L. amazonensis, L. chagasi, L. donovani, L. infantum, L. major*, and *L. tropica*, none of which amplified.

*Leptomonas*

SYBR Green Amplification

The primer set, using SYBR green chemistry, TGGAGCGGGTGCATTAACTC (SEQ ID NO:69) and GGTCTCGAGGTGCCCATGAC (SEQ ID NO:70) (*Leptomonas* Mini-exon 1 forward and reverse, respectively) was useful in distinguishing *Leptomonas* from the species *L. amazonensis, L. chagasi, L. donovani, L. infantum, L. major, L. mexicana*, and *L. braziliensis*, for which no amplification occurred. The SYBR green primer set AGAAGCCGGATGTGCTTGTG (SEQ ID NO:71) and GCCCTCAGCCTTCACCTTGT (SEQ ID NO:72) (*Leptomonas* GAPDH 2 forward and reverse, respectively) was useful in distinguishing *Leptomonas* from the species *L. amazonensis, L. chagasi, L. donovani, L. infantum, L. major*, and *L. tropica*, none of which amplified.

REFERENCE LIST FOR BACKGROUND AND EXAMPLES 1 AND 2

1. 2004. Leishmaniasis, US Armed Forces, 2003. M.S.M.R. 10:2-5.
2. Ahmed, S., M. Colmenares, L. Soong, K. Goldsmith-Pestana, L. Mustnermann, R. Molina, and D. McMahon-Pratt. 2003. Intradermal Infection Model for Pathogenesis and Vaccine Studies of Murine Visceral Leishmaniasis. Infect. Immun. 71:401-410.
3. Alvar, J., C. Canavate, B. Gutierrez-Solar, M. Jimenez, F. Laguna, R. Lopex-Velez, R. Molina, and J. Moreno. 1997. *Leishmania* and human immunodeficiency virus coinfection: the first 10 years. Clin. Microbiol. Rev. 10:298-319.
4. Aoun, O., C. Mary, C. Roqueplo, J. L. Marie, O. Terrier, A. Levieuge, and B. Davoust. 2009. Canine leishmaniasis in south-east of France: screening of *Leishmania* Miamian antibodies (western blotting, ELISA) and parasitaemia levels by PCR quantification. Vet. Parasitol. 166:27-31.
5. Barral, A., D. Pedral-Sampaio, G. Grimaldi, Jr., H. Momen, D. McMahon-Pratt, A. Ribeiro de Jesus, R. Almeida, R. Badaro, M. Barral-Netto, E. M. Carvalho, and W. D. Johnson, Jr. 1991. Leishmaniasis in Bahia, Brazil: evidence that *Leishmania amazonensis* produces a wide spectrum of clinical disease. Am. J. Trop. Med. Hyg. 44:536-546.
6. Berens, R. L., R. Brun, and S. M. Krassner. 1976. A simple monophasic medium for axenic culture of hemoflagellates. J. Parasitol. 62:360-365.
7. Berman, J. 2005. Clinical status of agents being developed for leishmaniasis. Expert Opin. Invest. Drugs 14:1337-1346.
8. Boelaert, M., S. El-Safi, A. Hailu, M. Mukhtar, S. Rijal, S. Sundar, M. Wasunna, A. Aseffa, J. Mbui, J. Menten, P. Desjeux, and R. W. Peeling. 2008. Diagnostic tests for kala-azar: a multi-centre study of the freeze-dried DAT, rK39 strip test and KAtex in East Africa and the Indian subcontinent. Trans. R. Soc. Trop. Med. Hyg. 102:32-40. doi:S0035-9203(07)00287-8 [pii]; 10.1016/j.trstmh.2007.09.003 [doi].
9. Bretagne, S., R. Durand, M. Olivi, J.-F. Garin, A. Sulahian, D. Rivollet, M. Vidaud, and M. Deniau. 2001. Real-time PCR as a new tool for quantifying *Leishmania infantum* in liver in infected mice. Clin. Diagn. Lab. Immunol. 8:828-831.
10. Bryceson, A. D. M. 1970. Immunological aspects of clinical leishmaniasis. Proc. Roy. Soc. Med. 63:40-44.
11. Cardo, L. J. 2006. *Leishmania*: risk to the blood supply. Transfusion 46:1641-1645.
12. Chappius, F., S. Sundar, A. Hailu, H. W. Ghalib, S. Rijal, R. W. Peeling, J. Alvar, and M. Boelaert. 2007. Visceral leishmaniasis: what are the needs for diagnosis, treatment and control? Nature Rev. Microbiol. 5:S7-S16.
13. Chen, J., C. A. Rauch, J. H. White, P. T. Englund, and N. R. Cozzarelli. 1995. The topology of the kinetoplast DNA network. Cell 80:61-69.
14. Costa, J. M., R. Durand, M. Deniau, D. Rivollet, M. Izri, R. Houin, M. Vidaud, and S. Bretagne. 1996. PCR enzyme-linked immunosorbent assay for diagnosis of leishmaniasis in Human Immunodeficiency Virus-infected patients. J. Clin. Microbiol. 34:1831-1833.
15. Croft, S. L., S. Sundar, and A. H. Fairlamb. 2006. Drug resistance in leishmaniasis. Clin. Microbiol. Rev. 19:111-126.
16. Davies, C. R., E. A. Lianos-Cuentas, S. J. Sharp, J. Canales, E. Leon, E. Alvarez, N. Roncal, and C. Dye. 1997. Cutaneous leishmaniasis in the peruvian andes: factors associated with variability in clinical symptoms, response to treatment, and parasite isolation rate. Clin. Infect. Dis. 25:302-310.
17. de Almeida, M. E., F. J. Steurer, O. Koru, B. L. Herwaldt, N. J. Pieniazek, and A. J. da Silva. 2011. Identification of *Leishmania* spp. by Molecular Amplification and DNA Sequencing Analysis of a Fragment of the rRNA Internal Transcribed Spacer 2 (ITS2). J. Clin. Microbiol. doi: JCM.01177-11 [pii]; 10.1128/JCM.01177-11 [doi].
18. De Bruijn, M. H. L. and D. C. Barker. 1992. Diagnosis of New World leishmaniasis: Specific detection of species of the *Leishmania braziliensis* complex by amplification of kinetoplast DNA. Acta Trop. (Basel) 52:45-58.
19. Desjeux, P. 1996. Leishmaniasis: public aspects and control. Clin. Dermatol. 14:417-423.
20. Fillola, G., J. X. Corberand, P. F. Laharrague, H. Levenes, P. Massip, and P. Recco. 1992. Peripheral intramonocytic leishmanias in an AIDS patient. J. Clin. Microbiol. 30:3284-3285.
21. Francino, O., L. Altet, E. Sanchez-Robert, A. Rodriguez, L. Solano-Gallego, J. Alberola, L. Ferrer, A. Sanchez, and X. Roura. 2006. Advantages of real-time PCR assay for diagnosis and monitoring of canine leishmaniosis. Vet. Parasitol. 137:214-221. doi:S0304-4017(06)00028-8 [pii]; 10.1016/j.vetpar.2006.01.011 [doi].
22. Gardner, P. J. 1977. Taxonomy of the genus *Leishmania*: a review of nomenclature and classification. Trop. Dis. Bull. 74:1069-1088.

23. Goeddel, D. V., D. Pennica, G. E. Nedwin, J. S. Hayflick, P. H. Seeburg, R. Derynck, M. A. Palladino, W. J. Kohr, B. B. Aggarwal, and D. V. Goeddel. 1984. Human tumour necrosis factor: precursor structure, expression and homology to lymphotoxin. Nature 312:724-729.
24. Gramiccia, M., D. F. Smith, M. C. Angelici, P. D. Ready, and L. Gradoni. 1992. A kinetoplast DNA probe diagnostic for *Leishmania infantum*. Parasitology 105:29-34.
25. Guevara, P., J. L. Ramirez, E. Rojas, J. V. Scorza, N. González, and N. Añez. 1993. *Leishmania braziliensis* in blood 30 years after cure. Lancet 341:1341.
26. Hajduk, S. L., M. E. Harris, and V. W. Pollard. 1993. RNA editing in kinetoplastid mitochondria. FASEB J. 7:54-63.
27. Hanafi, R., M. Barhoumi, S. B. Ali, and I. Guizani. 2001. Molecular analyses of Old World *Leishmania* RAPD markers and development of a PCR assay selective for parasites of the *L. donovani* species Complex. Exp. Parasitol. 98:90-99. doi:10.1006/expr.2001.4617 [doi]; S0014-4894(01)94617-X [pii].
28. Heger, A., C. A. Wilton, A. Sivakumar, and L. Holm. 2005. ADDA: a domain database with global coverage of the protein universe. Nucleic Acids Res. 33:D133-D191.
29. Henderson, D. M., S. Hanson, T. Allen, K. Wilson, D. E. Coulter-Karis, M. L. Greenberg, M. S. Hershfield, and B. Ullman. 1992. Cloning of the gene encoding *Leishmania donovani* S-adenosylhomocysteine hydrolase, a potential target for antiparasitic chemotherapy. Mol. Biochem. Parasitol. 53:169-184.
30. Herwaldt, B. L. 1999. Leishmaniasis. Lancet 354:1191-1199.
31. Ives, A., C. Ronet, F. Prevel, G. Ruzzante, S. Fuertes-Marraco, F. Schutz, H. Zangger, M. Revaz-Breton, L. F. Lye, S. M. Hickerson, S. M. Beverley, H. Acha-Orbea, P. Launois, N. Fasel, and S. Masina. 2011. *Leishmania* RNA virus controls the severity of mucocutaneous leishmaniasis. Science 331:775-778. doi:331/6018/775 [pii]; 10.1126/science.1199326 [doi].
32. Jeronimo, S. M. B., P. Duggal, R. F. S. Braz, C. Cheng, G. R. G. Monteiro, E. T. Nascimento, F. L. Bezerra, T. M. Karplus, M. F. F. M. Ximenes, C. G. C. Oliveira, V. G. Pinheiro, D. R. A. Martins, J. M. Peralta, J. M. Sousa, I. M. Medeiros, R. D. Pearson, T. L. Burns, E. W. Pugh, and M. E. Wilson. 2004. An emerging peri-urban pattern of infection with *Leishmania chagasi*, the protozoan causing visceral leishmaniasis in northeast Brazil. Scand. J. Infect. Dis. 36:443-449.
33. Laskay, T., T. Gemetchu, H. Teferedegn, and D. Frommel. 1991. The use of DNA hybridization for the detection of *Leishmania aethiopica* in naturally infected sandfly vectors. Trans. R. Soc. Trop. Med. Hyg. 85:599-602.
34. Le Fichoux, Y., J.-F. Quaranta, J.-P. Aufeuvre, A. Lelievre, P. Marty, I. Suffia, D. Rousseau, and J. Kubar. 1999. Occurrence of *Leishmania infantum* parasitemia in asymptomatic blood donors living in an area of endemicity in Southern France. J. Clin. Micro. 37:1953-1957.
35. Lee, S. T., S. C. Chiang, A. K. Singh, and H. Y. Liu. 1995. Identification of *Leishmania* species by a specific DNA probe that is conserved only in the maxicircle DNA of human-infective *Leishmania* parasites. J. Infect. Dis. 172:891-894.
36. Lopez, M., R. Inga, M. Cangalaya, J. Echevarria, A. Llanos-Cuentas, C. Orrego, and J. Arevalo. 1993. Diagnosis of *Leishmania* using the polymerase chain reaction: A simplified procedure for field work. Am. J. Trop. Med. Hyg. 49:348-356.
37. Magill, A. J., R. A. Gasser, C. N. Oster, and M. Grogl. 1992. Viscerotropic leishmaniasis in persons returning from Operation Desert Storm—1990-1991. M.M.W.R. 41:131-134.
38. Magill, A. J., M. Grogl, R. A. Gasser, S. Wellington, and C. N. Oster. 1993. Visceral infection caused by *Leishmania tropica* in veterans of Operation Desert Storm. N. Engl. J. Med. 328:1383-1387.
39. Martin-Sanchez, J., J. A. Pineda, F. Morillas-Marquez, J. A. Garcia-Garcia, C. Acedo, and J. Macias. 2004. Detection of *Leishmania infantum* kinetoplast DNA in peripheral blood from asymptomatic individuals at risk for parenterally transmitted infections: relationship between polymerase chain reaction results and other *Leishmania* infection markers. Am. J. Trop. Med. Hyg. 70:545-548.
40. Martinez, P., E. De la Vega, F. Laguna, V. Soriano, S. Puente, V. Moreno, M. J. Sentchordi, C. Garcia-Aguado, and J. González-Lahoz. 1993. Diagnosis of visceral leishmaniasis in HIV-infected individuals using peripheral blood smears. AIDS 7:227-230.
41. Mary, C., F. Faraut, L. Lascombe, and H. Dumon. 2004. Quantification of *Leishmania infantum* DNA by a real-time PCR assay with high sensitivity. J. Clin. Micro. 42:5249-5255.
42. Mary, C., F. Faraut, L. Lascombe, and H. Dumon. 2004. Quantification of *Leishmania infantum* DNA by a real-time PCR assay with high sensitivity. J. Clin. Micro. 42:5249-5255.
43. Massamba, N. N. and M. J. Mutinga. 1992. Recombinant kinetoplast DNA (kDNA) probe for identifying *Leishmania tropica*. Acta Trop. (Basel) 52:1-15.
44. Mauricio, I. L., J. R. Stothard, and M. A. Miles. 2000. The strange case of *Leishmania chagasi*. Parasitol. Today 16:188-189.
45. Maurya, R., S. Mehrotra, V. K. Prajapati, S. Nylen, D. Sacks, and S. Sundar. 2010. Evaluation of blood agar microtiter plates for culturing *Leishmania* parasites to titrate parasite burden in spleen and peripheral blood of patients with visceral leishmaniasis. J. Clin. Microbiol. 48:1932-1934. doi:JCM.01733-09 [pii]; 10.1128/JCM.01733-09 [doi].
46. McCoy, J. J., J. K. Beetham, K. S. Myung, M. E. Wilson, and J. E. Donelson. 1998. Regulatory sequences and a novel gene in the MSP (GP63) gene cluster of *Leishmania chagasi*. Mol. Biochem. Parasitol. 95:251-265.
47. Ministério da Saúde, Secretaria de Vigilância em Saúde Brazil. http://portal.saude.gov.br. 2006. Ref Type: Generic
48. Myjak, P., J. Szulta, M. E. de Almeida, A. J. da Silva, F. Steurer, A. Lass, H. Pietkiewicz, W. L. Nahorski, J. Goljan, J. Knap, and B. Szostakowska. 2009. Usefulness of PCR method for detection of *Leishmania* in Poland. Pol. J. Microbiol. 58:219-222.
49. Nicolas, L., E. Prina, T. Lang, and G. Milon. 2002. Real-time PCR for detection and quantitation of *Leishmania* in mouse tissues. J. Clin. Micro. 40:1666-1669.
50. Nuzum, E., F. I. White, T. R. Dietze, J. Wages, M. Grogi, and J. Berman. 1995. Diagnosis of symptomatic visceral leishmaniasis by use of the polymerase chain reaction on patient blood. J. Infect. Dis. 171:751-754.
51. Otero, A. C. S., V. O. da Silva, K. G. Luz, M. Palatnik, C. Pirmez, O. Fernandes, and C. B. Palatnik de Sousa. 2000. Short report: Occurrence of *Leishmania donovani* DNA in donated blood from seroreactive Brazilian blood donors. Am. J. Trop. Med. Hyg. 62:128-131.
52. Peacock, C. S., K. Seeger, D. Harris, L. Murphy, j. C. Ruiz, M. A. Quail, N. Peters, E. Adlem, A. Tivey, M.

Aslett, A. Kerhornou, A. Ivens, A. Fraser, M. A. Rajandream, T. Carver, H. Norbertczak, T. Chillingworth, Z. Hance, K. Jagels, S. Moule, D. Ormond, S. Rutter, R. Squares, S. Whitehead, E. Rabbinowitsch, C. Arrowsmith, B. White, S. Thurston, F. Bringaud, S. L. Baldauf, A. Faulconbridge, D. Jeffares, D. P. Depledge, S. O. Oyola, J. D. Hilley, L. O. Brito, Tosi, L. R., B. Barrell, A. K. Cruz, J. C. Mottram, D. F. Smith, and M. Berriman. 2007. Comparative genomic analysis of three *Leishmania* species that cause diverse human disease. Nat. Genet. 39:839-847.
53. Pearson, R. D. and A. d. Q. Sousa. 1996. Clinical Spectrum of Leishmaniasis. Clin. Infect. Dis. 22:1-13.
54. Petersen, C. A. 2009. Leishmaniasis, an Emerging Disease Found in Companion Animals in the United States. Topics in Companion Animal Medicine 24:182-188.
55. Piarroux, R., R. Azaiez, A. M. Lossi, P. Reynier, F. Muscatelli, F. Gambarelli, M. Fontes, H. Dumon, and M. Quilici. 1993. Isolation and characterization of a repetitive DNA sequence from *Leishmania infantum*: Development of a visceral leishmaniasis polymerase chain reaction. Am. J. Trop. Med. Hyg. 49:364-369.
56. Quispe-Tintaya, K. W., T. Laurent, S. Decuypere, M. Hide, A. L. Banuls, S. De Doncker, S. Rijal, C. Canavate, L. Campino, and J.-C. Dujardin. 2005. Fluorogenic assay for molecular typing of the *Leishmania donvani* complex: taxonomic and clinical applications. J. Infect. Dis. 192: 685-692.
57. Ramos, A., D. A. Maslov, O. Fernandes, D. A. Campbell, and L. Simpson. 1996. Detection and identification of human pathogenic *Leishmania* and *Trypanosoma* species by hybridization of PCR-amplified mini-exon repeats. Exp. Parasitol. 82:242-250.
58. Rozen, S. and H. Skaletsky. 2000. Primer3 on the WWW for general users and for biologist programmers. Methods Mol. Biol. 132:356-386.
59. Sanders, J. W., S. D. Pugnam, C. Frankart, R. W. Frenck, M. R. Monteville, M. S. Riddle, D. M. Rockabrand, T. W. Sharp, and D. R. Tribble. 2005. Impact of illness and non-combat injury during Operations Iraqi Freedom and Enduring Freedom (Afghanistan). Am. J. Trop. Med. Hyg. 73:713-719.
60. Schriefer, A., L. H. Guimaraes, P. R. L. Machado, M. Lessa, H. A. Lessa, E. Lago, G. Ritt, A. Goes-Neto, A. L. F. Schriefer, L. W. Riley, and E. M. Carvalho. 2009. Geographic clustering of leishmaniasis in northeastern Brazil. Emerg. Infect. Dis. 15:871-876.
61. Smyth, A. J., A. Ghosh, M. Q. Hassan, D. Basu, M. H. L. De Bruijn, S. Adhya, K. K. Mallik, and D. C. Barker. 1992. Rapid and sensitive detection of *Leishmania* kinetoplast DNA from spleen and blood samples of kala-azar patients. Parasitology 105:183-192.
62. Srivastava, P., V. K. Prajapati, M. Vanaerschot, G. Van der Auwera, J. C. Dujardin, and S. Sundar. 2010. Detection of *Leptomonas* sp. parasites in clinical isolates of Kala-azar patients from India. Infect. Genet. Evol. 10:1145-1150. doi:S1567-1348(10)00197-8 [pii]; 10.1016/j.meegid.2010.07.009 [doi].
63. van der Meide, W., J. Guerra, G. Schoone, M. Farenhorst, L. Coelho, W. Faber, I. Peekel, and H. Schallig. 2008. Comparison between quantitative nucleic acid sequence-based amplification, real-time reverse transcriptase PCR, and real-time PCR for quantification of *Leishmania* parasites. J. Clin. Micro. 46:73-78.
64. Vitale, F., S. Reale, M. Vitale, E. Petrotta, A. Torina, and S. Caracappa. 2004. TaqMan-based detection of *Leishmania infantum* DNA using canine samples. Ann. N. Y. Acad. Sci. 1026:139-143.
65. WHO Expert Committee. 1990. Control of Leishmaniasis. WHO.
66. WHO website. Leishmaniasis. http://www.who.int/leishmaniasis/en/. 2009. Ref Type: Generic
67. Wirth, D. F. and D. McMahon-Pratt. 1982. Rapid identification of *Leishmania* species by specific hybridization of kinetoplast DNA in cutaneous lesions. Proc. Natl. Acad. Sci. USA 79:6999-7003.
68. Wortmann, G., L. Hochberg, H. H. Houng, C. Sweeney, M. Zapor, N. Aronson, P. Weina, and C. F. Ockenhouse. 2005. Rapid identification of *Leishmania* complexes by a real-time PCR assay. Am. J. Trop. Med. Hyg. 73:999-1004. doi:73/6/999 [pii].
69. Zijlstra, E. E., M. S. Ali, A. M. El-Hassan, I. A. El-Toum, M. Satti, H. W. Ghalib, and P. A. Kager. 1992. Kala-azar: a comparative study of parasitological methods and the direct agglutination test in diagnosis. Trans. R. Soc. Trop. Med. Hyg. 86:505-507.

Example 3

Materials and Methods
Study Design and Population

Two subject cohorts were studied: (1) voluntary blood bank donors and (2) subjects living in a known endemic region. (1) The group of blood donors included 300 de-identified blood donations to the blood bank in Natal in the state of Rio Grande do Norte, Northeast Brazil, and 140 consenting blood bank donors who were specifically recruited and enrolled in the current study, while at the blood bank for a routine donation.

The 300 de-identified blood packs were donated in 2011 and rejected because of positive screening tests for infectious diseases [Chagas disease (n=59), Chagas disease and HIV (n=2); HIV (n=59), HCV (n=21), HBV (n=80), HTLV-1 (n=4), positive VDRL (n=42)] or because of low volume (n=30). *Leishmania infantum, Leishmania braziliensis* and *Trypanosoma cruzi* are all endemic in the draw region for blood donors for this facility. The blood bank screening test results for HCV, HIV-1, VDRL, HTVL-1 and *T. cruzi* serology were available for all samples. Samples were additionally tested for anti-*Leishmania* antibodies using an ELISA assays based on a soluble *Leishmania* lysate obtained from a local *Leishmania* isolate (IOC 563) as published.[9] In addition to these anonymous blood packs, subjects were recruited after they voluntarily presented to the blood bank for donation.

Specimens from 140 consenting blood bank donors were used to compare parasite DNA detection in whole blood versus the leukocyte fraction. (2) Blood samples from subjects living in neighborhoods with recent VL cases were also tested to estimate the rate of parasitemia in whole blood. These included 30 subjects with active VL and 30 individuals with asymptomatic *Leishmania* infection detected with a skin test. VL cases were recruited at the beginning of the treatment. They presented symptoms of VL and the laboratory findings compatible with VL, in addition to parasitological confirmation, both by culture and giemsa staining of bone marrow aspirate. People with *Leishmania* skin test positive without symptoms or signs suggestive of visceral leishmaniasis were considered with asymptomatic *L. infantum* infection, as described previously. Anti-*Leishmania* antibodies were determined by ELISA using a soluble

*Leishmania* antigens lysate (SLA) from a local *Leishmania* isolate (IOC 3071). The *Leishmania* skin test was used to assess the DTH response and was performed by using 0.1 ml of antigen at 3 cm from the cubital fold on the forearm of studied people. The antigens were kindly donated by Centro de Pesquisa e Produção de Imunobiológicos (CPPI, Curitiba, Paraná, Brazil). The skin tests were read between 48 to 72 hours after placement, by the ball point pen technique and an induration greater than 5 mm was considered positive.[12, 13]

Chagas Disease Screening

The Brazilian blood banks screened for anti-*T. cruzi* antibodies using ELISA Chagas III Test (Bios, Rio de Janeiro, RJ, Brazil). We re-tested sera that were positive by ELISA using an IFI-Chagas Kit (BioManguinhos, FIOCRUZ, Rio de Janeiro, Brazil). Samples were considered positive when uniform fluorescence was present in the membrane of the parasite at a titer of ≥80.

*Leishmania* Antibody Quantification

Antibodies were quantified by ELISA using a soluble lysate of a local strain of *Leishmania infantum* as previously reported.[9]

*Leishmania* Culture and Typing

An aliquot of buffy coat (20 μl) obtained from 10 ml from each blood pack was centrifuged at 1000×g for 15 min. The buffy coat was inoculated into both NNN blood agar and Schneider's medium.[18, 19] Capped tubes were cultured at 26° C., and samples were examined every 2 days for up to 6 weeks. The *Leishmania* species of Isolates was kindly determined by isoenzyme analysis by Elisa Cupollilo, PhD (Fiocruz, Rio de Janeiro, Brazil, a World Health Organization approved *Leishmania* reference Laboratory). *Leishmania* species were also determined by PCR for the *Leishmania* ITS1 and HSP 70 genes,[14] and by sequencing the PCR product (Macrogen Inc, Seoul, Korea).

*Leishmania* Real Time PCR

Quantitative PCR was used to measure the parasite loads. Total DNA was extracted from 10 ml of blood collected from the blood pack using an in-house protocol as previously described.[21] All reactions were conducted on a 7500 Real Time PCR system from Applied Biosystems in a 10 μl reaction mixture, using the Mag1 chromosomal, and/or kDNA7 kinetoplast DNA primers and probes described in a serial testing system.[11] TaqMan reactions were performed with ABI TaqMan universal PCR 2× master mix or ABI TaqMan Gene Expression 2× master mix with 375 nM of each forward and reverse primer, 250 nM of probe (5'FAM label, 3'TAMRA quench), and 80 ng of template DNA. The thermocycling parameters were 50° C. incubation for 2 min, 95° C. denaturation for 10 min, and 40 cycles of 95° C. (15 sec) and 60° C. (1 min). A standard curve was generated from DNA extracted from a known number of cultured *L. infantum* promastigotes ranging from $10^6$ to $10^{-1}$ promastigotes per well. A cutoff of 10 promastigotes per well was used for Mag1 and 1 promastigote per well for kDNA7, based on the linear range of the standard curve. The CTs were analyzed with SDS v1.3.1 software with the threshold for fluorescence detection set manually at 0.2 for all reactions.

Statistical Analysis

Logistic regression models were fit to predict the results of blood culture for *Leishmania* considering the results of presence of antibodies or detection of *Leishmania* DNA. All statistical analyses were performed with SPSS software (SPSS Inc., Chicago, Ill., USA) and R System 2.15.0. Results were considered statistically significant at $p<0.05$.

Ethical Considerations

Protocols for anonymous blood investigations and for consenting blood donors were reviewed and approved by the Universidade Federal do Rio Grande do Norte Ethical Committee (CEP-UFRN 081/11). The certificate of ethical approval is 0093.0.051.000-11 (http://www.saude.rn-.gov.br). This IRB committee is registered with the US National Institutes of Health. The protocol and consent form were verbally explained to all encountered subjects, after which subjects read and signed the informed consent form.

Results

Prevalence of all Infections in Donated Blood Packs in the State of Rio Grande do Norte Review of blood bank records indicated that a total of 46,624 people donated blood in the state of Rio Grande do Norte in the year 2011. Of these donors, 2.4% had a positive screen for one or more infections (Table 8). The majority of the blood donations occurred in Natal, the largest city in Rio Grande do Norte. Hepatitis B was the most commonly detected infection, followed by HIV, HCV, syphilis, Chagas disease and HTLV-1.

TABLE 8

Prevalence of infections detected through routine screening of blood donations in the state of Rio Grande do Norte during 2011, grouped by city of blood donation. Numbers indicated the total number of donations in each category, followed by the (percent of total) or [percent of infected] donations in parentheses.

| | blood donations with positive infection screenong s n (% of all blood donations) | | | | | | | |
|---|---|---|---|---|---|---|---|---|
| Total Blood Donations | HBC | HCV | HIV | VDRL | Chagas | HTLV1 | HbsAg | Total positive infection |
| 46624 (100) | 390 (0.84) | 177 (0.38) | 181 (0.39) | 170 (0.36) | 77 (0.17) | 63 (0.14) | 50 (0.11) | 1108 (2.4) |

VDRL = Venereal disease research laboratory test for syphilis;
ELISA = enzyme-linked immunosorbent assay;
HIVS PS = synthetic peptide;
HIV REC = recombinant protein;
HTLV1 = human T-lymphotropic virus type 1;
HBSAG = hepatitis B virus surface antigen;
HCV = hepatitis C virus;
HBC = IgG anti-hepatitis B A subset of blood packs that were rejected from the blood bank in Rio Grande do Norte were screened for *Leishmania* infection (n=300). Amongst the donors of these packs, 83% listed Rio Grande do Norte as their state of residence and 100% lived or had traveled in areas endemic for *L. infantum* and VL (Table 9). Males comprised the majority of infected blood donors in all groups, representing an average of 74% of rejected blood donations, but males comprised the majority of the blood donors (75%). The average age of all donors was 35.8 years. Among the 300 donated packs, 61 tested positive in the Chagas screening ELISA performed by the blood bank. All ELISA positive packs were rejected for use, and were subjected to a secondary confirmatory test (radio-immunofluorescence assay or RIFI) by blood banks in the state of Rio Grande do Norte. Of the 61 positive, 36 (59%) were negative by RIFI.

To consider the validity of *Leishmania* serology, we performed qPCR for *Leishmania* DNA using two Taqman assays that did not cross-react with *T. cruzi* One primer-probe set amplifies the nuclear Mag1 gene and the other set amplifies a region of minicircle kinetoplast DNA (kDNA7) (Table 10). Both recognize the visceralizing species *L. infantum* as described.[11]. When compared with *Leishmania* culture as the gold standard, the Mag1 test had a sensitivity

TABLE 9

Reasons for rejection of donated blood units.

| | | | | Reason for donation rejection | | | | | | |
|---|---|---|---|---|---|---|---|---|---|---|
| | Chagas ELISA | Chagas ELISA & HIV | Chagas ELISA & VDRL | HIV | HCV | HBV | HTLV | VDRL | Low volume | Total |
| Number of blood donations | 56 | 2 | 3 | 59 | 21 | 80 | 4 | 39 | 36 | 300 |
| Age (years +/- SD) | 35.8 +/- 10.3 | 40.9 +/- 15.2 | 40.3 +/- 11.8 | 34.1 +/- 9.9 | 32.5 +/- 11.0 | 36.2 +/- 10.1 | 37.2 +/- 9.2 | 36.0 +/- 8.4 | 35.7 +/- 10.2 | 35.8 +/- 10.3 |
| Male, n (%) | 40 (71) | 2 (100) | 2 (67) | 47 (80) | 14 (67) | 58 (73) | 3 (75) | 31 (79) | 26 (72) | 223 (74) |
| RN as state of residence, n (%) | 50 (89) | 1 (50) | 3 (100) | 55 (93) | 17 (81) | 61 (76) | 2 (50) | 32 (82) | 29 (81) | 250 (83) |

SD = standard deviation;
RN = Rio Grande do Norte state in northeastern Brazil;
VDRL = Venereal disease research laboratory test for syphilis;
ELISA = enzyme-linked immunosorbent assay;
HIVS PS = synthetic peptide;
HIV REC = recombinant protein;
HTLV1 = human T-lymphotropic virus type 1;
HBSAG = hepatitis B virus surface antigen;
HCV = hepatitis C virus;
HBV = IgG anti-hepatitis B.

*Leishmania* Infection

Figure 5A:
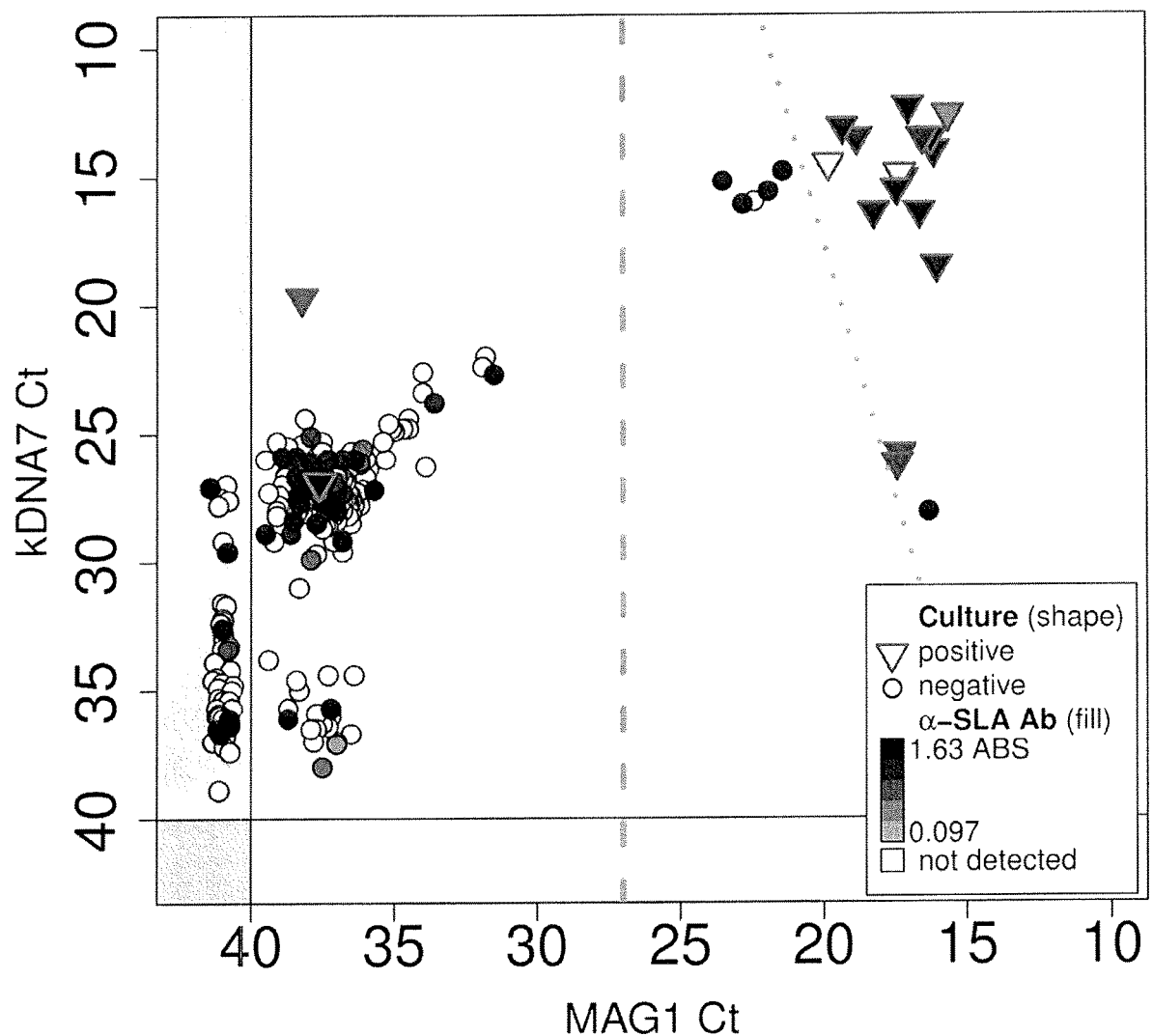
FIGS. 5A, 5B, and 5C: Results of the screening for Leishmania infection in blood samples obtained from apparent healthy donors, whose blood packs were rejected by any of the blood criteria screening. X axis presents the Ct for kDNA 7, Y axis presents the Ct for Mag1. The data was graphed with respect to Leishmania culture results (triangle=positive; sphere=negative). The shade within each symbol represents the intensity of the OD response obtained in the ELISA assay using SLA.
Figure 5B:
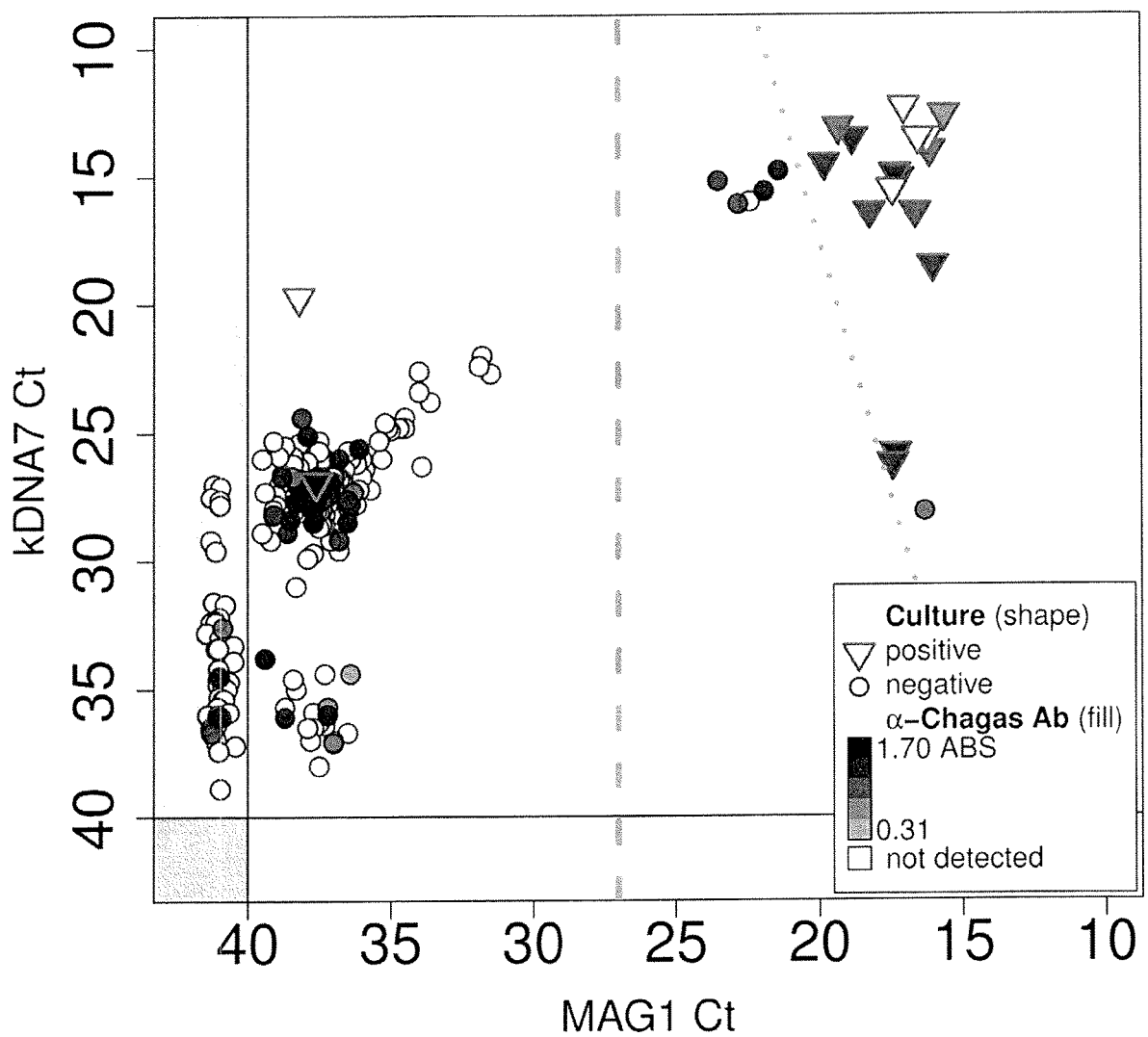
Figure 5C:
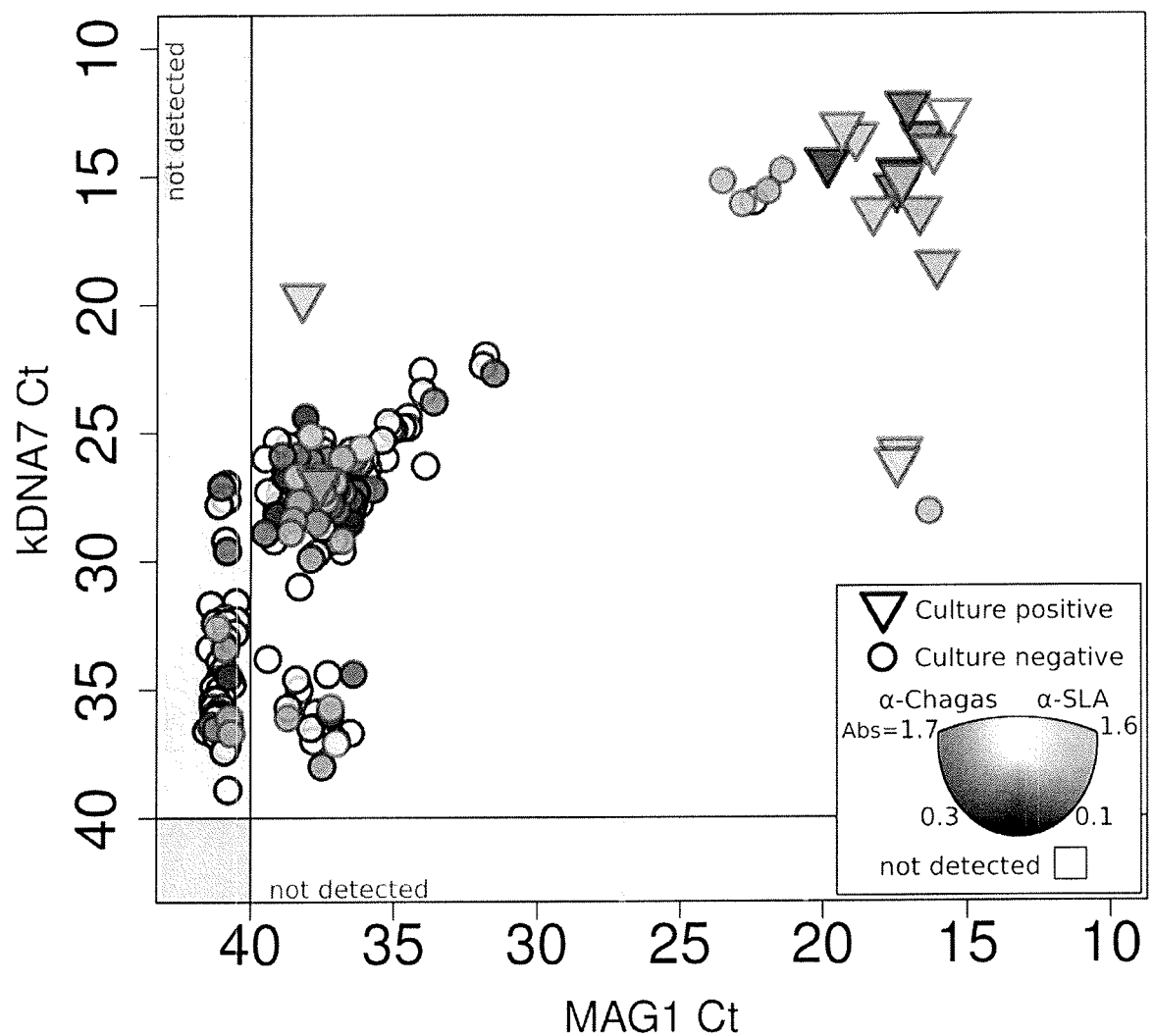

All 300 samples were screened for *Leishmania* according to three assays. 67 samples (22%) had detectable anti-*L. infantum* antibodies. Amongst these, 38/67 were also positive for Chagas ELISA and 29/67 were Chagas ELISA negative (Table 10). Eighteen of the 300 samples were *Leishmania* culture positive, of which 14/18 were Chagas ELISA positive and 16/18 were positive in the SLA ELISA for *Leishmania*. The 18 *Leishmania* isolates were typed by isoenzymes and by sequencing *Leishmania* ITS1. All positive cultures were identified as *L. infantum*. Blood samples were collected and processed in different days.

of 89% and specificity of 96%, and the kDNA7 test had a sensitivity of 100% and specificity of 21% (Table 11). Using a regression analysis, we found that the Chagas ELISA used had a significant prediction of positive *Leishmania* culture ($p<0.0001$) and classified correctly the blood sample as *Leishmania* positive in 94%, however, it had a low sensitivity (0.0%) and high specificity (100%). When the molecular markers kDNA7 and Mag1 were used, the sensitivity was (97.9%), high specificity (88.9%) and high correct classification (97.3). However, kDNA7 did not contribute significantly to the classification performance, since Mag1 alone was a better predictor (Table 11). FIGS. 5A, 5B and 5C show

TABLE 10

Tests of blood packs for Chagas disease and *leishmania* using the different diagnostic methods.

| | | Reason for blood donation rejection | | | | | | | | |
|---|---|---|---|---|---|---|---|---|---|---|
| | | Chagas ELISA (n = 56) | Chagas ELISA & HIV (n = 2) | Chagas ELISA & VDRL (n = 3) | HIV (n = 59) | HCV (n = 21) | HBV (n = 80) | HTLV (n = 4) | VDRL (n = 39) | Low volume (n = 36) | Total (n = 300) |
| Assays | ELISA-*L. infantum*, n | 36 | 1 | 1 | 7 | 4 | 8 | 1 | 1 | 8 | 67 |
| | *Leishmania* Culture | 13 | 0 | 1 | 0 | 0 | 0 | 0 | 0 | 4 | 18 |
| | Mag1 qPCR | 17 | 0 | 0 | 2 | 0 | 1 | 0 | 1 | 4 | 25 |
| | kDNA7 qPCR | 18 | 0 | 0 | 3 | 1 | 2 | 0 | 2 | 4 | 30 |
| | RIFI | 22 | 2 | 1 | 0 | 0 | 0 | 0 | 0 | 0 | 25 |

ELISA = enzyme-linked immunosorbent assay.

the results of these two primers sets and presence of *Leishmania* antibodies or results of *Leishmania* culture for all subjects tested.

TABLE 11

Logistic regression models to predict the results of blood culture for *Leishmania*.

| Ord | Predictors | p-value | Sensitivity | Specificity | % Correct prediction |
|---|---|---|---|---|---|
| 1 | Chagas ELISA(*) | <0.0001 | 77.8 | 83.3 | 83.0 |
| 2 | Mag1Ct | <0.0001 | 97.9 | 88.9 | 97.3 |
|   | kDNA7Ct | 0.161 |   |   |   |
| 3 | Mag1Ct | <0.0001 | 98.9 | 88.9 | 98.3 |
| 4 | Chagas ELISA | 0.142 | 98.2 | 88.9 | 97.7 |
|   | Mag1Ct | 0.002 |   |   |   |
|   | kDNA7Ct | 0.116 |   |   |   |
| 5 | Chagas ELISA | 0.194 | 98.6 | 88.9 | 98.0 |
|   | Mag1Ct | <0.0001 |   |   |   |
| 6 | Chagas ELISA | 0.326 | 83.3 | 98.2 | 97.3 |
|   | Leish SLA | 0.232 |   |   |   |
|   | Mag1Ct | <0.0001 |   |   |   |
| 7 | Leish SLA | 0.147 | 83.3 | 98.6 | 97.7 |
|   | Mag1Ct | <0.0001 |   |   |   |

(*)The model classify as negative. Sensitivity, specificity and classification are estimated by crossing the results.

TABLE 12

Cross tabulation assessing anti_SLA results between the blood samples tested (whole blood versus blood packs)

|  | Anti-SLA | | |
|---|---|---|---|
| Groups | Neg | Pos | Total |
| Whole blood n (%) | 99 (71.2) | 40 (28.8) | 139 (100) |
| Blood packs | 233 (77.7) | 67 (22.3) | 300 (100) |
| Total | 332 (75.6) | 107 (24.4) | 439 (100) |

Odds-Ratio (whole blood/blood pack) = 1.4 (p = 0.147)

*Leishmania* Detection in Positive and Negative Donors

Figure 6:
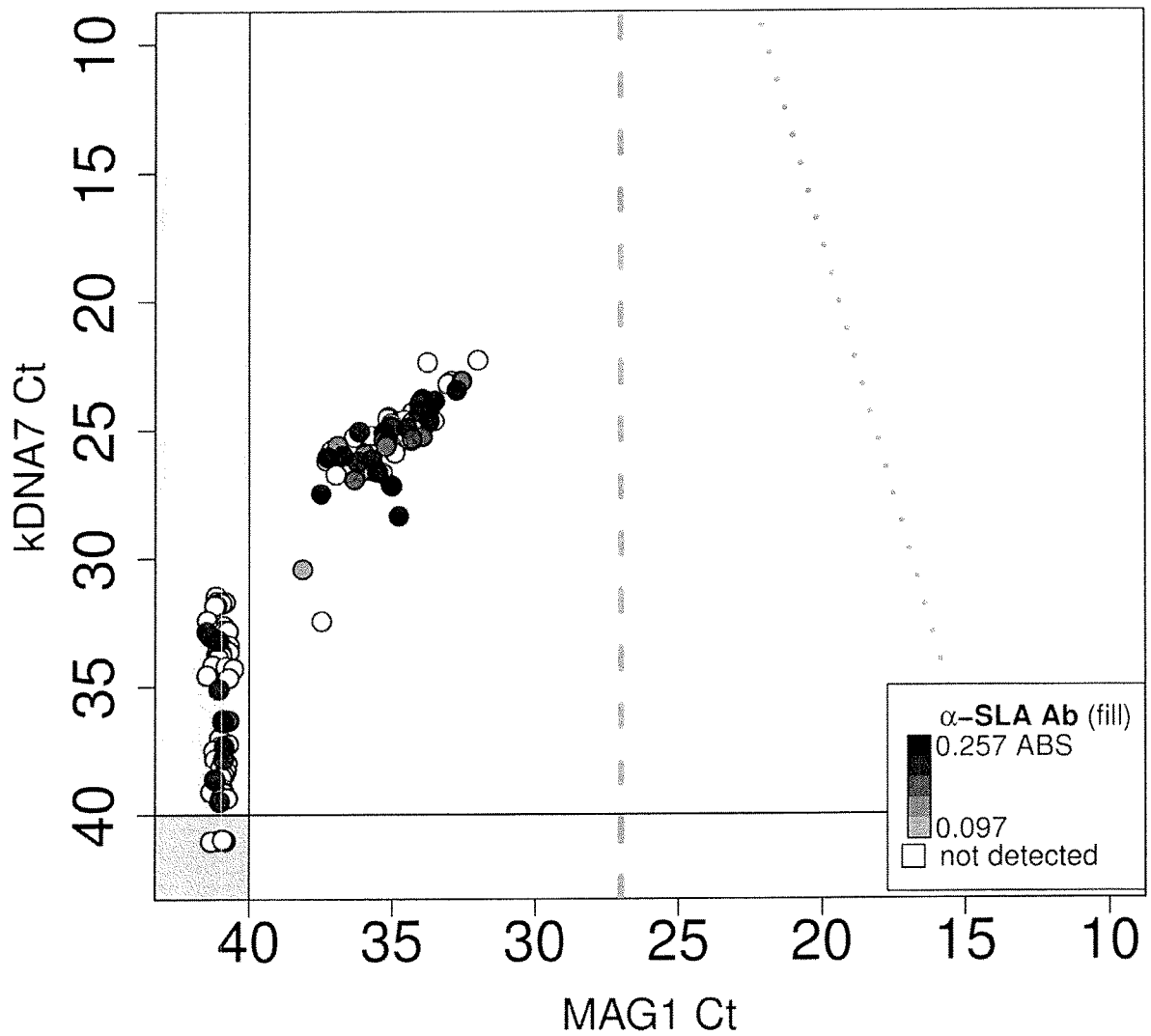
FIG. 6. Results of the screening for Leishmania infection in whole blood sample obtained from healthy blood donors. X axis presents the Ct for kDNA 7, Y axis presents the Ct for Mag1. The shade within each symbol represents the intensity of the OD response obtained in the ELISA assay using SLA.
Figure 7:
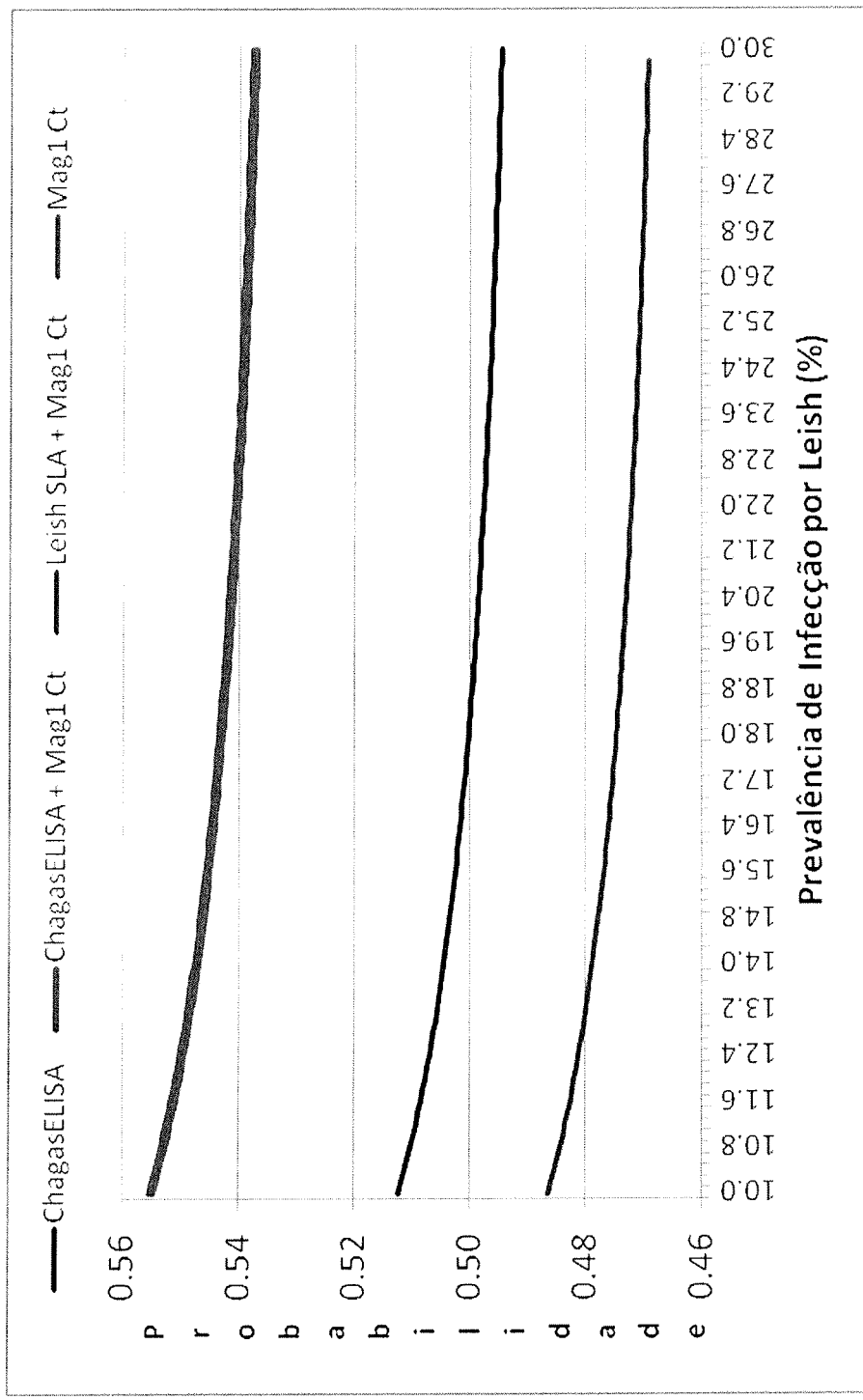
FIG. 7. Positive predictive value of Leishmania infection in accordance to the local prevalence of infection using 4 of the six logistic models.

Blood from a second group of donors (n=144) who were negative for the blood bank panel, including Chagas, were also tested (FIG. 6). The prevalence of *Leishmania* infection by SLA serology was 28.8% versus (22.3%) for the blood packs (p=0.147). However, the absorption (OD) values on the ELISA, indicating the abundance antibodies, were lower in these samples and correlated with higher Ct values observed for both kDNA and Mag1. Similarly, we tested DNA isolated from whole blood from people with symptomatic VL at the time of diagnosis, the mean Ct was 25 for kDNA and 27 for Mag1. DNA for these subjects were extracted at the time of the diagnosis. Those patients presented with severe anemia. Culture of the bone marrow aspirate was positive for *Leishmania*.

Discussion

The urbanization and the widening of visceral leishmaniasis endemic areas in Latin America and particularly in Brazil led to increased risk of exposure and infection to a larger population and therefore potential for visceral leishmaniasis development or asymptomatic *Leishmania* infection.

Brazil is endemic for Chagas disease and screening for Chagas has been in place in all Brazilian blood banks since the mid-1970s. The serologic assays used are sensitive, but can cross react with other pathogens particularly the *Leishmania* species (reviewed by Kirchhoff[14]). Chagas disease transmission has apparently decreased in Brazil in recent years due to improvements in housing although infections by the oral route from contaminated foods have been reported.[22, 23] In contrast, geographic areas in which individuals have acquired visceral leishmaniasis have widened. With movement of the population into major metropolitan there has been simultaneous migration of VL cases to urban regions,[1, 3, 5, 24, 25]. This has led to a situation in which large populations are at increased risk of exposure to *L. infantum*. In this study, 0.17% of the donors had a positive first screening for Chagas, approximately half of which were positive by confirming RIPA. The major cause of blood contamination was by hepatitis B and C infections.

*Leishmania* endemic areas have widening in South America, with a large number of people residing in metropolitan areas now at risk of infection.[1, 3, 25, 26] A characteristic of *L. infantum* infection in South America[15] and in Europe[27] is that there is a high ratio of asymptomatic to symptomatic infections. Asymptomatic people can harbor *Leishmania* and have self resolving infections, but the identification of these subjects is not easy. VL in Latin America is most likely to develop in young children and people who have some type of immunossuppression due to HIV/AIDS, neoplastic disorders and organ transplants.[28-32] This study shows that there is a high rate of parasitemia among apparently healthy people in *Leishmania* endemic areas. These people could easily be a source of infection for sand flies as well as recipients of blood transfusions or organ donations. Of the blood tested, 22.3% had positive antileishmania antibodies using a soluble *Leishmania* antigen preparation from a local *L. infantum* isolate. Of interest, 62% of the subjects who tested positive for Chagas also were positive for *Leishmania*. Of the blood samples that were Chagas positive at first Chagas ELISA screening, 22.1% grew *Leishmania* and because of the first screening for Chagas was positive, the blood was discarded. However, 4 blood samples in which blood was discarded for low volume and had no apparent infectious agent identified by blood bank screening grew *Leishmania*.

The presence of *Leishmania* in blood supplies in endemic areas of Europe and India have been reported,[11, 11, 12, 33] Because *Leishmania* can be transmitted by blood transfusion, screening for *Leishmania* should be considered in endemic areas. Of importance, since the serological assay used for detecting *T. cruzi* infection cross reacts with *Leishmania*, this type of screening probably reduces the risk of acquiring *Leishmania*, as the data presented herein showed. However, since both *L. infantum* and *T. cruzi* can overlap, it is important that a confirmatory *T. cruzi* infection assay be performed to better follow people with *T. cruzi* infections. In Brazil, subjects who are shown to have anti-*T. cruzi* antibodies are followed as outpatient and some are treated with benznidazole. In addition, the psychological burden of knowing the potential risk of developing Chagas disease might be avoided if the positive serology is due to due to asymptomatic *Leishmania* infection.

*Leishmania* culture is impractical for blood banks, but PCR assays that are highly sensitive and specific for *Leishmania* could be used to identify and exclude donations from persons in endemic regions with *Leishmania* parasitemia. Of importance, people with symptomatic VL not necessarily present high parasitemia, which brings up the fact that some people are able to successfully control high parasitemia as the data presented herein without allowing disrupture of the host metabolism nor bone marrow depression, which is normally seen in patients with symptomatic VL. The understanding of the mechanisms by which some people are able to control infection without presenting symptoms will be crucial for prevention. Finally, it is needed to understand the role of asymptomatic infection as reservoir of *Leishmania* in periurban areas.

REFERENCE LIST FOR EXAMPLE 3

1. Sherlock I A. Rev Bras Malariol Doencas Trop 1964; 16:19-26.
2. Laison R, Shaw J J, Ward R D, Fraiha H. Leishmaniasis in Brazil. IX. Considerations on the *Leishmania braziliensis* complex. Importance of sandflies of the genus *Psychodopygus* (Mangabeira) in the transmission of *L. braziliensis braziliensis* in north Brazil. Trans R Soc Trop Med Hyg 1973; 67(2):184-196.
3. Carvalho E M, Reed S G, Johnson W D, Jr. Cross reactivity between *Trypanosoma cruzi* and *Leishmania* antigens in the lymphocyte blastogenesis assay. Trans R Soc Trop Med Hyg 1987; 81(1):82-84.
4. Maia-Elkhoury A N, Alves W A, Sousa-Gomes M L, Sena J M, Luna E A. Visceral leishmaniasis in Brazil: trends and challenges. Cad Saude Publica 2008; 24(12):2941-2947.
5. Reed S G, Shreffler W G, Burns J M, Jr. et al. An improved serodiagnostic procedure for visceral leishmaniasis. Am J Trop Med Hyg 1990; 43(6):632-639.
6. Burns J M, Jr., Scott J M, Carvalho E M et al. Characterization of a membrane antigen of *Leishmania amazonensis* that stimulates human immune responses. J Immunol 1991; 146(2):742-748.
7. Braz R F, Nascimento E T, Martins D R et al. The sensitivity and specificity of *Leishmania chagasi* recombinant K39 antigen in the diagnosis of American visceral leishmaniasis and in differentiating active from subclinical infection. Am J Trop Med Hyg 2002; 67(4):344-348.
8. Harhay M O, Olliaro P L, Costa D L, Costa C H. Urban parasitology: visceral leishmaniasis in Brazil. Trends Parasitol 2011; 27(9):403-409.
9. Gouvea M V, Werneck G L, Costa C H, de Amorim Carvalho F A. Factors associated to Montenegro skin test positivity in Teresina, Brazil. Acta Trop 2007; 104(2-3): 99-107.
10. Lima I D, Queiroz J W, Lacerda H G et al. *Leishmania infantum chagasi* in Northeastern Brazil: Asymptomatic Infection at the Urban Perimeter. Am J Trop Med Hyg 2012; 86(1):99-107.
11. Weirather J L, Jeronimo S M, Gautam S et al. Serial quantitative PCR assay for detection, species discrimination, and quantification of *Leishmania* spp, in human samples. J Clin Microbiol 2011; 49(11):3892-3904.
12. Sokal J E. Editorial: Measurement of delayed skin-test responses. N Engl J Med 1975; 293(10):501-502.
13. Jose F F, da Silva I M, Araujo M I, Almeida R P, Bacellar O, Carvalho E M. [Evaluation of the sensitization power of Montenegro skin test]. Rev Soc Bras Med Trop 2001; 34(6):537-542.
14. Kuhls K, Alam M Z, Cupolillo E et al. Comparative Microsatellite Typing of New World *Leishmania infantum* Reveals Low Heterogeneity among Populations and Its Recent Old World Origin. PLoS Negl Trop Dis 2011; 5(6):e1155.
15. Salomon O D, Quintana M G, Zaidenberg M. Urban distribution of Phlebotominae in a cutaneous leishmaniasis focus, Argentina. Mem Inst Oswaldo Cruz 2008; 103(3):282-287.

What is claimed is:

1. A method for determining the presence and species of a *Leishmania* in a sample, and distinguishing the *Leishmania* species so determined from other *Leishmania* species of interest present in the sample, the method comprising:

(a) contacting the sample with the forward-and-reverse primer pairs GGGTAGGGGCGTTCTGC (SEQ ID NO:1) and TACACCAACCCCCAGTTTGC (SEQ ID NO: 2) (kDNA 1 minicircle forward and reverse primers, respectively); TGCTATAAAATCGTAC-CACCCGACA (SEQ ID NO: 101) and GAACGGGGTTTCTGTATGCCATTT (SEQ ID NO: 102) (*L.* (Y) *braziliensis* kDNA 3 forward and reverse primers, respectively); AGAGCGTGCCTTGGAT-TGTG (SEQ ID NO: 49) and CGCTGCGTTGAT-TGCGTTG (SEQ ID NO: 50) (MSP Associated Gene I (MAG I) forward and reverse primers, respectively); and GGAGAAACTCACGGCACAGG (SEQ ID NO: 67) and GCGCCTCGTAGGTCACAGTT (SEQ ID NO: 68) (SLACS forward and reverse primers, respectively); thereby forming *Leishmania*-primer pair complexes;

(b) exposing the *Leishmania*-primer pair complexes of (a) to a thermo-stable polymerase and deoxyribonucleoside triphosphates to produce (1) double-stranded DNAs containing the primer sequences and (2) pyrophosphates;

(c) performing temperature cycles to permit further production of additional double-stranded DNAs containing the primer sequences and additional pyrophosphates;

(d) determining the melting temperature of the double-stranded DNA product of (c), a characteristic melting temperature being indicative of particular *Leishmania* species so detected by the forward-and-reverse primer pairs of (a); and (e) comparing the melting temperature of (d) to a characteristic melting temperature for particular *Leishmania* species so detected by the forward-and-reverse primer pairs of (a);

thereby determining the presence and the species of the *Leishmania* in the sample, wherein the *Leishmania* species of interest comprises any of *Leishmania tropica, Leishmania chagasi/Leishmania infantum, Leishmania donovani, Leishmania major, Leishmania braziliensis, Leishmania guyanensis/Leishmania panamensis, Leishmania mexicana*, and *Leishmania amazonensis*.

2. The method of claim 1, wherein the *Leishmania* species of interest are species found in a geographic region of North, Central and South America.

3. The method of claim 1, wherein the *Leishmania* species of interest are species found in a geographic region of Europe.

4. The method of claim 3, wherein the *Leishmania* species of interest found in a geographic region of Europe are one or more of *L.* (L.) *infantum* and *L.* (L.) *donovani*.

5. The method of claim 1, wherein the *Leishmania* species of interest are species found in a geographic region of the Middle East, Northern and sub-Saharan Africa.

6. The method of claim 5, wherein the species found in a geographic region of Middle East, Northern and sub-Saharan Africa are one or more of *L.* (L.) *major, L.* (L.) *tropica*, and *L.* (L.) *infantum* and *L.* (L.) *donovani*.

7. The method of claim 5, wherein the species found in a geographic region of Middle East, Northern and sub-Saharan Africa are one or more of *L.* (L.) *infantum, L.* (L.) *donovani* and *L.* (L.) *tropica*.

8. The method of claim 1, wherein the *Leishmania* species of interest are species found in a geographic region of Asia.

9. The method of claim 8, wherein the geographic region of Asia is India, Bangladesh, Pakistan, or Nepal.

10. The method of claim 8, wherein the species found in Asia is *L.* (L.) *donovani*.

11. The method of claim 1, wherein steps (a) through (f) are repeated using at least one nucleic acid primer pair that is different for each *Leishmania* species in the group.

12. The method of claim 1, wherein the quantity of *Leishmania* in the sample is measured relative to a reference standard curve.

13. The method of claim 1, wherein determining the melting temperature comprises using ultraviolet absorption detection, fluorescence detection, light scattering detection, colorimetric detection, or chromogenic detection.

14. The method of claim 1, further comprising repeating the steps in (a) to (e), wherein step (a) comprises contacting the sample with one or more of the forward- and reverse primer pairs selected from:

AACTTTTCTGGTCCTCCGGGTAG (SEQ ID NO: 97) and ACCCCCAGTTTCCCGCC (SEQ ID NO: 98) (kDNA 2 forward and reverse primers, respectively); GGGTAGGGGCGTTCTGC (SEQ ID NO:3) and CCCGGCCTATTTTACACCAACC (SEQ ID NO:4) (kDNA 3 minicircle forward and reverse primers, respectively); GGGTGCAGAAATCCCGTTCA (SEQ ID NO:5) and CCCGGCCCTATTTTACACCA (SEQ ID NO: 6) (kDNA 4 minicircle forward and reverse primers, respectively); CTTTTCTGGTCCTCCGGGTAGG (SEQ ID NO: 99) and CCACCCGGCCCTATTTTACACCAA (SEQ ID NO: 100) (kDNA 5 minicircle forward and reverse primers, respectively); AATGGGTGCAGAAATCCCGTTC (SEQ ID NO: 7) and CCACCACCCGGCCCTATTTTAC (SEQ ID NO: 8) (kDNA 7 minicircle forward and reverse primers, respectively); GGTCCCGGCCCAAACTTTTC (SEQ ID NO: 9) and CCGGGGTTTCGCACTCATTT (SEQ ID NO: 10 (*L.* (L.) *amazonensis* kDNA 1 forward and reverse primers, respectively); GGTAGGGGCGTTCTGCAAT (SEQ ID NO: 11) and CCCGGCCTATTTTACACCAACC (SEQ ID NO: 12) (*L.* (L.) *amazonensis* kDNA 2 forward and reverse primers, respectively); GGGTAGGGGCGTTCTGC (SEQ ID NO: 13) and TACACCAACCCCCAGTTTGC (SEQ ID NO: 14) (*L.* (L.) *amazonensis* kDNA 3 forward and reverse primers, respectively); TGAGTGCAGAAACCCCGTTCATA (SEQ ID NO: 15) and ACACCAACCCCCAGTTGTGA (SEQ ID NO: 16) (*L.* (L.) *amazonensis* kDNA 4 forward and reverse primers, respectively); AATTTCGCAGAACGCCCCTAC (SEQ ID NO: 17) and GTACTCCCCGA-CATGCCTCTG (SEQ ID NO:18) (*L.* (V.) *braziliensis* kDNA 1 forward and reverse primers, respectively); TCCGCAGGAGACTTCGTATG (SEQ ID NO:103) and CACGACTATCCACCCCATCC (SEQ ID NO:104) (*L.* (L.) *infantum* Minicircle 1 forward and reverse primers, respectively); ACGGGGTTTCTGCACCCATT (SEQ ID NO: 19) and GTAGGGGCGTTCTGCAAAA (SEQ ID NO: 20) (*L.* (L.) *major* Minicircle 1 forward and reverse primers, respectively); AATGCGAGTGTTGCCCTTTTG (SEQ ID NO: 21) and GCCGAACAACGCCATATTAACC (SEQ ID NO:22) (*L.* (L.) *mexicana* Minicircle 1 forward and reverse primers, respectively); GGGGGTTGGTGTAAAATAGGG (SEQ ID NO:23) and ACCACCAGCAGAAGGTCAAAG (SEQ ID NO:24) (*L.* (L.) *tropica* Minicircle 1 forward and reverse primers, respectively); GCGGTGGCTGGTTT-TAGATG (SEQ ID NO:25) and TCCAATGAAGC-CAAGCCAGT (SEQ ID NO:26) (*L.* (L.) *donovani* Minicircle 1 forward and reverse primers, respectively); ATTTTAGTATGAGTGGTAGGTTTTGTT (SEQ ID NO: 27) and CAATAACTGGGACGGTTGCT (SEQ ID NO:28) (Cytochrome B1 forward and reverse primers, respectively); GCGGAGAGGAAAGAAAAGGCTTA (SEQ ID NO:29) and AAAAGTCATGCTAAACACACAC-CACA (SEQ ID NO: 30) (L. (L.) amazonensis Cytochrome B1 forward and reverse primers, respectively); CAGGTTGCTTACTACGTGTTTATGGTG (SEQ ID NO: 31) and TCGTATTA-CAAACCCTAAATCAAAATCTCA (SEQ ID NO:32) (L. (L.) tropica Cytochrome B1 forward and reverse primers, respectively); TCAGGTTGCTTAC-TACGTGTTTATGGTG (SEQ ID NO: 33) and TGCTAAACAAACACCACATATGATCTGC (SEQ ID NO: 34) (L. (L.) tropica Cytochrome B2 forward and reverse primers, respectively); TGACACACATAT-TTTAGTGTGGGTGGTAGG (SEQ ID NO: 35) and TCCCCAATAAGACATCATTGTACATGGTAA (SEQ ID NO: 36) (L. (L.) tropica Cytochrome B3 forward and reverse primers, respectively); CACATAT-TTTAGTGTGGGTGGTAGGTTTTG (SEQ ID NO: 37) and TCCCCAATAAGACATCATTGTA-CATGGTAA (SEQ ID NO: 38) (L. (L.) tropica Cytochrome B4 forward and reverse primers, respectively); GCTTGGTTGGATTATTTTTGCTG (SEQ ID NO: 39) and AACAACATTTTAACTCTTGTAGGAT-TCG (SEQ ID NO: 40) (Maxicircle 1 forward and reverse primers, respectively); GAGGTGTTTGCCCGCATC (SEQ ID NO:41) and CTCGCCCATGTCGTCG (SEQ ID NO: 42) (Alpha-tubulin I forward and reverse primers, respectively); TGTCGCTTGCAGACCAGATG (SEQ ID NO:105) and GCATCGCAGGTGTGAGCA (SEQ ID NO: 106) (DNA polymerase I forward and reverse primers, respectively); AGGAGGATGGCAAGCGGAAG (SEQ ID NO: 43) and GCGACGGGTACAGG-GAGTTG (SEQ ID NO:44) (DNA polymerase 2 forward and reverse primers, respectively); CGAAACTTCCGGAACCTGTCTT (SEQ ID NO: 45) and CACCACACGCACGCACAC (SEQ ID NO: 46) (Mini-exon forward and reverse primers, respectively); GTGTGGTGGCGGGTGTATGT (SEQ ID NO: 47) and GCCCAGGTCGCTGTGAGG (SEQ ID NO: 48) (Mini-exon 2 forward and reverse primers, respectively); AGTTTTGGTTGGCGCTCCTG (SEQ ID NO: 51) and CCCACTCGCTTTCCTTGGTC (SEQ ID NO:52) (MSP Associated Gene 2 (MAG 2) forward and reverse primers, respectively); CGACCCTGTCAC-CACCACAG (SEQ ID NO:53) and GAGGCCACCC-TATCGCTGAC (SEQ ID NO:54) (SIDER repeat I forward and reverse primers, respectively); TCGTT-GAGGGAGGAGGTGTTTC (SEQ ID NO:55) and TCGGCTTTGAGGTTGGCTTC (SEQ ID NO:56) (L. (V) braziliensis DNA polymerase forward and reverse primers, respectively); ACGTCGCCAACTGCTT-CACC (SEQ ID NO: 57) and GTGTTCGCACCGCCTTGAC (SEQ ID NO: 58) (L. (V) braziliensis DNA polymerase 2 forward and reverse primers, respectively); GTCGTTGTCCGTGTCGCTGT (SEQ ID NO: 59) and CGCTGTGTGTGTCCGTGTGT (SEQ ID NO:60) (L. (L.) major MSP associated gene I (L. major MAG 1) forward and reverse primers, respectively); GACGACGACGAGGAGGATGG (SEQ ID NO: 61) and GCGACGGGTACAGGGAGTTG (SEQ ID NO: 62) (L. (L.) amazonensis DNA polymerase I forward and reverse primers, respectively); CCA-GATGCCGACCAAAGC (SEQ ID NO: 107) and CGCGCACGTGATGGATAAC (SEQ ID NO: 108) (GPI forward and reverse primers, respectively); GAAGGTGCAGTCCCTCGTGT (SEQ ID NO: 63) and CCTCCGTCTGCTTGCTCTTG (SEQ ID NO: 64) (HSP70-1 forward and reverse primers, respectively); or TCGAGATCGACGCGTTGTT (SEQ ID NO: 65) and CCGCACAGCTCCTCGAA (SEQ ID NO: 66) (HSP70-4 forward and reverse primers, respectively).

15. A method for determining whether a subject is suffering from a *Leishmania* infection by detecting the presence of *Leishmania* in a sample from the subject by the method of claim 1.

* * * * *

SEQUENCE LISTING

```
<160> NUMBER OF SEQ ID NOS: 112

<210> SEQ ID NO 1
<211> LENGTH: 17
<212> TYPE: DNA
<213> ORGANISM: Artificial Sequence
<220> FEATURE:
<223> OTHER INFORMATION: kDNA 1 minicircle forward primer

<400> SEQUENCE: 1
gggtaggggc gttctgc                                                 17

<210> SEQ ID NO 2
<211> LENGTH: 20
<212> TYPE: DNA
<213> ORGANISM: Artificial Sequence
<220> FEATURE:
<223> OTHER INFORMATION: kDNA 1 minicircle reverse primer

<400> SEQUENCE: 2
tacaccaacc cccagtttgc                                              20

<210> SEQ ID NO 3
<211> LENGTH: 17
<212> TYPE: DNA
<213> ORGANISM: Artificial Sequence
<220> FEATURE:
<223> OTHER INFORMATION: kDNA 3 minicircle forward primer

<400> SEQUENCE: 3 gggtagggc gttctgc                                                  17
```

```
<210> SEQ ID NO 4
<211> LENGTH: 22
<212> TYPE: DNA
<213> ORGANISM: Artificial Sequence
<220> FEATURE:
<223> OTHER INFORMATION: kDNA 3 minicircle reverse primer

<400> SEQUENCE: 4
cccggcctat tttacaccaa cc                                              22

<210> SEQ ID NO 5
<211> LENGTH: 20
<212> TYPE: DNA
<213> ORGANISM: Artificial Sequence
<220> FEATURE:
<223> OTHER INFORMATION: kDNA 4 minicircle forward primer

<400> SEQUENCE: 5
gggtgcagaa atcccgttca                                                 20

<210> SEQ ID NO 6
<211> LENGTH: 20
<212> TYPE: DNA
<213> ORGANISM: Artificial Sequence
<220> FEATURE:
<223> OTHER INFORMATION: kDNA 4 minicircle reverse primer

<400> SEQUENCE: 6
cccggcccta ttttacacca                                                 20

<210> SEQ ID NO 7
<211> LENGTH: 22
<212> TYPE: DNA
<213> ORGANISM: Artificial Sequence
<220> FEATURE:
<223> OTHER INFORMATION: kDNA 7 minicircle forward primer

<400> SEQUENCE: 7
aatgggtgca gaaatcccgt tc                                              22

<210> SEQ ID NO 8
<211> LENGTH: 22
<212> TYPE: DNA
<213> ORGANISM: Artificial Sequence
<220> FEATURE:
<223> OTHER INFORMATION: kDNA 7 minicircle reverse primer

<400> SEQUENCE: 8
ccaccacccg gccctatttt ac                                              22

<210> SEQ ID NO 9
<211> LENGTH: 20
<212> TYPE: DNA
<213> ORGANISM: Artificial Sequence
<220> FEATURE:
<223> OTHER INFORMATION: L.(L.) amazonensis kDNA 1 forward primer

<400> SEQUENCE: 9
ggtcccggcc caaacttttc                                                 20

<210> SEQ ID NO 10
<211> LENGTH: 20
<212> TYPE: DNA
<213> ORGANISM: Artificial Sequence
<220> FEATURE:
<223> OTHER INFORMATION: L.(L.) amazonensis kDNA 1 reverse primer
```

```
<400> SEQUENCE: 10
ccggggtttc gcactcattt                                              20

<210> SEQ ID NO 11
<211> LENGTH: 20
<212> TYPE: DNA
<213> ORGANISM: Artificial Sequence
<220> FEATURE:
<223> OTHER INFORMATION: L. (L.) amazonensis kDNA 2 forward primer

<400> SEQUENCE: 11
ggtaggggcg ttctgcgaat                                              20

<210> SEQ ID NO 12
<211> LENGTH: 22
<212> TYPE: DNA
<213> ORGANISM: Artificial Sequence
<220> FEATURE:
<223> OTHER INFORMATION: L. (L.) amazonensis kDNA 2 reverse primer

<400> SEQUENCE: 12
cccggcctat tttacaccaa cc                                           22

<210> SEQ ID NO 13
<211> LENGTH: 17
<212> TYPE: DNA
<213> ORGANISM: Artificial Sequence
<220> FEATURE:
<223> OTHER INFORMATION: L. (L.) amazonensis kDNA 3 forward primer

<400> SEQUENCE: 13
gggtaggggc gttctgc                                                 17

<210> SEQ ID NO 14
<211> LENGTH: 20
<212> TYPE: DNA
<213> ORGANISM: Artificial Sequence
<220> FEATURE:
<223> OTHER INFORMATION: L. (L.) amazonensis kDNA 3 reverse primer

<400> SEQUENCE: 14
tacaccaacc cccagtttgc                                              20

<210> SEQ ID NO 15
<211> LENGTH: 23
<212> TYPE: DNA
<213> ORGANISM: Artificial Sequence
<220> FEATURE:
<223> OTHER INFORMATION: L. (L.) amazonensis kDNA 4 forward primer

<400> SEQUENCE: 15
tgagtgcaga aacccgttc ata                                           23

<210> SEQ ID NO 16
<211> LENGTH: 20
<212> TYPE: DNA
<213> ORGANISM: Artificial Sequence
<220> FEATURE:
<223> OTHER INFORMATION: L. (L.) amazonensis kDNA 4 reverse primer

<400> SEQUENCE: 16
acaccaaccc ccagttgtga                                              20

<210> SEQ ID NO 17
```

```
<211> LENGTH: 21
<212> TYPE: DNA
<213> ORGANISM: Artificial Sequence
<220> FEATURE:
<223> OTHER INFORMATION: L (V.) braziliensis kDNA 1 forward primer

<400> SEQUENCE: 17
aatttcgcag aacgccccta c                                              21

<210> SEQ ID NO 18
<211> LENGTH: 21
<212> TYPE: DNA
<213> ORGANISM: Artificial Sequence
<220> FEATURE:
<223> OTHER INFORMATION: L (V.) braziliensis kDNA 1 reverse primer

<400> SEQUENCE: 18
gtactccccg acatgcctct g                                              21

<210> SEQ ID NO 19
<211> LENGTH: 20
<212> TYPE: DNA
<213> ORGANISM: Artificial Sequence
<220> FEATURE:
<223> OTHER INFORMATION: L. (L.) major Minicircle 1 forward primer

<400> SEQUENCE: 19
acggggtttc tgcacccatt                                                20

<210> SEQ ID NO 20
<211> LENGTH: 20
<212> TYPE: DNA
<213> ORGANISM: Artificial Sequence
<220> FEATURE:
<223> OTHER INFORMATION: L. (L.) major Minicircle 1 reverse primer

<400> SEQUENCE: 20 gtagggggcgt tctgcgaaaa                                               20

<210> SEQ ID NO 21
<211> LENGTH: 21
<212> TYPE: DNA
<213> ORGANISM: Artificial Sequence
<220> FEATURE:
<223> OTHER INFORMATION: L. (L.) mexicana Minicircle 1 forward primer

<400> SEQUENCE: 21
aatgcgagtg ttgcccttttt g                                             21

<210> SEQ ID NO 22
<211> LENGTH: 22
<212> TYPE: DNA
<213> ORGANISM: Artificial Sequence
<220> FEATURE:
<223> OTHER INFORMATION: L. (L.) mexicana Minicircle 1 reverse primer

<400> SEQUENCE: 22
gccgaacaac gccatattaa cc                                             22

<210> SEQ ID NO 23
<211> LENGTH: 21
<212> TYPE: DNA
<213> ORGANISM: Artificial Sequence
<220> FEATURE:
<223> OTHER INFORMATION: L. (L.) tropica Minicircle 1 forward primer

<400> SEQUENCE: 23
```

```
gggggttggt gtaaaatagg g                                          21

<210> SEQ ID NO 24
<211> LENGTH: 21
<212> TYPE: DNA
<213> ORGANISM: Artificial Sequence
<220> FEATURE:
<223> OTHER INFORMATION: L. (L.) tropica Minicircle 1 reverse primer

<400> SEQUENCE: 24
accaccagca gaaggtcaaa g                                          21

<210> SEQ ID NO 25
<211> LENGTH: 20
<212> TYPE: DNA
<213> ORGANISM: Artificial Sequence
<220> FEATURE:
<223> OTHER INFORMATION: L. (L.) donovani Minicircle 1 forward primer

<400> SEQUENCE: 25
gcggtggctg gttttagatg                                            20

<210> SEQ ID NO 26
<211> LENGTH: 20
<212> TYPE: DNA
<213> ORGANISM: Artificial Sequence
<220> FEATURE:
<223> OTHER INFORMATION: L. (L.) donovani Minicircle 1 reverse primer

<400> SEQUENCE: 26
tccaatgaag ccaagccagt                                            20

<210> SEQ ID NO 27
<211> LENGTH: 27
<212> TYPE: DNA
<213> ORGANISM: Artificial Sequence
<220> FEATURE:
<223> OTHER INFORMATION: Cytochrome B 1 forward primer

<400> SEQUENCE: 27
attttagtat gagtggtagg ttttgtt                                    27

<210> SEQ ID NO 28
<211> LENGTH: 20
<212> TYPE: DNA
<213> ORGANISM: Artificial Sequence
<220> FEATURE:
<223> OTHER INFORMATION: Cytochrome B 1 reverse primer

<400> SEQUENCE: 28
caataactgg gacggttgct                                            20

<210> SEQ ID NO 29
<211> LENGTH: 23
<212> TYPE: DNA
<213> ORGANISM: Artificial Sequence
<220> FEATURE:
<223> OTHER INFORMATION: L. (L.) amazonensis Cytochrome B1 forward
      primer

<400> SEQUENCE: 29
gcggagagga aagaaaaggc tta                                        23

<210> SEQ ID NO 30
<211> LENGTH: 26
```

```
<212> TYPE: DNA
<213> ORGANISM: Artificial Sequence
<220> FEATURE:
<223> OTHER INFORMATION: L. (L.) amazonensis Cytochrome B1 reverse
      primer

<400> SEQUENCE: 30
aaaagtcatg ctaaacacac accaca                                          26

<210> SEQ ID NO 31
<211> LENGTH: 27
<212> TYPE: DNA
<213> ORGANISM: Artificial Sequence
<220> FEATURE:
<223> OTHER INFORMATION: L. (L.) tropica Cytochrome B 1 forward primer

<400> SEQUENCE: 31
caggttgctt actacgtgtt tatggtg                                         27

<210> SEQ ID NO 32
<211> LENGTH: 30
<212> TYPE: DNA
<213> ORGANISM: Artificial Sequence
<220> FEATURE:
<223> OTHER INFORMATION: L. (L.) tropica Cytochrome B 1 reverse primer

<400> SEQUENCE: 32
tcgtattaca aaccctaaat caaaatctca                                      30

<210> SEQ ID NO 33
<211> LENGTH: 28
<212> TYPE: DNA
<213> ORGANISM: Artificial Sequence
<220> FEATURE:
<223> OTHER INFORMATION: L. (L.) tropica Cytochrome B 2 forward primer

<400> SEQUENCE: 33
tcaggttgct tactacgtgt ttatggtg                                        28

<210> SEQ ID NO 34
<211> LENGTH: 28
<212> TYPE: DNA
<213> ORGANISM: Artificial Sequence
<220> FEATURE:
<223> OTHER INFORMATION: L. (L.) tropica Cytochrome B 2 reverse primer

<400> SEQUENCE: 34
tgctaaacaa acaccacata tgatctgc                                        28

<210> SEQ ID NO 35
<211> LENGTH: 30
<212> TYPE: DNA
<213> ORGANISM: Artificial Sequence
<220> FEATURE:
<223> OTHER INFORMATION: L. (L.) tropica Cytochrome B 3 forward primer

<400> SEQUENCE: 35
tgacacacat attttagtgt gggtggtagg                                      30

<210> SEQ ID NO 36
<211> LENGTH: 30
<212> TYPE: DNA
<213> ORGANISM: Artificial Sequence
<220> FEATURE:
<223> OTHER INFORMATION: L. (L.) tropica Cytochrome B 3 reverse primer

<400> SEQUENCE: 36
```
tccccaataa gacatcattg tacatggtaa                                    30

<210> SEQ ID NO 37
<211> LENGTH: 30
<212> TYPE: DNA
<213> ORGANISM: Artificial Sequence
<220> FEATURE:
<223> OTHER INFORMATION: L. (L.) tropica Cytochrome B 4 forward primer

<400> SEQUENCE: 37
cacatatttt agtgtgggtg gtaggttttg                                    30

<210> SEQ ID NO 38
<211> LENGTH: 30
<212> TYPE: DNA
<213> ORGANISM: Artificial Sequence
<220> FEATURE:
<223> OTHER INFORMATION: L. (L.) tropica Cytochrome B 4 reverse primer

<400> SEQUENCE: 38
tccccaataa gacatcattg tacatggtaa                                    30

<210> SEQ ID NO 39
<211> LENGTH: 23
<212> TYPE: DNA
<213> ORGANISM: Artificial Sequence
<220> FEATURE:
<223> OTHER INFORMATION: Maxicircle 1 forward primer

<400> SEQUENCE: 39
gcttggttgg attattttg ctg                                            23

<210> SEQ ID NO 40
<211> LENGTH: 28
<212> TYPE: DNA
<213> ORGANISM: Artificial Sequence
<220> FEATURE:
<223> OTHER INFORMATION: Maxicircle 1 reverse primer

<400> SEQUENCE: 40
aacaacattt taactcttgt aggattcg                                      28

<210> SEQ ID NO 41
<211> LENGTH: 18
<212> TYPE: DNA
<213> ORGANISM: Artificial Sequence
<220> FEATURE:
<223> OTHER INFORMATION: Alpha-tubulin 1 forward primer

<400> SEQUENCE: 41
gaggtgtttg cccgcatc                                                 18

<210> SEQ ID NO 42
<211> LENGTH: 16
<212> TYPE: DNA
<213> ORGANISM: Artificial Sequence
<220> FEATURE:
<223> OTHER INFORMATION: Alpha-tubulin 1 reverse primer

<400> SEQUENCE: 42
ctcgcccatg tcgtcg                                                   16

<210> SEQ ID NO 43
<211> LENGTH: 20
<212> TYPE: DNA

```
<213> ORGANISM: Artificial Sequence
<220> FEATURE:
<223> OTHER INFORMATION: DNA polymerase 2 forward primer

<400> SEQUENCE: 43
aggaggatgg caagcggaag                                                    20

<210> SEQ ID NO 44
<211> LENGTH: 20
<212> TYPE: DNA
<213> ORGANISM: Artificial Sequence
<220> FEATURE:
<223> OTHER INFORMATION: DNA polymerase 2 reverse primer

<400> SEQUENCE: 44
gcgacgggta cagggagttg                                                    20

<210> SEQ ID NO 45
<211> LENGTH: 22
<212> TYPE: DNA
<213> ORGANISM: Artificial Sequence
<220> FEATURE:
<223> OTHER INFORMATION: Mini-exon 1 forward primer

<400> SEQUENCE: 45
cgaaacttcc ggaacctgtc tt                                                 22

<210> SEQ ID NO 46
<211> LENGTH: 18
<212> TYPE: DNA
<213> ORGANISM: Artificial Sequence
<220> FEATURE:
<223> OTHER INFORMATION: Mini-exon 1 reverse primer

<400> SEQUENCE: 46
caccacacgc acgcacac                                                      18

<210> SEQ ID NO 47
<211> LENGTH: 20
<212> TYPE: DNA
<213> ORGANISM: Artificial Sequence
<220> FEATURE:
<223> OTHER INFORMATION: Mini-exon 2 forward primer

<400> SEQUENCE: 47
gtgtggtggc gggtgtatgt                                                    20

<210> SEQ ID NO 48
<211> LENGTH: 18
<212> TYPE: DNA
<213> ORGANISM: Artificial Sequence
<220> FEATURE:
<223> OTHER INFORMATION: Mini-exon 2 reverse primer

<400> SEQUENCE: 48
gcccaggtcg ctgtgagg                                                      18

<210> SEQ ID NO 49
<211> LENGTH: 20
<212> TYPE: DNA
<213> ORGANISM: Artificial Sequence
<220> FEATURE:
<223> OTHER INFORMATION: MSP Associated Gene 1 (MAG 1) forward primer

<400> SEQUENCE: 49
agagcgtgcc ttggattgtg                                                    20
```

```
<210> SEQ ID NO 50
<211> LENGTH: 19
<212> TYPE: DNA
<213> ORGANISM: Artificial Sequence
<220> FEATURE:
<223> OTHER INFORMATION: MSP Associated Gene 1 (MAG 1) reverse primer

<400> SEQUENCE: 50
cgctgcgttg attgcgttg                                                19

<210> SEQ ID NO 51
<211> LENGTH: 20
<212> TYPE: DNA
<213> ORGANISM: Artificial Sequence
<220> FEATURE:
<223> OTHER INFORMATION: MSP Associated Gene 2 (MAG 2) forward primer

<400> SEQUENCE: 51
agttttggtt ggcgctcctg                                               20

<210> SEQ ID NO 52
<211> LENGTH: 20
<212> TYPE: DNA
<213> ORGANISM: Artificial Sequence
<220> FEATURE:
<223> OTHER INFORMATION: MSP Associated Gene 2 (MAG 2) reverse primer

<400> SEQUENCE: 52
cccactcgct ttccttggtc                                               20

<210> SEQ ID NO 53
<211> LENGTH: 20
<212> TYPE: DNA
<213> ORGANISM: Artificial Sequence
<220> FEATURE:
<223> OTHER INFORMATION: SIDER repeat 1 forward primer

<400> SEQUENCE: 53
cgaccctgtc accaccacag                                               20

<210> SEQ ID NO 54
<211> LENGTH: 20
<212> TYPE: DNA
<213> ORGANISM: Artificial Sequence
<220> FEATURE:
<223> OTHER INFORMATION: SIDER repeat 1 reverse primer

<400> SEQUENCE: 54
gaggccaccc tatcgctgac                                               20

<210> SEQ ID NO 55
<211> LENGTH: 22
<212> TYPE: DNA
<213> ORGANISM: Artificial Sequence
<220> FEATURE:
<223> OTHER INFORMATION: L. (V.) braziliensis DNA polymerase 1 forward
      primer

<400> SEQUENCE: 55
tcgttgaggg aggaggtgtt tc                                            22

<210> SEQ ID NO 56
<211> LENGTH: 20
<212> TYPE: DNA
<213> ORGANISM: Artificial Sequence
```

```
<220> FEATURE:
<223> OTHER INFORMATION: L. (V.) braziliensis DNA polymerase 1 reverse
      primer

<400> SEQUENCE: 56
tcggctttga ggttggcttc                                                  20

<210> SEQ ID NO 57
<211> LENGTH: 20
<212> TYPE: DNA
<213> ORGANISM: Artificial Sequence
<220> FEATURE:
<223> OTHER INFORMATION: L. (V.) braziliensis DNA polymerase 2 forward
      primer

<400> SEQUENCE: 57
acgtcgccaa ctgcttcacc                                                  20

<210> SEQ ID NO 58
<211> LENGTH: 19
<212> TYPE: DNA
<213> ORGANISM: Artificial Sequence
<220> FEATURE:
<223> OTHER INFORMATION: L. (V.) braziliensis DNA polymerase 2 reverse
      primer

<400> SEQUENCE: 58
gtgttcgcac cgccttgac                                                   19

<210> SEQ ID NO 59
<211> LENGTH: 20
<212> TYPE: DNA
<213> ORGANISM: Artificial Sequence
<220> FEATURE:
<223> OTHER INFORMATION: L.(L.) major MSP associated gene 1 (L. major
      MAG 1) forward primer

<400> SEQUENCE: 59
gtcgttgtcc gtgtcgctgt                                                  20

<210> SEQ ID NO 60
<211> LENGTH: 20
<212> TYPE: DNA
<213> ORGANISM: Artificial Sequence
<220> FEATURE:
<223> OTHER INFORMATION: L.(L.) major MSP associated gene 1 (L. major
      MAG 1) reverse primer

<400> SEQUENCE: 60
cgctgtgtgt gtccgtgtgt                                                  20

<210> SEQ ID NO 61
<211> LENGTH: 20
<212> TYPE: DNA
<213> ORGANISM: Artificial Sequence
<220> FEATURE:
<223> OTHER INFORMATION: L (L.) amazonensis DNA polymerase 1 forward
      primer

<400> SEQUENCE: 61
gacgacgacg aggaggatgg                                                  20

<210> SEQ ID NO 62
<211> LENGTH: 20
<212> TYPE: DNA
<213> ORGANISM: Artificial Sequence
<220> FEATURE:
```

<223> OTHER INFORMATION: L (L.) amazonensis DNA polymerase 1 reverse
      primer

<400> SEQUENCE: 62
gcgacgggta cagggagttg                                                  20

<210> SEQ ID NO 63
<211> LENGTH: 20
<212> TYPE: DNA
<213> ORGANISM: Artificial Sequence
<220> FEATURE:
<223> OTHER INFORMATION: HSP70-1 forward primer

<400> SEQUENCE: 63
gaaggtgcag tccctcgtgt                                                  20

<210> SEQ ID NO 64
<211> LENGTH: 20
<212> TYPE: DNA
<213> ORGANISM: Artificial Sequence
<220> FEATURE:
<223> OTHER INFORMATION: HSP70-1 reverse primer

<400> SEQUENCE: 64
cctccgtctg cttgctcttg                                                  20

<210> SEQ ID NO 65
<211> LENGTH: 19
<212> TYPE: DNA
<213> ORGANISM: Artificial Sequence
<220> FEATURE:
<223> OTHER INFORMATION: HSP70-4 forward primer

<400> SEQUENCE: 65
tcgagatcga cgcgttgtt                                                   19

<210> SEQ ID NO 66
<211> LENGTH: 17
<212> TYPE: DNA
<213> ORGANISM: Artificial Sequence
<220> FEATURE:
<223> OTHER INFORMATION: HSP70-4 reverse primer

<400> SEQUENCE: 66
ccgcacagct cctcgaa                                                     17

<210> SEQ ID NO 67
<211> LENGTH: 20
<212> TYPE: DNA
<213> ORGANISM: Artificial Sequence
<220> FEATURE:
<223> OTHER INFORMATION: SLACS forward primer

<400> SEQUENCE: 67
ggagaaactc acggcacagg                                                  20

<210> SEQ ID NO 68
<211> LENGTH: 20
<212> TYPE: DNA
<213> ORGANISM: Artificial Sequence
<220> FEATURE:
<223> OTHER INFORMATION: SLACS reverse primer

<400> SEQUENCE: 68
gcgcctcgta ggtcacagtt                                                  20

<210> SEQ ID NO 69
<211> LENGTH: 20
<212> TYPE: DNA
<213> ORGANISM: Artificial Sequence
<220> FEATURE:
<223> OTHER INFORMATION: Leptomonas Mini-exon 1 forward primer

<400> SEQUENCE: 69
tggagcgggt gcattaactc                                               20

<210> SEQ ID NO 70
<211> LENGTH: 20
<212> TYPE: DNA
<213> ORGANISM: Artificial Sequence
<220> FEATURE:
<223> OTHER INFORMATION: Leptomonas Mini-exon 1 reverse primer

<400> SEQUENCE: 70
ggtctcgagg tgcccatgac                                               20

<210> SEQ ID NO 71
<211> LENGTH: 20
<212> TYPE: DNA
<213> ORGANISM: Artificial Sequence
<220> FEATURE:
<223> OTHER INFORMATION: Leptomonas GAPDH 2 forward primer

<400> SEQUENCE: 71
agaagccgga tgtgcttgtg                                               20

<210> SEQ ID NO 72
<211> LENGTH: 20
<212> TYPE: DNA
<213> ORGANISM: Artificial Sequence
<220> FEATURE:
<223> OTHER INFORMATION: Leptomonas GAPDH 2 reverse primer

<400> SEQUENCE: 72
gccctcagcc ttcaccttgt                                               20

<210> SEQ ID NO 73
<211> LENGTH: 20
<212> TYPE: DNA
<213> ORGANISM: Artificial Sequence
<220> FEATURE:
<223> OTHER INFORMATION: Human TNF alpha 1 forward primer

<400> SEQUENCE: 73
gccctgtgag gaggacgaac                                               20

<210> SEQ ID NO 74
<211> LENGTH: 24
<212> TYPE: DNA
<213> ORGANISM: Artificial Sequence
<220> FEATURE:
<223> OTHER INFORMATION: Human TNF alpha 1 reverse primer

<400> SEQUENCE: 74
aagaggttga gggtgtctga agga                                          24

<210> SEQ ID NO 75
<211> LENGTH: 20
<212> TYPE: DNA
<213> ORGANISM: Artificial Sequence
<220> FEATURE:
<223> OTHER INFORMATION: Human TNF alpha 2 forward primer

<400> SEQUENCE: 75
gcgctcccca agaagacagg                                                20

<210> SEQ ID NO 76
<211> LENGTH: 22
<212> TYPE: DNA
<213> ORGANISM: Artificial Sequence
<220> FEATURE:
<223> OTHER INFORMATION: Human TNF alpha 2 reverse primer

<400> SEQUENCE: 76
tgccacgatc aggaaggaga ag                                             22

<210> SEQ ID NO 77
<211> LENGTH: 21
<212> TYPE: DNA
<213> ORGANISM: Artificial Sequence
<220> FEATURE:
<223> OTHER INFORMATION: Human GAPDH 1 forward primer

<400> SEQUENCE: 77
gggctctcca gaacatcatc c                                              21

<210> SEQ ID NO 78
<211> LENGTH: 20
<212> TYPE: DNA
<213> ORGANISM: Artificial Sequence
<220> FEATURE:
<223> OTHER INFORMATION: Human GAPDH 1 reverse primer

<400> SEQUENCE: 78
ccagtgagct tcccgttcag                                                20

<210> SEQ ID NO 79
<211> LENGTH: 22
<212> TYPE: DNA
<213> ORGANISM: Artificial Sequence
<220> FEATURE:
<223> OTHER INFORMATION: Human GAPDH 2 forward primer

<400> SEQUENCE: 79
catcaagaag gtggtgaagc ag                                             22

<210> SEQ ID NO 80
<211> LENGTH: 20
<212> TYPE: DNA
<213> ORGANISM: Artificial Sequence
<220> FEATURE:
<223> OTHER INFORMATION: Human GAPDH 2 reverse primer

<400> SEQUENCE: 80
cgtcaaaggt ggaggagtgg                                                20

<210> SEQ ID NO 81
<211> LENGTH: 18
<212> TYPE: DNA
<213> ORGANISM: Artificial Sequence
<220> FEATURE:
<223> OTHER INFORMATION: Human GAPDH 3 forward primer

<400> SEQUENCE: 81
gcatggcctt ccgtgtcc                                                  18

<210> SEQ ID NO 82

```
<211> LENGTH: 20
<212> TYPE: DNA
<213> ORGANISM: Artificial Sequence
<220> FEATURE:
<223> OTHER INFORMATION: Human GAPDH 3 reverse primer

<400> SEQUENCE: 82
cgcctgcttc accaccttct                                                20

<210> SEQ ID NO 83
<211> LENGTH: 20
<212> TYPE: DNA
<213> ORGANISM: Artificial Sequence
<220> FEATURE:
<223> OTHER INFORMATION: third nucleic acid probe; kDNA 4 minicircle
      Taqman probe

<400> SEQUENCE: 83 accccccagtt tcccgccccg                                               20

<210> SEQ ID NO 84
<211> LENGTH: 20
<212> TYPE: DNA
<213> ORGANISM: Artificial Sequence
<220> FEATURE:
<223> OTHER INFORMATION: third nucleic acid probe; kDNA 7 minicircle
      Taqman probe

<400> SEQUENCE: 84
ccccagtttc ccgccccgga                                                20

<210> SEQ ID NO 85
<211> LENGTH: 23
<212> TYPE: DNA
<213> ORGANISM: Artificial Sequence
<220> FEATURE:
<223> OTHER INFORMATION: third nucleic acid probe; L. (L.) amazonensis
      kDNA 2 Taqman probe

<400> SEQUENCE: 85
tggccttggg gcgtgcaaac tgg                                            23

<210> SEQ ID NO 86
<211> LENGTH: 20
<212> TYPE: DNA
<213> ORGANISM: Artificial Sequence
<220> FEATURE:
<223> OTHER INFORMATION: third nucleic acid probe; L. (L.) tropica
      Minicircle 1 Taqman probe

<400> SEQUENCE: 86
tcctggcggg ggttttcgct                                                20

<210> SEQ ID NO 87
<211> LENGTH: 23
<212> TYPE: DNA
<213> ORGANISM: Artificial Sequence
<220> FEATURE:
<223> OTHER INFORMATION: third nucleic acid probe; L. (L.) donovani
      Minicircle 1 Taqman probe

<400> SEQUENCE: 87
cccataccac caaacgcagc cca                                            23

<210> SEQ ID NO 88
<211> LENGTH: 33
<212> TYPE: DNA
```

```
<213> ORGANISM: Artificial Sequence
<220> FEATURE:
<223> OTHER INFORMATION: third nucleic acid probe; Cytochrome B 1 Taqman
      probe

<400> SEQUENCE: 88
ccatgtacga tgatgtcgta ttgaggtcta aca                                    33

<210> SEQ ID NO 89
<211> LENGTH: 35
<212> TYPE: DNA
<213> ORGANISM: Artificial Sequence
<220> FEATURE:
<223> OTHER INFORMATION: third nucleic acid probe; Maxicircle 1 Taqman
      probe

<400> SEQUENCE: 89
ctttaggtag ggagttgtac tacgtttttt gacct                                  35

<210> SEQ ID NO 90
<211> LENGTH: 20
<212> TYPE: DNA
<213> ORGANISM: Artificial Sequence
<220> FEATURE:
<223> OTHER INFORMATION: third nucleic acid probe; Alpha-tubulin 1
      Taqman probe

<400> SEQUENCE: 90
tgagggcatg gaggagggcg                                                   20

<210> SEQ ID NO 91
<211> LENGTH: 22
<212> TYPE: DNA
<213> ORGANISM: Artificial Sequence
<220> FEATURE:
<223> OTHER INFORMATION: third nucleic acid probe; DNA polymerase 2
      Taqman probe

<400> SEQUENCE: 91
tggggtcgag caccatgccg cc                                                22

<210> SEQ ID NO 92
<211> LENGTH: 23
<212> TYPE: DNA
<213> ORGANISM: Artificial Sequence
<220> FEATURE:
<223> OTHER INFORMATION: third nucleic acid probe; Mini-exon 1 Taqman
      probe

<400> SEQUENCE: 92
cggcaagatt ttggaagcgc gca                                               23

<210> SEQ ID NO 93
<211> LENGTH: 22
<212> TYPE: DNA
<213> ORGANISM: Artificial Sequence
<220> FEATURE:
<223> OTHER INFORMATION: third nucleic acid probe; MSP Associated Gene 1
      (MAG 1) Taqman probe

<400> SEQUENCE: 93
tgcgcactgc actgtcgccc cc                                                22

<210> SEQ ID NO 94
<211> LENGTH: 23
<212> TYPE: DNA
<213> ORGANISM: Artificial Sequence
```

```
<220> FEATURE:
<223> OTHER INFORMATION: third nucleic acid probe; MSP Associated Gene 2
      (MAG 2) Taqman probe

<400> SEQUENCE: 94
cgctgagagc gaggcaggca cgc                                                23

<210> SEQ ID NO 95
<211> LENGTH: 25
<212> TYPE: DNA
<213> ORGANISM: Artificial Sequence
<220> FEATURE:
<223> OTHER INFORMATION: third nucleic acid probe; Human TNF alpha 1
      Taqman probe

<400> SEQUENCE: 95
ccttcccaaa cgcctcccct gcccc                                              25

<210> SEQ ID NO 96
<211> LENGTH: 21
<212> TYPE: DNA
<213> ORGANISM: Artificial Sequence
<220> FEATURE:
<223> OTHER INFORMATION: third nucleic acid probe; Human TNF alpha 2
      Taqman probe

<400> SEQUENCE: 96
caccgcctgg agccctgggg c                                                  21

<210> SEQ ID NO 97
<211> LENGTH: 23
<212> TYPE: DNA
<213> ORGANISM: Artificial Sequence
<220> FEATURE:
<223> OTHER INFORMATION: kDNA 2 forward primer

<400> SEQUENCE: 97
aacttttctg gtcctccggg tag                                                23

<210> SEQ ID NO 98
<211> LENGTH: 17
<212> TYPE: DNA
<213> ORGANISM: Artificial Sequence
<220> FEATURE:
<223> OTHER INFORMATION: kDNA 2 reverse primer

<400> SEQUENCE: 98
acccccagtt tcccgcc                                                       17

<210> SEQ ID NO 99
<211> LENGTH: 22
<212> TYPE: DNA
<213> ORGANISM: Artificial Sequence
<220> FEATURE:
<223> OTHER INFORMATION: kDNA 5 minicircle forward primer

<400> SEQUENCE: 99
cttttctggt cctccgggta gg                                                 22

<210> SEQ ID NO 100
<211> LENGTH: 24
<212> TYPE: DNA
<213> ORGANISM: Artificial Sequence
<220> FEATURE:
<223> OTHER INFORMATION: kDNA 5 minicircle reverse primer

<400> SEQUENCE: 100
```

-continued

```
ccacccggcc ctattttaca ccaa                                          24

<210> SEQ ID NO 101
<211> LENGTH: 25
<212> TYPE: DNA
<213> ORGANISM: Artificial Sequence
<220> FEATURE:
<223> OTHER INFORMATION: L (V.) braziliensis kDNA 3 forward primer

<400> SEQUENCE: 101
tgctataaaa tcgtaccacc cgaca                                         25

<210> SEQ ID NO 102
<211> LENGTH: 24
<212> TYPE: DNA
<213> ORGANISM: Artificial Sequence
<220> FEATURE:
<223> OTHER INFORMATION: L (V.) braziliensis kDNA 3 reverse primer

<400> SEQUENCE: 102
gaacggggtt tctgtatgcc attt                                          24

<210> SEQ ID NO 103
<211> LENGTH: 20
<212> TYPE: DNA
<213> ORGANISM: Artificial Sequence
<220> FEATURE:
<223> OTHER INFORMATION: L (L.) infantum Minicircle 1 forward primer

<400> SEQUENCE: 103
tccgcaggag acttcgtatg                                               20

<210> SEQ ID NO 104
<211> LENGTH: 20
<212> TYPE: DNA
<213> ORGANISM: Artificial Sequence
<220> FEATURE:
<223> OTHER INFORMATION: L (L.) infantum Minicircle 1 reverse primer

<400> SEQUENCE: 104
cacgactatc caccccatcc                                               20

<210> SEQ ID NO 105
<211> LENGTH: 20
<212> TYPE: DNA
<213> ORGANISM: Artificial Sequence
<220> FEATURE:
<223> OTHER INFORMATION: DNA polymerase 1 forward primer

<400> SEQUENCE: 105
tgtcgcttgc agaccagatg                                               20

<210> SEQ ID NO 106
<211> LENGTH: 18
<212> TYPE: DNA
<213> ORGANISM: Artificial Sequence
<220> FEATURE:
<223> OTHER INFORMATION: DNA polymerase 1 reverse primer

<400> SEQUENCE: 106
gcatcgcagg tgtgagca                                                 18

<210> SEQ ID NO 107
<211> LENGTH: 18
<212> TYPE: DNA
```

```
<213> ORGANISM: Artificial Sequence
<220> FEATURE:
<223> OTHER INFORMATION: GPI forward primer

<400> SEQUENCE: 107
ccagatgccg accaaagc                                                  18

<210> SEQ ID NO 108
<211> LENGTH: 19
<212> TYPE: DNA
<213> ORGANISM: Artificial Sequence
<220> FEATURE:
<223> OTHER INFORMATION: GPI reverse primer

<400> SEQUENCE: 108
cgcgcacgtg atggataac                                                 19

<210> SEQ ID NO 109
<211> LENGTH: 25
<212> TYPE: DNA
<213> ORGANISM: Artificial Sequence
<220> FEATURE:
<223> OTHER INFORMATION: third nucleic acid probe; L. (V.) braziliensis
      kDNA 3 Taqman probe

<400> SEQUENCE: 109
ttgcagaacg cccctaccca gaggc                                          25

<210> SEQ ID NO 110
<211> LENGTH: 24
<212> TYPE: DNA
<213> ORGANISM: Artificial Sequence
<220> FEATURE:
<223> OTHER INFORMATION: third nucleic acid probe; kDNA 5 minicircle
      Taqman probe

<400> SEQUENCE: 110
ttttcgcaga acgcccctac ccgc                                           24

<210> SEQ ID NO 111
<211> LENGTH: 20
<212> TYPE: DNA
<213> ORGANISM: Artificial Sequence
<220> FEATURE:
<223> OTHER INFORMATION: third nucleic acid probe; L (L.) infantum
      Minicircle 1 Taqman probe

<400> SEQUENCE: 111
ctgagagacc cgccggggcg                                                20

<210> SEQ ID NO 112
<211> LENGTH: 25
<212> TYPE: DNA
<213> ORGANISM: Artificial Sequence
<220> FEATURE:
<223> OTHER INFORMATION: third nucleic acid probe; DNA polymerase 1
      Taqman probe

<400> SEQUENCE: 112
cagcaacaac ttcgagcctg gcacc                                          25
```